(12) United States Patent
Curatolo et al.

(10) Patent No.: US 12,372,810 B2
(45) Date of Patent: Jul. 29, 2025

(54) OPHTHALMIC LENS

(71) Applicant: SIFI S.P.A., Aci Sant'Antonio (IT)

(72) Inventors: Maria Cristina Curatolo, Viagrande (IT); Renato Frison, Chions (IT)

(73) Assignee: SIFI S.P.A.

( * ) Notice: Subject to any disclaimer, the term of this patent is extended or adjusted under 35 U.S.C. 154(b) by 432 days.

(21) Appl. No.: 18/000,017

(22) PCT Filed: May 28, 2021

(86) PCT No.: PCT/IB2021/054705
§ 371 (c)(1),
(2) Date: Nov. 28, 2022

(87) PCT Pub. No.: WO2021/240465
PCT Pub. Date: Dec. 2, 2021

(65) Prior Publication Data
US 2023/0221579 A1     Jul. 13, 2023

(30) Foreign Application Priority Data

May 28, 2020 (IT) .................. 102020000012721

(51) Int. Cl.
G02C 7/04       (2006.01)
A61F 2/16       (2006.01)
G02C 7/02       (2006.01)

(52) U.S. Cl.
CPC ............ G02C 7/044 (2013.01); A61F 2/1618 (2013.01); G02C 7/028 (2013.01)

(58) Field of Classification Search
None
See application file for complete search history.

(56) References Cited

U.S. PATENT DOCUMENTS 5,225,853 A    7/1993    Valdemar
6,241,355 B1   6/2001    Barsky
(Continued)

FOREIGN PATENT DOCUMENTS

DE    102005022683 A1    11/2006
JP    2017526517 A       9/2017
(Continued)

OTHER PUBLICATIONS

Patent Cooperation Treaty, International Search Report and Written Opinion for International Application No. PCT/IB2021/054705, mailed Dec. 21, 2021, 24 pages.
(Continued)

Primary Examiner — Darryl J Collins
(74) Attorney, Agent, or Firm — Stetina Garred Brucker & Newboles

(57) ABSTRACT

An implantable or wearable lens for ophthalmic use, having a front surface and a rear surface, wherein at least one surface of said front surface and rear surface has an aspherical refractive profile with circular or rotational symmetry, or with cylindrical or non-rotational symmetry, with respect to the optical axis, and having a geometric elevation z(r) defined by a series expansion of Forbes polynomials, wherein said refractive profile generates an enhancement of the wavefront W(r) emerging from the lens such as to extend the depth of field thereof progressively and continuously in a power range between −1.0 D and 4.0 D.

18 Claims, 24 Drawing Sheets

(56) References Cited

U.S. PATENT DOCUMENTS

| | | | |
|---|---|---|---|
| 6,547,882 B1 | 4/2003 | Lang | |
| 7,455,404 B2* | 11/2008 | Bandhauer | A61F 2/1618 359/571 |
| 2001/0002859 A1 | 6/2001 | Portney | |
| 2003/0063254 A1 | 4/2003 | Piers | |
| 2004/0106992 A1* | 6/2004 | Lang | A61F 2/1618 623/901 |
| 2005/0068494 A1 | 3/2005 | Griffin | |
| 2010/0057202 A1 | 3/2010 | Bogaert | |
| 2010/0073629 A1* | 3/2010 | Menezes | G02C 7/044 351/159.12 |
| 2010/0097569 A1* | 4/2010 | Weeber | G02C 7/06 623/6.3 |
| 2010/0134754 A1 | 6/2010 | Hong et al. | |
| 2010/0234943 A1 | 9/2010 | Portney | |
| 2013/0050637 A1 | 2/2013 | Roffman | |
| 2019/0227344 A1 | 7/2019 | Bakaraju | |
| 2022/0401210 A1* | 12/2022 | Sanger | A61F 2/1618 |

FOREIGN PATENT DOCUMENTS

| | | |
|---|---|---|
| JP | 2018510372 A | 4/2018 |
| WO | 2016111851 A1 | 7/2016 |
| WO | 2020016431 A2 | 1/2020 |

OTHER PUBLICATIONS

Philip Greengard et al., "Zernike Polynominals: Evaluation, Quadrature, and Interpolation", arxiv.org, Cornell University Library, 201 Olin Library Cornell University Ithaca, NY 14853, Nov. 7, 2018, XP081047071, the whole document.

Japanese Office Action for Japanese Patent Application No. 2022-571153; mailed Nov. 26, 2024.

* cited by examiner

OPHTHALMIC LENS

CROSS-REFERENCE TO RELATED APPLICATIONS

This application claims priority to PCT International Application No. PCT/IB2021/054705 filed on May 28, 2021, which application claims priority to Italian Patent Application No. 102020000012721 filed on May 28, 2020, the entire disclosures of which are expressly incorporated herein by reference.

STATEMENT RE: FEDERALLY SPONSORED RESEARCH/DEVELOPMENT

Not Applicable

BACKGROUND

Field of the Invention

The present invention relates to a lens for ophthalmic use adapted to vary the depth of field, and more particularly to a lens with optimal behavior even when specific, even extensive, variations of depth of field are required, without compromising the vision quality.

Background Art

As is known, there are lenses for ophthalmic use which have at least one of the two aspherical surfaces defined by a single polynomial power series expansion of even order.

The purpose of these lenses is to vary the depth of field, manipulating the spherical aberration in the different zones of the optics defined as aspherical.

The surface of such lenses can be divided into concentric adjacent zones between which a discontinuity can exist and in which the aspherical surface is described by means of a single polynomial expansion expressed with a power series of even order.

Other technical solutions for ophthalmic lenses consist of a first front surface and a second rear surface, where one of the two surfaces comprises a refractive profile while the other surface comprises a diffractive profile; in turn the refractive surface can be defined by a continuous aspherical profile of higher order.

The technical solutions available suggest the use of an aspherical refractive surface defined by a power series expansion of even order up to high orders above the 4th order, at most up to the 6th order.

This type of technical solution does not allow manipulating the spherical aberration of orders greater than or equal to the 4th order so as to optimize the vision quality in the specific depth of field range. Aspherical surfaces are defined by a continuous aspherical profile of high order which describes the elevation of a given number of zones in a single equation. Given the numerical approximation attributable to the use of the polynomial in power series and given the number of said zones, defined in a manner unrelated to an optimization of the vision quality in the depth of field range considered, with the aspherical refractive lens expressed through the polynomial expansion of powers, it is not allowed to define a profile which allows manipulating the spherical aberration in a robust manner and expressing, in a manner less prone to errors, the number of zones and the elevation variations of the lens surface in said zones required to enhance the wavefront corresponding to the depth of field range to be reached.

The numerical approximation attributable to the use of the polynomial in power series of the aspherical surfaces can be highly inefficient and numerically unstable, i.e., prone to rounding errors. The main reason for these limitations is the fact that the set of polynomials used to represent the aspherical surface (even order powers) is not orthogonal.

The number of lens zones described in the prior art and the elevation of said zones, if defined in a manner unrelated to an optimization of vision quality in the specific depth of field range, does not allow manipulating the spherical aberrations without compromising vision quality.

Therefore, there is a need to create an innovative lens which allows overcoming the aforesaid drawbacks found in lenses according to the prior.

SUMMARY OF THE INVENTION

It is the object of the present invention to provide an intraocular or wearable lens adapted to allow specific, even extensive, variations of the depth of field without compromising the vision quality in the reference range.

It is another object of the invention to provide a lens in which, for different pupil diameters, at least one surface of the lens is characterized by zones adapted to optimize the TFMTF (through focus modulation transfer function) in a desired range of vision and enhance the wavefront so as to make the extended variation of the depth of field possible without compromising vision quality. TFMTF is a transfer function which describes the vision quality through the lens optics.

Therefore, the present invention aims to achieve the objects discussed above by providing, according to a first aspect, an implantable or wearable corrective lens for ophthalmic use, having a front surface and a rear surface, where at least one surface of said front surface and rear surface has an aspherical refractive profile with circular or rotational symmetry, or with cylindrical or non-rotational symmetry, with respect to the optical axis and divided into a number Y of mutually coaxial zones, with Y varying from 2 to 8, the profile of each zone being of refractive type only and having a geometric elevation $z(r)$ defined by a series extension or expansion of Forbes polynomials at least up to the third term $$z(r) = \frac{cr^2}{1 + \sqrt{1 - (1+k)c^2 r^2}} + \left(\frac{r}{r_{max}}\right)^4 \sum_{i=0}^{x} q_i Q_i\left(\left(\frac{r}{r_{max}}\right)^2\right)$$

where
i=variable number from 0 to x, with $2 \leq x \leq 11$,
r=aperture radius (or radial aperture) of the at least one surface, which is variable from 0 to $r_{max}$,
c=inverse of the radius of curvature R, or curvature, of the base sphere of said at least one surface,
k=conical constant of said at least one surface,
$r_{max}$=maximum aperture radius of said at least one surface,
$Q_i$=Jacobi polynomials of index ($\alpha$=0 and $\beta$=4)
$q_i$=coefficients of the Jacobi polynomials $Q_i$,
wherein the value of all the coefficients $q_i$ is different from zero for the refractive profile of a number of zones equal to Y−1, and is equal to zero for the refractive profile of the outermost zone, preferably wherein the coefficients ($q_o$, ... $q_x$) of the Jacobi polynomials for defining the refractive profile of each coaxial zone are in the following range $-0.422 \leq q_i \leq 0.800$.

Thereby, the aforesaid refractive profile generates an optimization of the TFMTF and an enhancement of the wavefront W(r) emerging from the lens which yields a variation of the depth of field of the lens in a desired power range, between −1 D and +4.0 D (D=diopters), without compromising the vision quality, therefore with an additional power up to +4.0 D excluding the 0 D value.

Preferably a spherical aberration is provided (induced) only in an inner or central zone and in the intermediate annular zones of said coaxial zones, said spherical aberration being preferably from the fourth order to the eighth order, and an optical power discontinuity is always provided between each coaxial zone and the next one.

Considering a second aspect, the present invention aims to achieve the aforementioned objects by providing an implantable or wearable corrective lens for ophthalmic use, having a front surface and a rear surface, wherein at least one surface of said front surface and rear surface has an aspherical refractive profile with circular or rotational symmetry, or with cylindrical or non-rotational symmetry, with respect to the optical axis and divided into a number Y of mutually coaxial zones, with Y varying from 3 to 8, the profile of each zone being of refractive type only, wherein said coaxial zones consist of an inner or central zone ($Z_{in}$) extending from the optical axis to a first outer radius $r_{in}$, at least one intermediate annular zone ($Z_{int}$) extending from said first outer radius $r_{in}$ to a second outer radius $r_{int}$, and an outer annular zone ($Z_{out}$) extending from said second outer radius $r_{int}$ to a third outer radius $r_{out}$ coinciding with the outer radius of the lens surface;

wherein only in the central zone ($Z_{in}$) and in the at least one intermediate annular zone ($Z_{int}$) there is provided (or induced) a spherical aberration, from the fourth order to the eighth order, while the outer annular zone ($Z_{out}$) has an aspherical monofocal profile with optical power such as to correct or cancel the positive spherical aberration of the cornea.

With reference to both of the aforesaid aspects of the invention, a first lens variant provides said at least one surface provided with three concentric coaxial zones (Z1, Z2, Z3) with circular symmetry; wherein the optical power of the central zone (Z1) decreases from a first value P1 to a second value P2 at a first outer radius $r_1$; wherein the optical power in the intermediate annular zone (Z2) and in the outer annular zone (Z3) decreases from a third value P3 at the first outer radius $r_1$ to a fourth value P4 at the third outer radius $r_3$; in which P2<P4<P3<P1 or P4<P2<P3<P1.

With reference to both aspects of the invention, a second lens variant provides said at least one surface provided with five concentric coaxial zones (Z1, Z2, Z3, Z4, Z5) with circular symmetry; wherein, as the radius increases, the optical power of the central zone (Z1) starting from the center of the lens increases from a first value P1 to a second value P2 in a first central sub-zone in the presence of a positive spherical aberration;

decreases from said second value P2 to a third value P3 in a second central sub-zone in the presence of a negative spherical aberration;

increases from said third value P3 to a fourth value P4 at the first outer radius r1 in the presence of a positive spherical aberration in a third central sub-zone;

preferably wherein the optical power in the first intermediate annular zone (Z2) starting from the first outer radius r1 decreases from a fifth value P5 to a sixth value P6 in the presence of a negative spherical aberration in an initial part of said first intermediate annular zone (Z2), and increases from said sixth value P6 to a seventh value P7 at the second outer radius r2 in the presence of a positive spherical aberration in a final part of said first intermediate annular zone (Z2);

preferably wherein both the fifth value P5 and the sixth value P6 are in the range between the third value P3 and the fourth value P4, and wherein the seventh value P7 is greater than the average power value of the central zone (Z1);

preferably wherein the optical power in the second intermediate annular zone (Z3) starting from the second outer radius r2 increases from an eighth value P8 to a ninth value P9 in the presence of a positive spherical aberration in an initial part of said second intermediate annular zone (Z3);

and decreases from said ninth value P9 to a tenth value P10 at the third outer radius r3 in the presence of a negative spherical aberration in a final part of said second intermediate annular zone (Z3), preferably wherein both the eighth value P8 and the ninth value P9 are in the range between the third value P3 and the fourth value P4, and wherein the tenth value P10 is less than the average power value of the central zone (Z1);

preferably wherein the optical power in the third intermediate annular zone (Z4) starting from the third outer radius r3 decreases from an eleventh value P11 to a twelfth value P12 at the fourth outer radius r4 in the presence of a negative spherical aberration; preferably wherein the average power value in said third intermediate annular zone (Z4) substantially corresponds to the average power value in the central zone (Z1);

preferably wherein the optical power in the outer annular zone (Z5) starting from the fourth outer radius r4 decreases from a thirteenth value P13 to a fourteenth value P14 at the fifth outer radius r5; preferably in which P12<P14<P13<P11.

With reference to both aspects of the invention, a third lens variant provides said at least one surface provided with five concentric coaxial zones (Z1, Z2, Z3, Z4, Z5) with circular symmetry; wherein, as the radius increases, the optical power of the central zone (Z1) starting from the center of the lens decreases from a first value P1 to a second value P2 in the presence of a negative spherical aberration in a first central sub-zone;

and increases from said second value P2 to a third value P3 at the first outer radius r1 in the presence of a positive spherical aberration in a second central sub-zone;

preferably wherein the optical power in the first intermediate annular zone (Z2), starting from the first outer radius r1, decreases from a fourth value P4 to a fifth value P5 in the presence of a negative spherical aberration in said first intermediate annular zone (Z2);

preferably wherein the fourth value P4 is less than the second value P2;

preferably wherein the optical power in the second intermediate annular zone (Z3) starting from the second outer radius r2 decreases from a sixth value P6 to a seventh value P7 in the presence of a negative spherical aberration in an initial part of said second intermediate annular zone (Z3);

and increases from said seventh value P7 to an eighth value P8 at the third outer radius r3 in the presence of a positive spherical aberration in a final part of said second intermediate annular zone (Z3), preferably wherein both the sixth value P6 and the seventh value P7 are in the range between the fourth value P4 and the fifth value P5, and in which the eighth value P8 is greater than the average power value of the central zone (Z1);

preferably wherein the optical power in the third intermediate annular zone (Z4) starting from the third outer radius r3 increases from a ninth value P9 to a tenth value P10 and decreases from said tenth value P10 to an eleventh value P11 at the fourth outer radius r4 in the presence of an overall negative spherical aberration in said third intermediate annular zone (Z4);

preferably wherein the optical power in the outer annular zone (Z5) starting from the fourth outer radius r4 decreases from a twelfth value P12 to a thirteenth value P13 at the fifth outer radius r5; preferably wherein the average power value between P12 and P13 substantially corresponds to the average power value in the central zone (Z1).

With reference to both aspects of the invention, a fourth lens variant provides said at least one surface provided with seven concentric coaxial zones (Z1, Z2, Z3, Z4, Z5, Z6, Z7) with circular symmetry; wherein, as the radius increases, the optical power of the central zone (Z1) starting from the center of the lens decreases from a first value P1 to a second value P2 in the presence of a negative spherical aberration in a first central sub-zone;

increases from said second value P2 to a third value P3 in the presence of a positive spherical aberration in a second central sub-zone;

and decreases from said third value P3 to a fourth value P4 at the first outer radius r1 in the presence of a negative spherical aberration in a third central sub-zone;

preferably wherein the optical power in the first intermediate annular zone (Z2) starting from the first outer radius r1 decreases from a fifth value P5 to a sixth value P6 in the presence of a negative spherical aberration in an initial part of said first intermediate annular zone (Z2), increases from said sixth value P6 to a seventh value P7 in the presence of a positive spherical aberration in an intermediate part of said first intermediate annular zone (Z2);

and decreases from said seventh value P7 to an eighth value P8 in the presence of a negative spherical aberration in a final part of said first intermediate annular zone (Z2), preferably wherein said eighth value P8 coincides with said fifth value P5 and is less than the fourth value P4;

preferably wherein the optical power in the second intermediate annular zone (Z3) starting from the second outer radius r2 decreases from a ninth value P9 to a tenth value P10 in the presence of a negative spherical aberration in an initial part of said second intermediate annular zone (Z3);

and increases from said tenth value P10 to an eleventh value P11 at the third outer radius r3 in the presence of a positive spherical aberration in a final part of said second intermediate annular zone (Z3), preferably wherein both the ninth value P9 and the tenth value P10 are in the range between the sixth value P6 and the seventh value P7, and wherein the eleventh value P11 is greater than the average power value of the central zone (Z1);

preferably wherein the optical power in the third intermediate annular zone (Z4) starting from the third outer radius r3 decreases from a twelfth value P12 to a thirteenth value P13 in the presence of a negative spherical aberration in an initial part of said third intermediate annular zone (Z4), increases from said thirteenth value P13 to a fourteenth value P14 in the presence of a positive spherical aberration in an intermediate part of said third intermediate annular zone (Z4), and decreases from said fourteenth value P14 to a fifteenth value P15 at the fourth outer radius r4 in the presence of a negative spherical aberration in a final part of said third intermediate annular zone (Z4);

preferably wherein the optical power in the fourth intermediate annular zone (Z5) starting from the fourth outer radius r4 decreases from a sixteenth value P16 to a seventeenth value P17 at the fifth outer radius r5, in the presence of a negative spherical aberration in said fourth intermediate annular zone (Z5), preferably wherein the optical power in the fifth intermediate annular zone (Z6) starting from the fifth outer radius r5 decreases from an eighteenth value P18 to a nineteenth value P19 at the sixth outer radius r6, in the presence of a negative spherical aberration in said fifth intermediate annular zone (Z6), preferably wherein the optical power in the outer annular zone (Z7) starting from the sixth outer radius r6 decreases from a twentieth value P20 to a twenty-first value P21 at the seventh outer radius r7; preferably wherein the average power value between P20 and P21 substantially corresponds to the average power value of the central zone (Z1).

With reference to both aspects of the invention, a fifth lens variant provides said at least one surface provided with three concentric coaxial zones (Z1, Z2, Z3) with cylindrical symmetry; wherein the optical power of the central zone (Z1) decreases from a first value P1T, and/or P1S, to a second value P2T, and/or P2S, at the first outer radius r1; wherein the optical power in the intermediate annular zone (Z2) and in the outer annular zone (Z3) decreases from a third value P3T, and/or P3S, at the first outer radius r1 to a fourth value P4T, and/or P4S, at the third outer radius r3; wherein PT is the tangential power and PS is the sagittal power; preferably wherein P2T<P4T<P3T<P1T and/or P2S<P4S<P3S<P1S, or P4T<P2T<P3T<P1T and/or P4S<P2S<P3S<P1S.

Another aspect of the invention relates to an intraocular lens wherein said refractive profile is aspherical with circular or rotational symmetry with respect to the optical axis and has said geometric elevation z(r), and wherein the one of the front surface and the rear surface of the lens, which does not have said aspherical refractive profile with circular or rotational symmetry, comprises at least one cylindrical portion.

A further aspect of the invention further relates to a two-lens system such as those described above, said two lenses being complementary for an extension of the depth of field in binocular vision.

In the description of the present invention, the following technical terms have the following respective definitions.

Depth of field means the distance separating the two extreme points, which limit the front and back of the zone of the space where a recognizable object can be found. This value can be measured in millimeters. The depth of field can also be expressed in diopters by applying the formula: PC[D]=1000/PC[mm], where PC[D]=depth of field in diopters and PC[mm]=depth of field in mm.

Depth of focus means the range of focusing planes in which the ability to recognize the object is preserved.

Geometric elevation z(r) means the sagittal elevation (Sagittal height) of a surface.

The lens of the invention has a refractive optical design with circular or cylindrical symmetry on at least one of the two surfaces which enhances the emerging wavefront so as to extensively vary the depth of field.

The wavefront enhancement is such as to correspond to a desired range of vision extension, expressed through a target function Target (d, y) which describes the Through Focus Modulation Transfer Function (TFMTF) as a function of a predetermined pupil diameter d and a determined focusing position on the retina y (focus shift) expressed in mm, or as a function of a predetermined pupil diameter d and a depth of field expressed in diopters.

Preferably, at least one surface of the lens of the invention, front or rear surface, is divided into a plurality of coaxial, e.g. concentric, annular zones or portions, the aspherical profile of which is obtained by separately describing the aspherical profile of each ring or zone by a series of Forbes polynomials. Said portions are annular except for the central or innermost portion of the lens surface. Advantageously, the lens of the present invention allows the depth of field to be extended by dividing the (front or rear) surface into a plurality of concentric annular portions or zones of refractive-only type.

The division into annular portions is such as not to require the introduction of a thickness discontinuity in the junction or transition zone between two adjacent zones or portions, for example as shown in FIG. 5, thereby reducing the risk of occurrence of vision side effects (halos and glare).

Each zone of the lens surface is not simply configured to extend the depth of field at a well-defined distance from the patient's eye, but to extend it in a more or less wide region of distances from the patient: in fact, each zone partially and separately contributes to improving vision in both the near field and the far field. The profile of each surface ring or zone is obtained by a series of Forbes polynomials.

Forbes polynomials are advantageous for defining aspherical surfaces compared to the classical polynomial expansion (with a series of powers of even order) since they have units of length and therefore the value thereof also represents the contribution thereof to surface variation, for example, in mm. Furthermore, unlike the power series where the coefficients are statistically insignificant if establishing a tolerance on the coefficient itself is sought, the Forbes polynomial coefficients can be assigned tolerances which are significant for the design and construction of the aspherical surface. Applied to define the surface, the Forbes series minimizes the difference between the real TFMTF (D, y), obtained by simulating the behavior of the lens of the invention within an optical model of the human eye, and a reference TFMTF function known as Target (D, y) and which describes the desired extension of the depth of field, simultaneously evaluating the extension for different pupil diameters, for example, between $d_1$=2.0 mm and $d_2$=4.5 mm.

Such a Forbes series has been introduced in order to provide a more robust representation of the aspherical surfaces of individual lens optics zones.

The aspherical surface described, in the prior art, by means of a polynomial in traditional power series is broken down into two parts: a base component (conical section) and a power series of even order $$\{P_i\} = S(r) = \frac{cr^2}{1+\sqrt{1-(1+k)c^2r^2}} + \sum_{m=0}^{M} a_m \left( \left( \frac{r}{r_{max}} \right)^{2m+4} \right)$$

which takes into account the deviations of the surface from the conical base, according to the following formula:

$$S(r) = \frac{cr^2}{1+\sqrt{1-(1+k)c^2r^2}} + \sum_{m=0}^{M} a_m \left( \left( \frac{r}{r_{max}} \right)^{2m+4} \right)$$

where c=1/R, the curvature of the surface, and x, the conical constant, define the conical section.

The approximation of such a generic aspherical surface S(r) is obtained by a numerical procedure known as the least squares method.

It is known that the numerical stability of this solution strongly depends on the choice of polynomials $\{P_i\}$. However, having found that the stability of the solution improves if we choose the polynomials $\{P_i\}$ so that they are orthogonal to each other, the inventors have discarded the use, provided in the prior art, of the polynomials power series $\{P_i\}$ since they are not orthogonal to one another.

Forbes represents aspherical surfaces by introducing an alternative formula:

$$z(r) = \frac{cr^2}{1+\sqrt{1-(1+k)c^2r^2}} + \left( \frac{r}{r_{max}} \right)^4 \sum_{i=0}^{M} q_i Q_i \left( \left( \frac{r}{r_{max}} \right)^2 \right)$$

in which, beyond the conical base section, a term appears given by the sum of polynomials $\{Q_i\}$ of a different nature with respect to the polynomials $\{P_i\}$.

Also in the case of Forbes, the optimal coefficients $\{q_i\}$ are chosen to approximate a generic aspherical surface z(r), minimizing a quadratic functional, where the polynomials $\{Q_1\}$, which satisfy the orthogonality condition, correspond to Jacobi polynomials of index ($\alpha$=0 and $\beta$=4), i.e., correspond to a scaled version of the classic Jacobi polynomials, $J_i^{(\alpha,\beta)}(r)$, with $\alpha$=0 and $\beta$=4, that is:

$Q_i(r) = J_i^{(0,4)}(2r-1)$, where r is the aperture radius opening radius of the at least one surface.

The enhancement of the wavefront $\Delta W(r)$, capable of introducing a variation of the depth of field of the lens, is proportional to the sum of the orthogonal polynomials multiplied by the coefficients thereof.

Furthermore, the coefficients $q_i$ are such as to minimize a merit function (M) defined by the difference between the Through Focus Modulation Transfer Function TFMTF(d, y) (for example at 50 lp/mm and for an arbitrary number of predetermined pupil diameters—for example 2.0 mm, 3.0 mm, 4.5 mm, etc.) of the human eye model in which the lens of the invention is inserted, or on which it is worn, and a target Through Focus Modulation Transfer Function, called Target (d, y), which, at the same spatial frequency as TFMTF(d, y) and for the same pupil diameters, expresses the desired depth of field extension. Examples of the target function, Target (d, y), are seen for example in FIGS. 7, 9, 11 and 13 (curves indicated with reference numeral 4).

The depth of field variation range, in which the minimization of the merit function M can tend to the absolute minimum thereof, can for example be between −1.0 D and 4.0 D.

The merit function M is defined by the following equation:

$$M = (\text{TFMTF}(d,y) - \text{Target}(d,y))^2 \qquad \text{Eq. 2}$$

where

TFMTF(d, y)=Through Focus Modulation Transfer Function of the lens;

Target (d, y)=target Through Focus Modulation Transfer Function;

y=focus shift position on the retina in mm, d=pupil diameter in mm.

The enhanced wavefront in a given depth of field range has a specific shape thereof, even discontinuous, referring to a fixed pupillary diameter, as depicted for example in FIG. 1.

In such a depth of field range, the energy distributed by the enhanced wavefront is described, as shown in FIG. 2, by the Through Focus Modulation Transfer Function TFMTF (d, y) defined in a range of non-negligible non-zero values and passing through a continuous succession of intermediate points of vision. The spatial frequency values can be between 25 lp/mm and 100 lp/mm.

In particular, the replacement of the wavefront enhancement ΔW(r) within the merit function M (Equation 2) and the resulting numerical minimization lead to a series of coefficients $q_i$ which define the TFMTF(d, y) depicted in the graph in FIG. 2, for example referring to a spatial frequency of 50 lp/mm and a pupil diameter of 3.0 mm, which closely approximates the function Target (d, y). The overall wavefront associated with the function TFMTF(d, y) is depicted in the graph in FIG. 1 where the axis of the abscissa represents the normalized coordinate corresponding to the pupillary radius and the axis of the ordinates represents the corresponding variation value of the wavefront expressed in μm. A profile of a surface (e.g., the front surface) of an intraocular or wearable lens corresponds to this specific wavefront. Finally, the power distribution associated with the profile of the lens, referring to the pupil diameter, can be obtained from the expression of the wavefront as follows (see Eq. 5 below).

The dependent claims describe further possible embodiments of the invention.

BRIEF DESCRIPTION OF THE DRAWINGS

Further features and advantages of the present invention will become more apparent in light of the detailed description of non-exclusive embodiments of a lens disclosed by way of non-limiting example, with the aid of the accompanying drawings, in which:

FIGS. 13d-13l depict the trend of the optical power of said fourth lens in the respective zones;

The same reference numerals in the figures identify the same elements or components.

DETAILED DESCRIPTION OF PREFERRED EMBODIMENTS OF THE INVENTION

The lens of the invention has a refractive optical design with circular or rotational symmetry, or with non-rotational or cylindrical symmetry, with respect to the optical axis on at least one of the two surfaces, front and rear surfaces, and enhances the emerging wavefront W(r) so as to extensively vary the depth of field.

Advantageously, the optical design of the lens of the invention which enhances the wavefront W(r) is represented by the geometric elevation z(r) of a number Y of coaxial zones, with Y varying from 2 to 8, preferably from 3 to 7, of an aspherical refractive profile, with circular or cylindrical symmetry with respect to the optical axis, of at least one surface of the front surface and the rear surface of the lens. Said geometric elevation z(r), or sagittal height, of the coaxial zones is defined through a respective expansion in Forbes polynomials at least up to the third term and at most up to the twelfth term (Eq. 3):

$$z(r) = \frac{cr^2}{1 + \sqrt{1-(1+k)c^2r^2}} + \left(\frac{r}{r_{max}}\right)^4 \sum_{i=0}^{x} q_i Q_i\left(\left(\frac{r}{r_{max}}\right)^2\right)$$

where
i=variable number from 0 to x, with $2 \leq x \leq 11$,
r=aperture radius of at least one of the two lens surfaces, which is variable from 0 to $r_{max}$,
c=curvature of the base sphere of said at least one surface,
k=conical constant of said at least two surfaces,
$r_{max}$=maximum aperture radius of said at least one of the two surfaces,
$Q_i$=Jacobi polynomials of index ($\alpha$=0, $\beta$=4),
$q_i$=coefficients of the Jacobi polynomials $Q_i$.

Each variation of the coefficients $q_i$ directly corresponds to a variation of the geometric elevation of the lens surface. We show the basic idea of the invention with an example which highlights how, by appropriately modifying the geometric elevation of the surface (e.g., front surface) of an intraocular lens, a positive and/or negative power variation can be induced as a function of the radius, i.e., such as to distance (beyond the retina, if negative) or approach (before the retina, if positive) the focusing point (i.e., the energy distribution).

Figure 3:
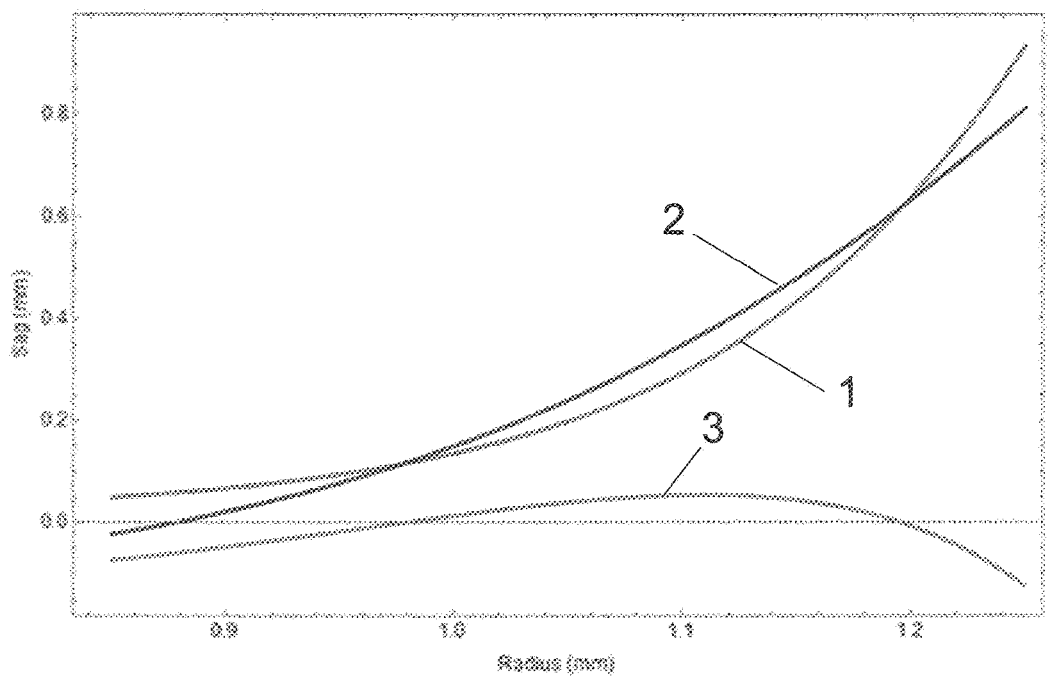
FIG. 3 depicts the geometric elevation of the surface of an intraocular lens for depth of field variation (red color) according to the invention, the geometric elevation of the surface of the same intraocular lens which does not apply the extended depth of field variation (blue color), and the geometric elevation difference (green color)

The elevation of said surface (e.g., front surface) of an intraocular lens for the depth of field variation is represented by curve 1 in FIG. 3. The curve 2, shown in the same FIG. 3, represents the trend of the geometric elevation of the surface (e.g., front surface) of the same intraocular lens which does not apply the extended depth of field variation.

The difference between the aforesaid geometric elevations, highlighted by curve 3, although slight, is not negligible and involves a wavefront variation expressed in first approximation by Equation 4 (Eq. 4)

$$\Delta W = (n_1 - n_2)\Delta z \qquad \text{Eq. 4}$$

where
$\Delta W$=wavefront variation;
$n_1$=refractive index of the aqueous humor;
$n_2$=refractive index of the lens material;
$\Delta z$=difference in geometric elevation of the surface of the lens of the invention with respect to an aspherical surface defined by a profile other than that of the invention.

This variation of the wavefront in turn causes a variation of power, which in general can also vary with discontinuity, and which is defined by the following equation (Eq. 5):

$$\Delta \Phi(r) = \frac{1}{r}\frac{dW(r)}{dr}$$

Figure 4A:
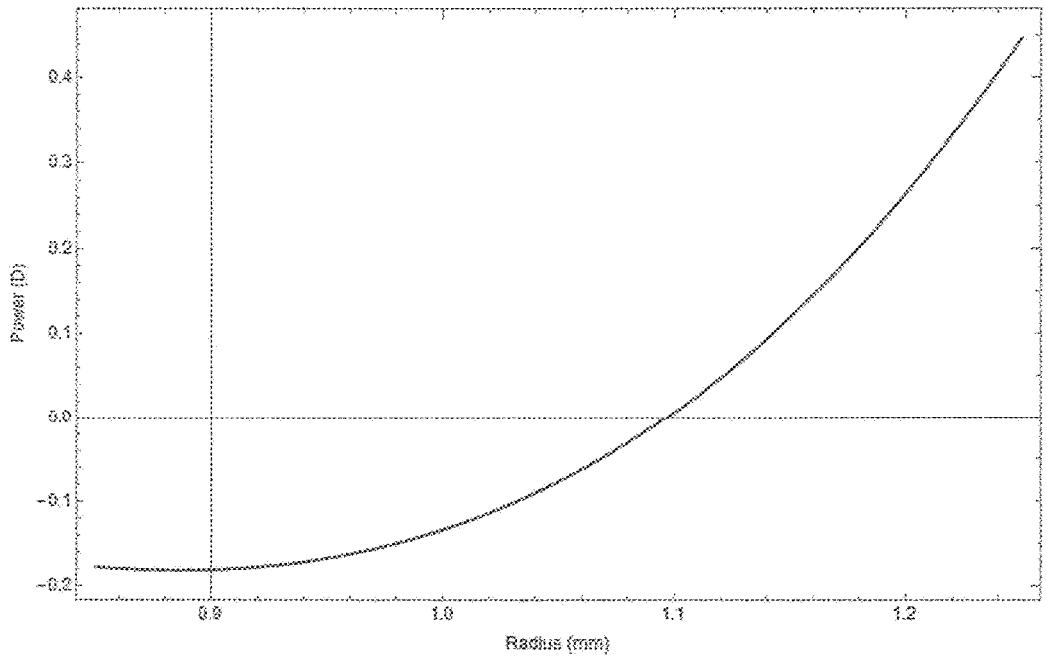
FIG. 4A depicts the power variation (in diopters) as a function of the radius of a lens extending for example from 0 to 1.5 mm.

In the example shown, such a trend is shown in the graph in FIG. 4A in which the power variation (in diopters) is represented as a function of the aperture radius of a lens, which extends for example from 0 to 1.5 mm.

It can be seen from the graph in FIG. 4A that the geometric elevation variation induces a power variation, slightly negative up to 1.1 mm radius and positive between 1.1 mm and 1.5 mm radius. This power variation therefore entails, with respect to the basic power, a redistribution of energy towards the far field within 1.1 mm radius and towards the near field between 1.1 mm and 1.5 mm radius, increasing the vision quality (or depth of field) in the respective distances.

Figure 4B:
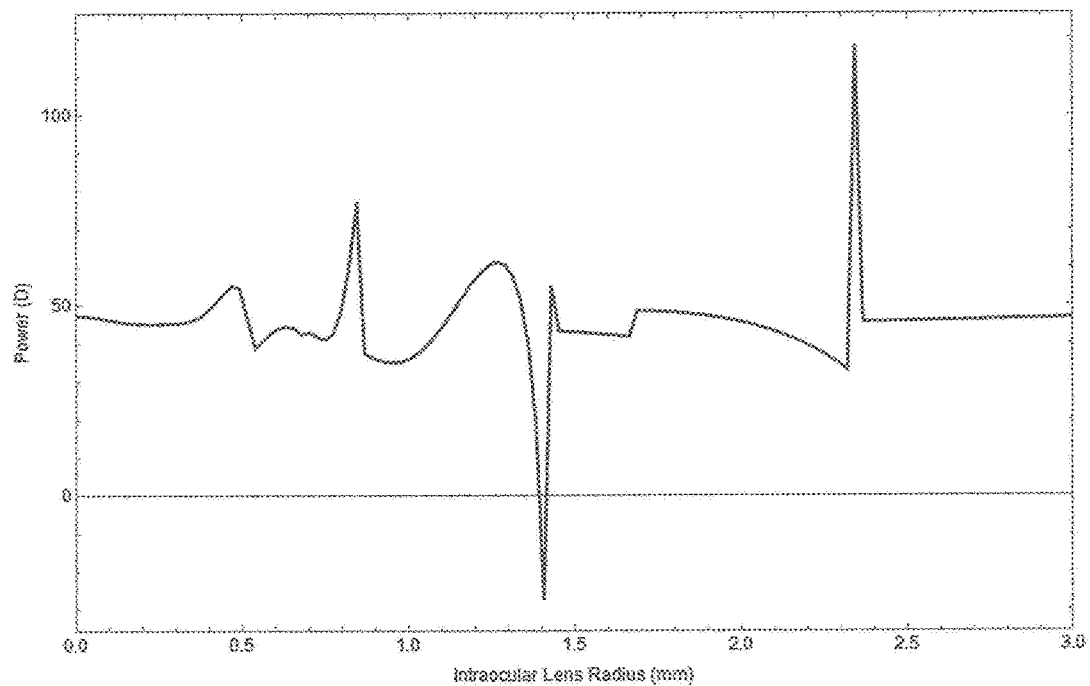
FIG. 4B depicts the power variation (in diopters) as a function of the radius of a lens extending from 0 to 3 mm and where the basic power of the lens is for example equal to +20 D.
Figure 5:
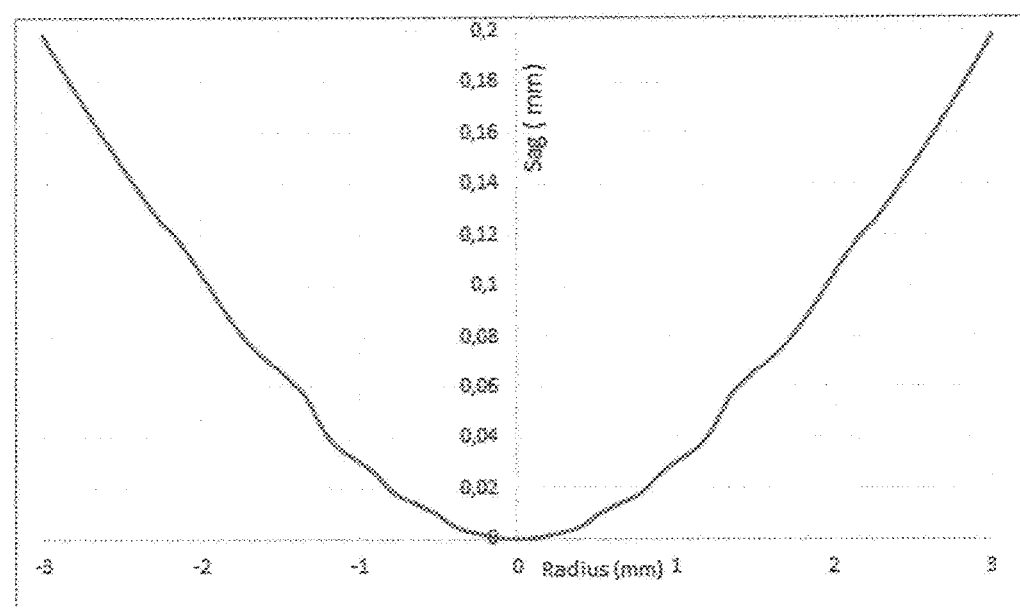
FIG. 5 depicts a profile of a surface of the lens of the invention which does not have discontinuity between adjacent zones.

The graph in FIG. 4B instead shows the variation in power (in diopters) as a function of the radius of a lens in a more complex case, with an intraocular lens radius extending for example from 0 to 3 mm and where the basic power of the lens is +20 D. It is noted that in general power variations characterized by the presence of peaks at some radii can emerge. The front (or rear) surface of the lens can be divided into a plurality of concentric zones delimited by progressive radii variable with respect to the center of the lens, obtained in response to an optimization of the TFMTF. In each of these zones the lens assumes a power, or a plurality of different powers, also obtained in response to an optimization of the TFMTF to an ideal reference TFMTF.

Some embodiments of the lens of the invention are illustrated below.

In all the embodiments thereof, the implantable or wearable corrective lens has a front surface and a rear surface.

Advantageously at least one surface of said front surface and rear surface has an aspherical refractive profile with rotational or circular symmetry, or with cylindrical or non-rotational symmetry, with respect to the optical axis and divided into a number Y of coaxial zones, with Y varying from 2 to 8, preferably from 3 to 7, the profile of each zone being of refractive type only and having a geometric elevation z(r) defined by a series expansion of Forbes polynomials at least up to the third term and at most up to the twelfth term (Eq. 3)

$$z(r) = \frac{cr^2}{1 + \sqrt{1-(1+k)c^2r^2}} + \left(\frac{r}{r_{max}}\right)^4 \sum_{i=0}^{x} q_i Q_i\left(\left(\frac{r}{r_{max}}\right)^2\right)$$

where
i=variable number from 0 to x, with $2 \leq x \leq 11$,
r=aperture radius of the at least one surface, which is variable from 0 to $r_m$,
c=curvature of the base sphere of said at least one surface, k=conical constant of said at least one surface,
$r_{max}$=maximum aperture radius of said at least one surface,
$Q_i$=Jacobi polynomials of index ($\alpha$=0, $\beta$=4),
$q_i$=coefficients of the Jacobi polynomials $Q_i$,
where the Jacobi polynomials $Q_i$ of index ($\alpha$=0 and $\beta$=4) correspond to a scaled version of the classic Jacobi polynomials, $J_i^{(\alpha,\beta)}(r)$, with $\alpha$=0 and $\beta$=4, i.e.:
$Q_i(r)=J_i^{(0,4)}(2r-1)$, where r is the aperture radius of the at least one surface.

Advantageously, the value of all the coefficients $q_i$ is non-zero for the refractive profile of a number of zones equal to Y−1, in particular the central zone and the intermediate zone(s), and is equal to zero for the refractive profile of the outermost zone.

Preferably, the coefficients ($q_o$, . . . $q_x$) of the Jacobi polynomials for defining the refractive profile of each coaxial zone are in the range
−0.422≤$q_i$≤0.800.

Such a refractive profile generates an enhancement of the wavefront W(r) emerging from the lens which produces a depth of field variation of the lens in a power range between −1 D and +4.0 D. In other words, the depth of field is progressively and continuously extended over a power range of −1.0 D to 4.0 D.

Preferably a spherical aberration is provided (induced) only in an inner or central zone and in the intermediate annular zones of said coaxial zones, said spherical aberration being preferably from the fourth order to the eighth order, and an optical power discontinuity is always provided between each coaxial zone and the next. However, no spherical aberration is introduced in the outermost zone.

Preferably, said at least one surface of said front surface or rear surface comprises Y zones coaxial with each other and with the axis of the pupil, each zone being described by the respective terms, in a variable number which is greater than or equal to 3 and less than or equal to 12, of the Forbes series expansion. These coaxial zones, except the central zone, are annular zones. Advantageously, said coaxial zones are adjacent to each other and a thickness continuity is provided in the junction or transition zone between two adjacent zones.

In a first embodiment of the lens of the invention, the aforementioned coaxial zones are concentric zones and the aspherical refractive profile has circular symmetry or rotational symmetry with respect to the optical axis.

Instead, in a second embodiment, the aforesaid coaxial zones are concentric zones and the aspherical refractive profile has cylindrical or non-rotational symmetry with respect to the optical axis.

Such coaxial zones can be a minimum of 2 and a maximum of 8, preferably a minimum of 3 and a maximum of 7, depending on the range of extension of the depth of field to be reached.

In all the embodiments of the invention, all of the aforesaid coaxial zones, i.e., the inner or central zone, one or more intermediate annular zones, and the outer annular zone, completely fill the aperture ("clear aperture") of the optics or lens.

In a first variant of said first embodiment, the lens of the invention has an aspherical refractive optical design, with circular symmetry with respect to the optical axis, on one of the two surfaces which enhances the emerging wavefront W(r) so as to extensively vary the depth of field in a power range between −0.25 D and 2.5 D. In particular, the refractive profile of the front or rear surface of the lens generates the wavefront enhancement.

Figure 6:
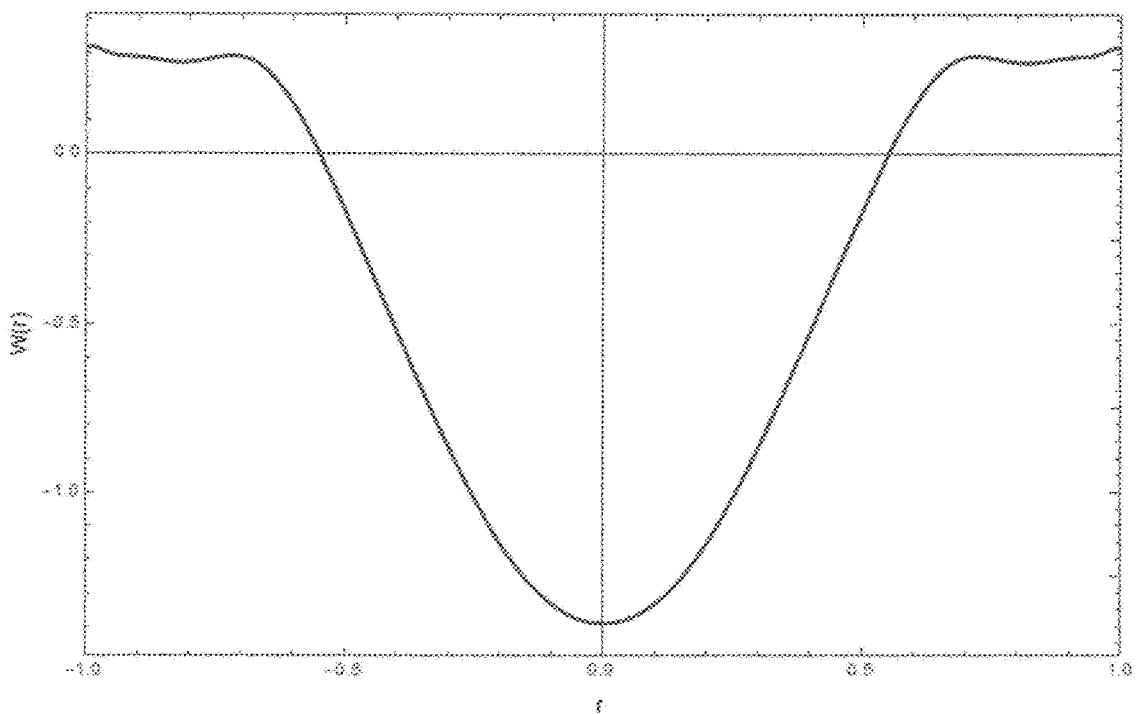
FIG. 6 depicts an enhanced wavefront in the range between −0.25 D and 2.5 D.

The enhanced wavefront in this specific depth of field range has a specific shape thereof as depicted, for example, in FIG. 6.

Figure 7:
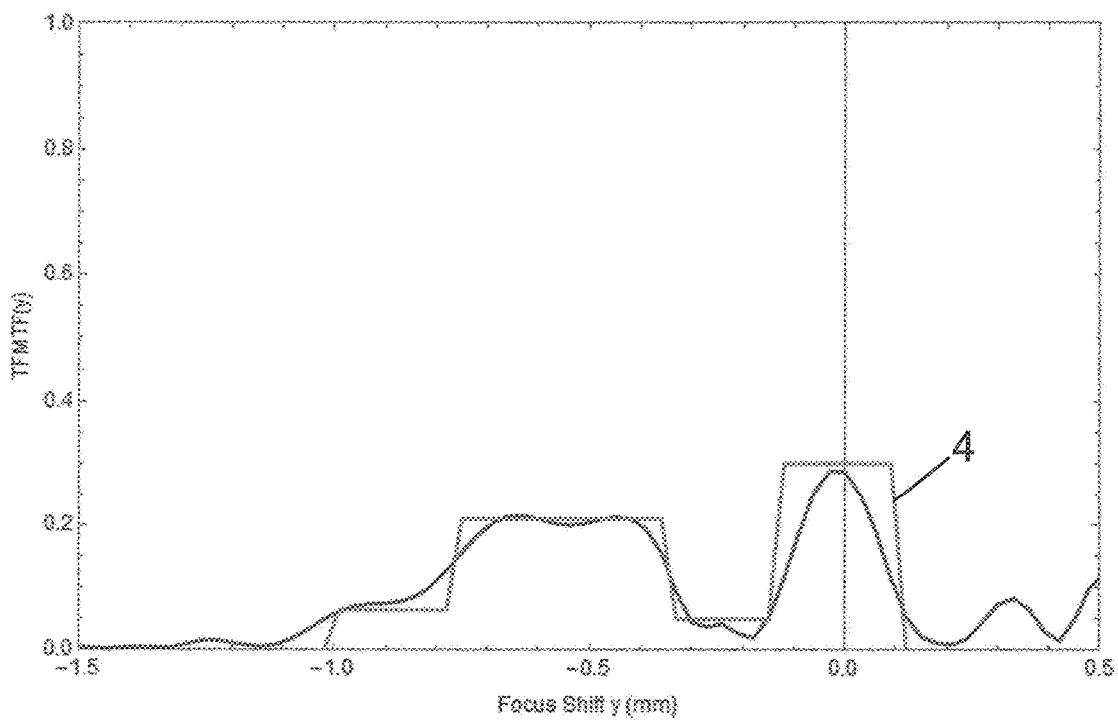
FIG. 7 depicts the Through Focus Modulation Transfer Function TFMTF at 50 lp/mm and a pupil diameter of 3.0 mm in the range between −0.25 D and 2.5 D as a function of the focus shift position y on the retina expressed in mm.

In such a depth of field range, the energy distributed by the enhanced wavefront is described, as shown in FIG. 7, by the Through Focus Modulation Transfer Function TFMTF (d, y) for a pupil diameter d=3.0 mm.

In this first variant said at least one surface, chosen between the front surface and the rear surface, comprises, or consists of, three concentric coaxial zones Z1, Z2, Z3 adjacent to one another and each delimited by a respective maximum radius or outer radius r1, r2, r3, where the coefficients $g_0$, . . . $q_2$ of the Jacobi polynomials for defining the refractive profile of each coaxial zone, by means of the Forbes polynomial expansion up to the third term, are in the following range
−0.363≤$q_i$≤0.021 with i=0, 1, 2.

In particular, the coefficients $q_o$, . . . $q_2$ are in the following ranges, respectively:
−3.63E-01≤$q_0$≤7.29E-04
−4.71E-02≤$q_1$≤−1.80E-13
−2.60E-13≤$q_2$≤2.05E-02.

In a second variant of said first embodiment, the lens of the invention has an aspherical refractive optical design, with circular symmetry with respect to the optical axis, on one of the two surfaces which enhances the emerging wavefront W(r) so as to extensively vary the depth of field in a power range between −0.25 D and 1.5 D. In particular, the refractive profile of the front or rear surface of the lens generates the wavefront enhancement.

Figure 8:
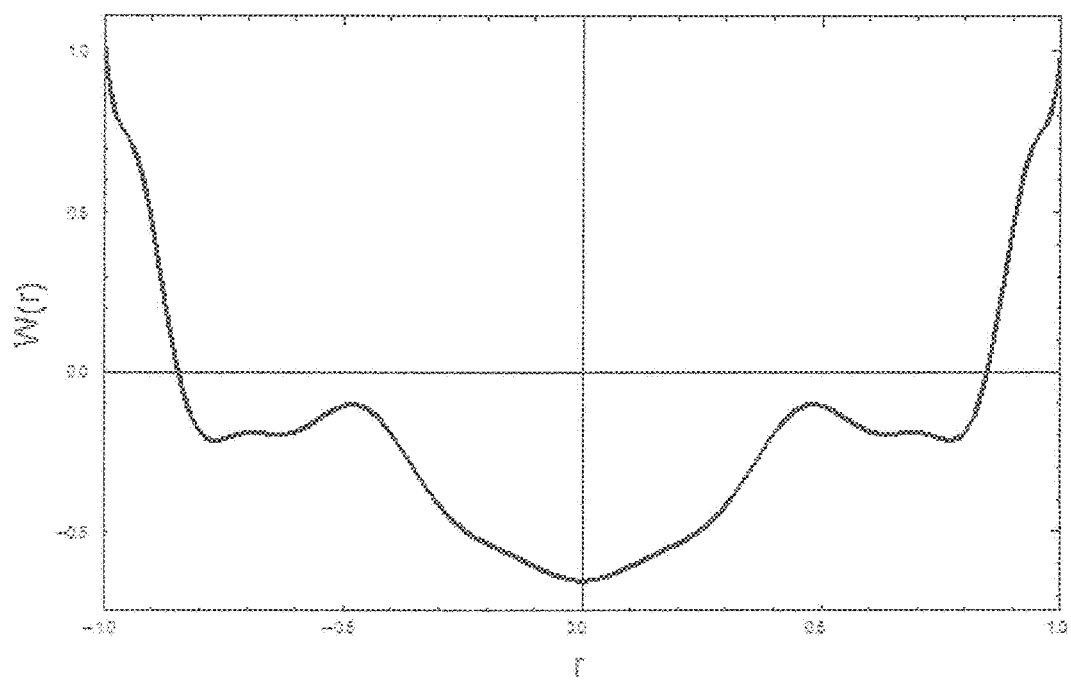
FIG. 8 depicts an enhanced wavefront in the range between −0.25 D and 1.5 D.

The enhanced wavefront in this specific depth of field range has a specific shape thereof as depicted in FIG. 8.

Figure 9:
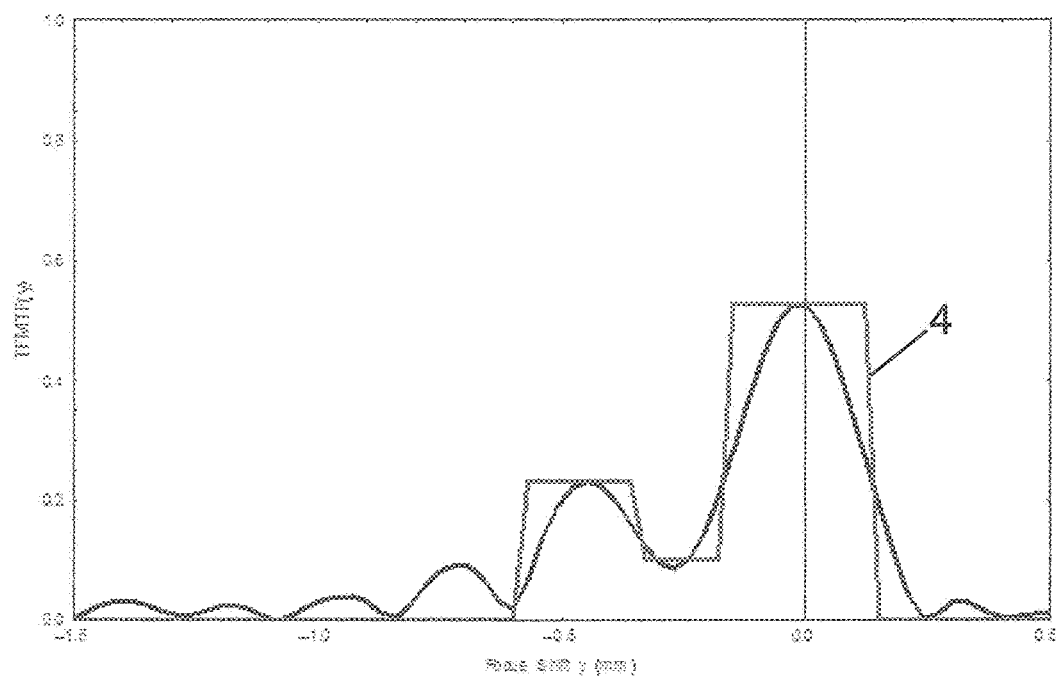
FIG. 9 depicts the Through Focus Modulation Transfer Function TFMTF at 50 lp/mm and a pupil diameter of 3.0 mm in the range between −0.25 D and 1.5 D as a function of the focus shift position y on the retina expressed in mm.

In such a depth of field range, the energy distributed by the enhanced wavefront is described, as shown in FIG. 9, by the Through Focus Modulation Transfer Function TFMTF (d, y) for a pupil diameter d=3.0 mm.

In this second variant at least one surface, chosen between the front surface and the rear surface, comprises, or consists of, five concentric coaxial zones Z1, Z2, Z3, Z4, Z5, adjacent to one another and each delimited by a respective maximum radius or outer radius r1, r2, r3, r4, r5, where the coefficients $q_o$, $q_{11}$ of the Jacobi polynomials for defining the refractive profile of each coaxial zone, by means of a Forbes polynomial expansion up to the twelfth term, are in the following range −0.422≤$q_i$≤0.700 with i=0, . . . 11.

In particular, the coefficients $q_o$, . . . $q_{11}$ are in the following ranges, respectively:
−5.58E-02≤$q_0$≤6.97E-01
−4.22E-01≤$q_1$≤3.63E-02
−1.87E-02≤$q_2$≤2.37E-01
−1.24E-01≤$q_3$≤9.45E-03
−5.48E-03≤$q_4$≤6.95E-02
−4.42E-02≤$q_5$≤3.81E-03
−2.59E-03≤$q_6$≤3.01E-02
−2.14E-02≤$q_7$≤1.84E-03
−1.36E-03≤$q_8$≤1.58E-02
−1.20E-02≤$q_9$≤1.03E-03
−8.00E-04≤$q_{10}$≤9.28E-03
−7.35E-03≤$q_{11}$≤6.34E-04.

In a third variant of said first embodiment, the lens of the invention has an aspherical refractive optical design, with circular symmetry with respect to the optical axis, on one of the two surfaces which enhances the emerging wavefront W(r) so as to extensively vary the depth of field in a power range between −0.25 D and 3.5 D. In particular, the refractive profile of the front or rear surface of the lens generates the wavefront enhancement.

Figure 10:
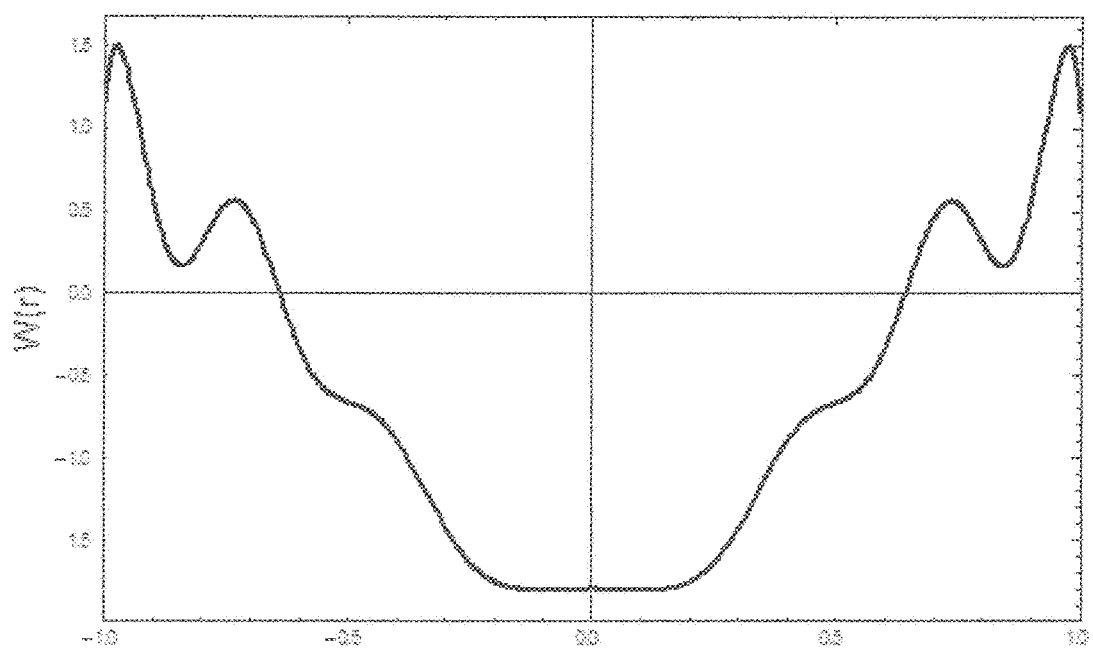
FIG. 10 depicts an enhanced wavefront in the range −0.25 D to 3.5 D.

The enhanced wavefront in this specific depth of field range has a specific shape thereof as depicted in FIG. 10.

Figure 11:
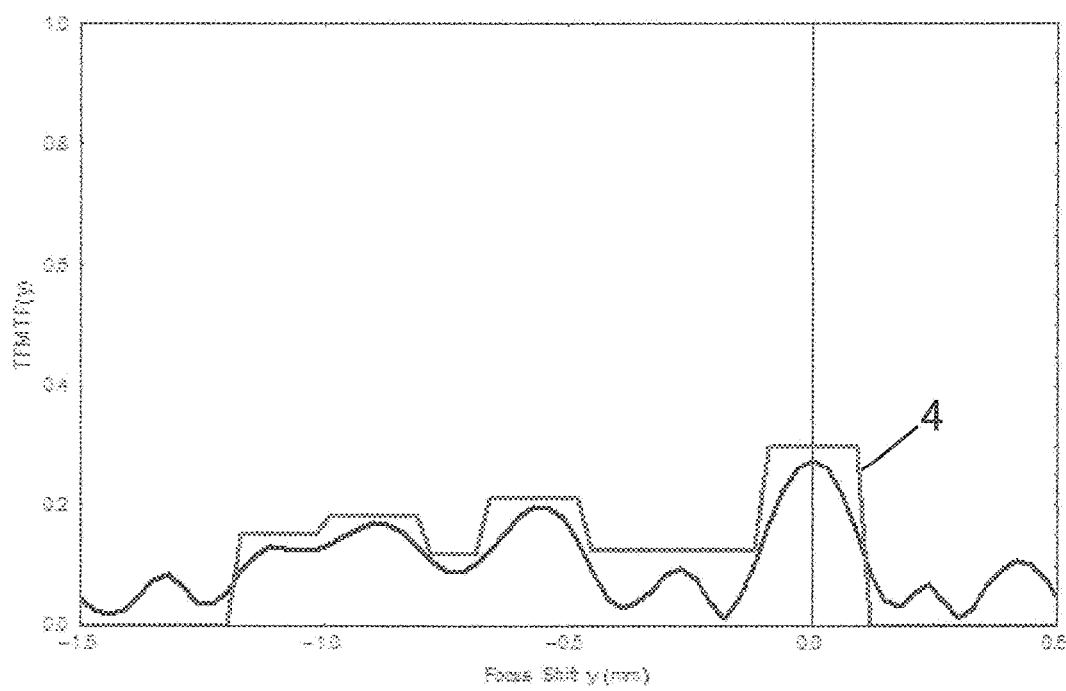
FIG. 11 describes the Through Focus Modulation Transfer Function TFMTF at 50 lp/mm and a pupillary diameter of 3.0 mm in the range −0.25 D to 3.5 D as a function of the focus shift position y on the retina expressed in mm.

In such a depth of field range, the energy distributed by the enhanced wavefront is described, as shown in FIG. 11, by the Through Focus Modulation Transfer Function TFMTF(d, y) for a pupil diameter d=3.0 mm.

In this third variant at least one surface, chosen between the front surface and the rear surface, comprises, or consists of, five concentric coaxial zones Z1, Z2, Z3, Z4, Z5 adjacent to one another and each delimited by a respective maximum radius or outer radius r1, r2, r3, r4, r5, where the coefficients $q_o, \ldots q_{11}$ of the Jacobi polynomials for defining the refractive profile of each coaxial zone, by means of a Forbes polynomial expansion up to the twelfth term, are in the following range $-0.069 \leq q_i \leq 0.115$ with $i=0, \ldots 11$.

In particular, the coefficients $q_o, \ldots q_{11}$ are in the following ranges, respectively:

$-6.38\text{E-}02 \leq q_0 \leq 1.13\text{E-}01$
$-6.89\text{E-}02 \leq q_1 \leq 5.15\text{E-}02$
$-3.23\text{E-}02 \leq q_2 \leq 4.62\text{E-}02$
$-3.14\text{E-}02 \leq q_3 \leq 1.71\text{E-}02$
$-1.01\text{E-}02 \leq q_4 \leq 1.86\text{E-}02$
$-1.19\text{E-}02 \leq q_5 \leq 6.47\text{E-}03$
$-4.40\text{E-}03 \leq q_6 \leq 8.09\text{E-}03$
$-5.75\text{E-}03 \leq q_7 \leq 3.13\text{E-}03$
$-2.31\text{E-}03 \leq q_8 \leq 4.24\text{E-}03$
$-3.22\text{E-}03 \leq q_9 \leq 1.75\text{E-}03$
$-1.36\text{E-}03 \leq q_{10} \leq 2.50\text{E-}03$
$-1.98\text{E-}03 \leq q_{11} \leq 1.08\text{E-}03$.

In a fourth variant of said first embodiment, the lens of the invention has an aspherical refractive optical design, with circular symmetry with respect to the optical axis, on one of the two surfaces which enhances the emerging wavefront W(r) so as to extensively vary the depth of field in a power range between −0.25 D and 3.5 D. In particular, the refractive profile of the front or rear surface of the lens generates the wavefront enhancement.

Figure 12:
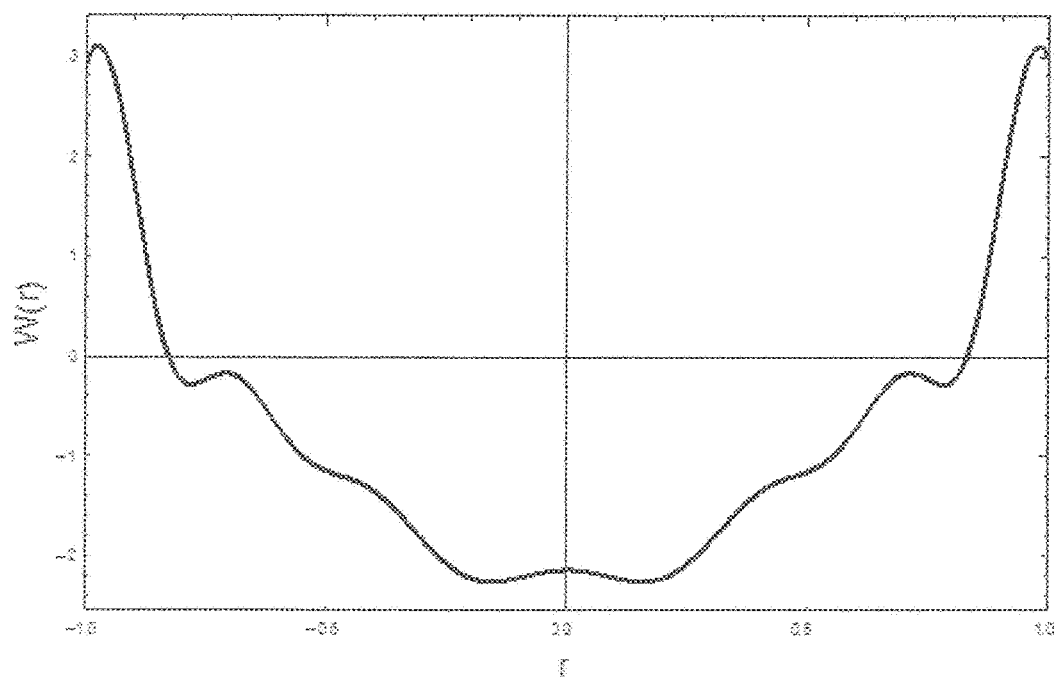
FIG. 12 depicts an enhanced wavefront in the range −0.25 D to 3.5 D.

The enhanced wavefront in this specific depth of field range has a specific shape thereof as depicted in FIG. 12.

Figure 13:
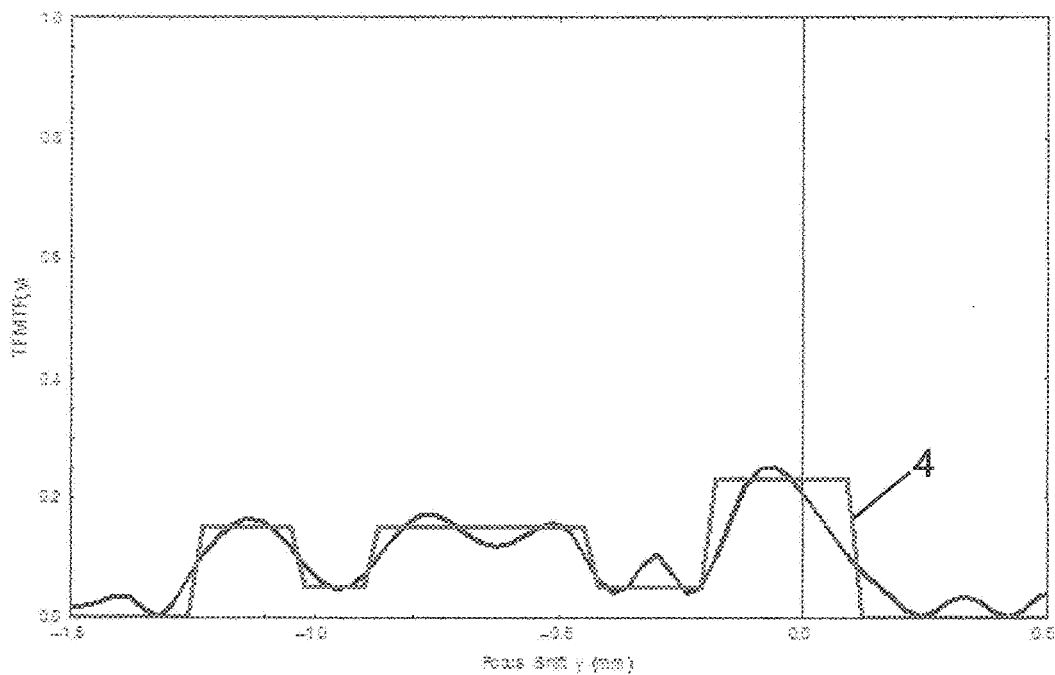
FIG. 13 depicts the Through Focus Modulation Transfer Function TFMTF at 50 lp/mm and a pupil diameter of 3.0 mm in the range −0.25 D to 3.5 D as a function of the focus shift position y on the retina expressed in mm.

In such a depth of field range, the energy distributed by the enhanced wavefront is described, as shown in FIG. 13, by the Through Focus Modulation Transfer Function TFMTF(d, y) for a pupil diameter d=3.0 mm.

In this fourth variant at least one surface, chosen between the front surface and the rear surface, comprises, or consists of, seven concentric coaxial zones Z1, Z2, Z3, Z4, Z5, Z6, Z7 adjacent to one another and each delimited by a respective maximum radius or outer radius r1, r2, r3, r4, r5, r6, r7, where the coefficients $q_o, \ldots q_{11}$ of the Jacobi polynomials for defining the refractive profile of each coaxial zone, by means of a Forbes polynomial expansion up to the twelfth term, are in the following range $-0.156 \leq q_i \leq 0.107$ with $i=0, \ldots 11$.

In particular, the coefficients $q_o, \ldots q_{11}$ are in the following ranges, respectively:

$-1.56\text{E-}01 \leq q_0 \leq 6.95\text{E-}02$
$-3.89\text{E-}02 \leq q_1 \leq 1.07\text{E-}01$
$-6.68\text{E-}02 \leq q_2 \leq 2.42\text{E-}02$
$-1.58\text{E-}02 \leq q_3 \leq 3.40\text{E-}02$
$-2.00\text{E-}02 \leq q_4 \leq 1.04\text{E-}02$
$-6.48\text{E-}03 \leq q_5 \leq 1.29\text{E-}02$
$-8.65\text{E-}03 \leq q_6 \leq 4.33\text{E-}03$
$-3.16\text{E-}03 \leq q_7 \leq 6.32\text{E-}03$
$-4.47\text{E-}03 \leq q_8 \leq 2.24\text{E-}03$
$-1.80\text{E-}03 \leq q_9 \leq 3.59\text{E-}03$
$-2.57\text{E-}03 \leq q_{10} \leq 1.29\text{E-}03$
$-1.13\text{E-}03 \leq q_{11} \leq 2.26\text{E-}03$.

In a first variant of said second embodiment at least one surface, chosen between the front surface and the rear surface, comprises, or consists of, three coaxial zones Z1, Z2, Z3 with cylindrical symmetry with respect to the optical axis, adjacent to one another and each delimited by a respective maximum radius or outer radius r1, r2, r3, where the coefficients $q_o, \ldots q_2$ of the Jacobi polynomials for defining the refractive profile of each coaxial zone Z1, Z2, Z3 are in the following range $-0.363 \leq q_i \leq 0.021$ with $i=0, 1, 2$.

In particular, the coefficients $q_o, \ldots q_2$ are in the following ranges, respectively:

$-3.63\text{E-}01 \leq q_0 \leq 7.29\text{E-}04$
$-4.71\text{E-}02 \leq q_1 \leq -1.80\text{E-}13$
$-2.60\text{E-}13 \leq q_2 \leq 2.05\text{E-}02$.

For example, in the event in which the front or rear surface of the lens comprises an aforesaid refractive profile with at least one cylindrical portion, the aforesaid zones are concentrically coaxial and the aspherical refractive profile is of cylindrical symmetry.

In other possible variants of said second embodiment at least one surface of the front surface and the rear surface comprises, or consists of, several coaxial zones in variable number from four to seven, with cylindrical symmetry with respect to the optical axis, each zone being delimited by a respective outer radius, the profile of said zones being described by the coefficients $q_o, \ldots q_{11}$ of the Jacobi polynomials.

In all the embodiments of the lens of the invention the maximum radii or outer radii of each zone are between 0.5 mm and 3 mm.

Example 1

In this example of the first variant of the first embodiment the front or rear surface of the lens consists of three coaxial zones Z1, Z2, Z3 adjacent to one another and each delimited by a respective maximum radius or outer radius r1, r2, r3, and the coefficients $q_o, \ldots q_2$ of the Jacobi polynomials for defining the refractive profile of each coaxial zone Z1, Z2, Z3 are in respective ranges. The ranges of the coefficients $q_o, \ldots q_2$ referring to zones Z1, Z2 are given in the following two tables.

|    |       | Min        | Max        |
|----|-------|------------|------------|
| Z1 | $q_0$ | −3.63E−01  | −3.58E−01  |
|    | $q_1$ | −4.71E−02  | −4.55E−02  |
|    | $q_2$ | 1.98E−02   | 2.05E−02   |

|    |       | Min        | Max        |
|----|-------|------------|------------|
| Z2 | $q_0$ | 7.29E−04   | 7.29E−04   |
|    | $q_1$ | −1.80E−13  | −1.80E−13  |
|    | $q_2$ | −2.60E−13  | −2.60E−13  |

Each zone Z1, Z2 is described by the first three terms of the Forbes series expansion.

The last zone Z3, i.e., the outermost zone, has coefficients $q_o, \ldots q_2$ of the Jacobi polynomials identically null (zero) being a simple aspherical surface, in turn described by the equation $$z(r) = \frac{cr^2}{1 + \sqrt{1 - (1+k)c^2r^2}}$$

the parameters of which are given by
c=curvature of the base sphere of the front or rear surface of the lens, and
k=conical constant of the front or rear surface.

The maximum radii or outer radii r1, r2, r3 of the corresponding concentric zones Z1, Z2, Z3 are preferably between 0.5 mm and 3.0 mm.

Preferably the outer radii of the respective zones Z1 and Z2 can be equal to r1=0.9-1.1 mm and r2=1.4-1.6 mm, while the outer radius of the outer zone Z3 is always r3=3.0 mm.

Figure 7A:
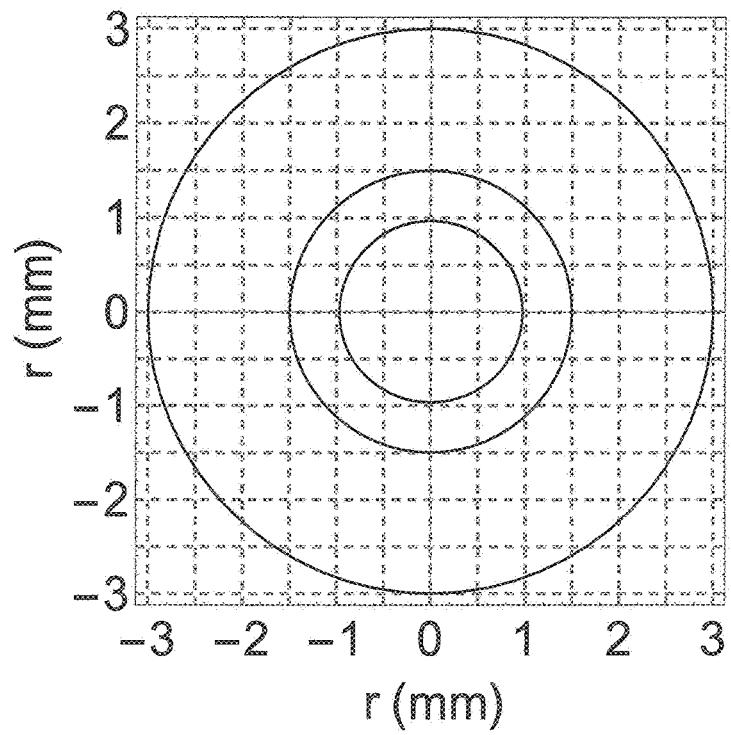
FIG. 7a depicts the zones in which a surface of a first lens according to the invention is divided.

Merely by way of example, said outer radii delimiting the respective zones can be:

r1=1.0 mm, r2=1.5 mm, r3=3.0 mm as shown in the graph in FIG. 7a.

The aforesaid three coaxial zones, namely the inner or central zone Z1, the intermediate annular zone Z2 and the outer annular zone Z3, completely fill the aperture ("clear aperture") of the optics or lens.

Advantageously, a spherical aberration is induced in the central zone Z1 and in the intermediate zone Z2 in order to obtain the target TFMTF, in accordance with the coefficient tables of the Jacobi polynomials indicated above. Instead in the outer zone Z3, no spherical aberration is introduced. In fact, in this case the outermost zone Z3 has null coefficients.

Figure 7B:
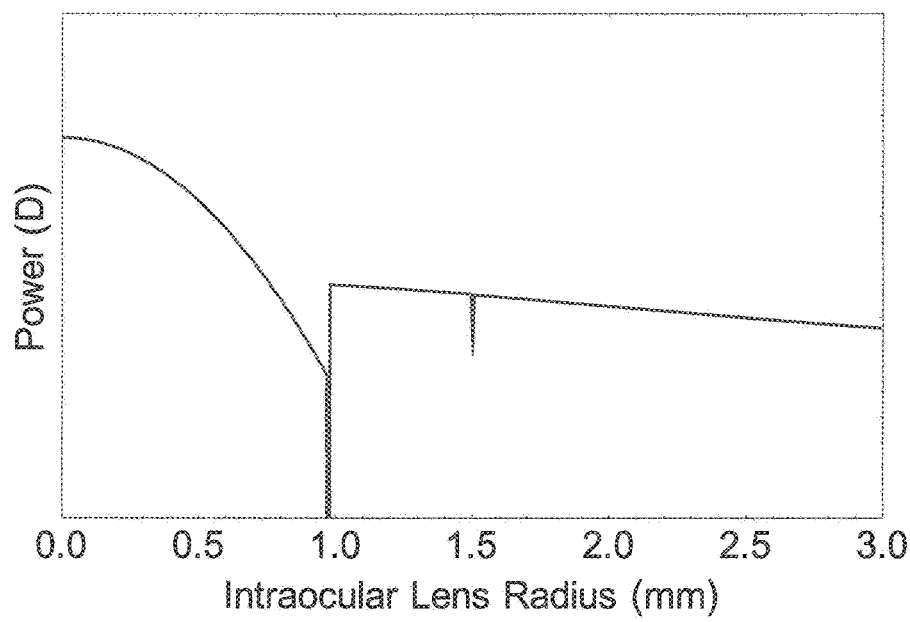
FIG. 7b depicts the trend of the optical power of said first lens as a function of the radius.

The graph in FIG. 7b shows the trend of the optical power of a first lens, the front (or rear) surface of which is divided into only three distinct concentric zones in which the power varies differently.

Figure 7C:
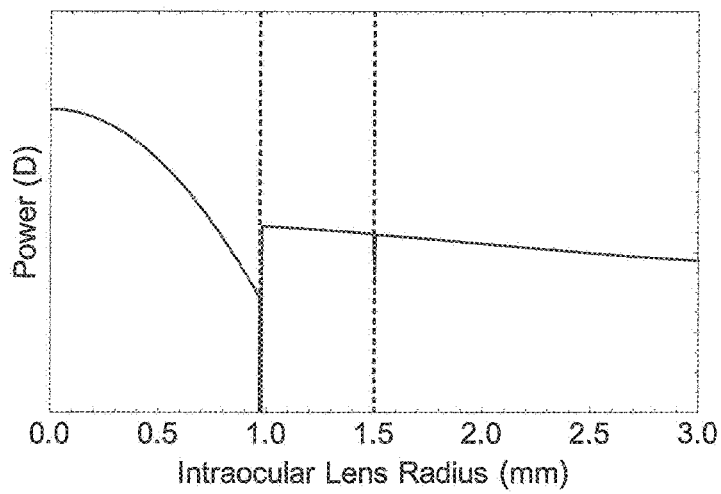
FIG. 7c depicts the graph in FIG. 7b divided into three zones.

The division into zones is shown more clearly in the graph in FIG. 7c where it can be observed that the first zone or central zone Z1 extends from the optical axis, or from the center of the surface (0.0 mm), up to a radius equal to 1.0 mm at which there is a first power discontinuity; an intermediate zone Z2 then follows which extends from a radius equal to 1.0 mm up to a radius equal to 1.5 mm at which there is an, albeit slight, second power discontinuity; finally there is a third zone or outer zone Z3 between a radius of 1.5 mm and the outer radius of the surface equal to 3.0 mm.

The central zone (extending from r=0.0 mm to r=1.0 mm) can include a plurality of optical powers which progressively vary between a first power P1 at or close to the center of the central zone and a second power P2 at or close to the edge of the central zone.

Figure 7D:
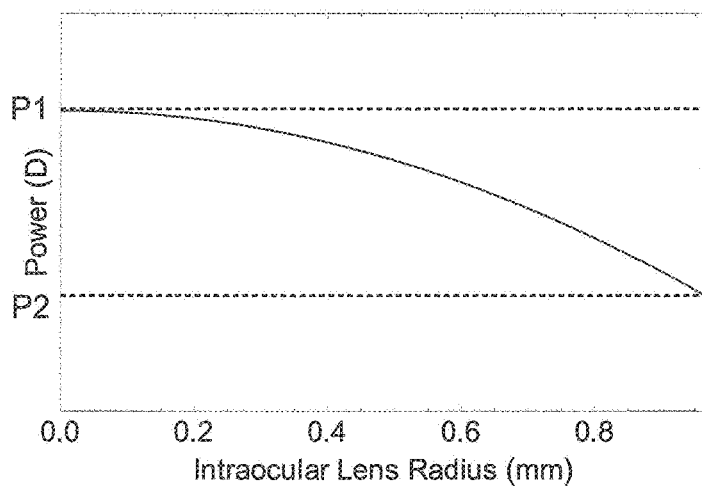
FIGS. 7d-7e depict the trend of the optical power of said first lens in the respective zones.

In the graph shown in FIG. 7d the trend of the optical power limited to only the central zone Z1 is shown: a value corresponding to far vision can be assigned to the initial power P1, or it can be assigned a greater value or, as in this case, a power adapted to provide the best visual acuity or the best MTF for intermediate near vision, i.e., for objects located at a distance of about 500 mm from the eye.

As shown in FIG. 7d, the power of the central zone (within a radius of 1.0 mm) can progressively decrease, as the radius from the optical axis increases, from the value in axis P1 to a value P2 (corresponding, for example, to the power value required to correct the far vision in proximity of the junction between the central and intermediate zone).

A negative spherical aberration is thus induced in said central zone to extend the depth of field.

The power in the intermediate zone and in the outer zone (i.e., between a radius of 1.0 mm and 3.0 mm) corresponds in this case on average to the value required to correct the far vision and gradually decreases with the increase of the radius but in a less pronounced manner (with a lower gradient) with respect to the central zone.

In the intermediate zone Z2 a negative spherical aberration is induced to extend the depth of field; while in the outer zone Z3 an aspherical monofocal profile is provided with a power so as to reduce, correct, or cancel the positive spherical aberration of the cornea.

Figure 7E:
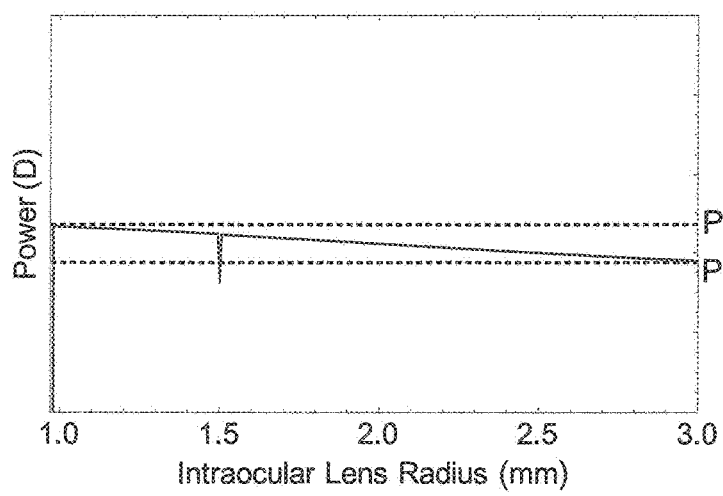

In the illustrated embodiment, the power of the central zone gradually decreases from a value P1 to a value P2 at the radius 1.0 mm; in the intermediate zone and in the outer zone (FIG. 7e) the power decreases progressively from a value P3 (greater than P2 but less than P1), at the radius 1.0 mm, to a value P4 (greater than P2 but less than P3) at the outer edge of the lens. Alternatively, the radial decrease in power within the outer zone can be such that the value P4 is less than P2. There is a power discontinuity at the passage between the intermediate zone and the outer zone, albeit slight.

Figure 1:
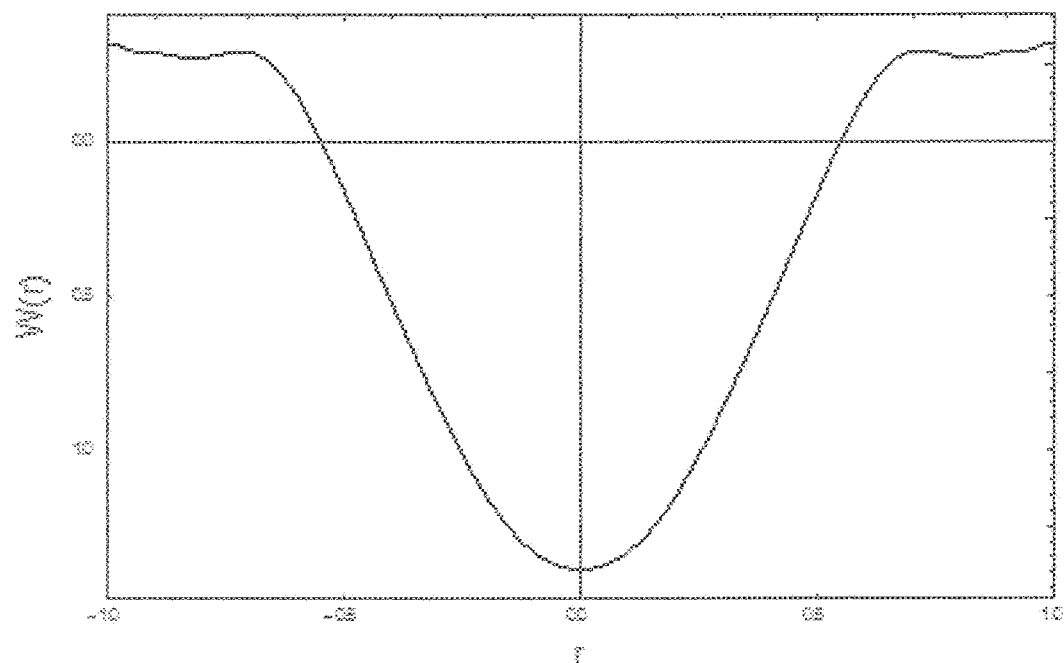
FIG. 1 depicts an enhanced wavefront in a given depth of field range.
Figure 2:
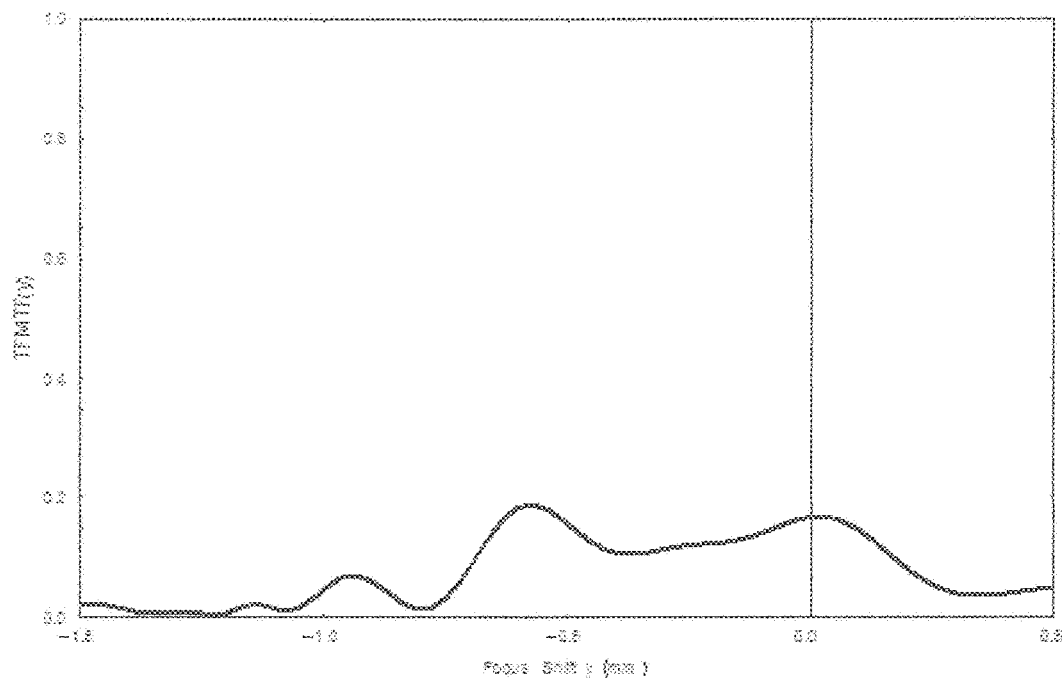
FIG. 2 depicts the Through Focus Modulation Transfer Function (TFMTF) at 50 lp/mm and a pupil diameter of 3.0 mm as a function of the focus shift position y on the retina expressed in mm.

The profile of one or both front and rear lens surfaces can be configured to provide a more complex radial power variation, with respect to that shown in FIG. 1, in order to provide higher focusing depth performance for different pupil diameters.

Example 2

In this example of the second variant of the first embodiment, the front or rear surface of the lens consists of five coaxial zones Z1, Z2, Z3, Z4, Z5, adjacent to one another and each delimited by a respective maximum radius or outer radius r1, r2, r3, r4, r5, and the coefficients $q_o, \ldots q_{11}$ of the Jacobi polynomials for defining the refractive profile of each coaxial zone Z1, Z2, Z3, Z4, Z5 are in respective ranges.

The ranges of the coefficients $q_o, \ldots q_{11}$ referring to the zones Z1, Z2, Z3, Z4 are given in the following four tables.

|    |     | Min       | Max       |
|----|-----|-----------|-----------|
| Z1 | q0  | 3.47E–03  | 4.31E–03  |
|    | q1  | –2.57E–03 | –1.79E–03 |
|    | q2  | 1.25E–03  | 1.47E–03  |
|    | q3  | –8.29E–04 | –4.15E–05 |
|    | q4  | 1.60E–04  | 1.82E–04  |
|    | q5  | –1.28E–04 | –6.04E–05 |
|    | q6  | 4.11E–05  | 8.68E–05  |
|    | q7  | –6.17E–05 | –2.92E–05 |
|    | q8  | 2.15E–05  | 4.55E–05  |
|    | q9  | –3.45E–05 | –1.63E–05 |
|    | q10 | 1.27E–05  | 2.68E–05  |
|    | q11 | –2.12E–05 | –1.00E–05 |

|    |     | Min       | Max       |
|----|-----|-----------|-----------|
| Z2 | q0  | –5.58E–02 | –2.22E–02 |
|    | q1  | 1.49E–02  | 3.63E–02  |
|    | q2  | –1.87E–02 | –7.59E–03 |
|    | q3  | 4.65E–03  | 9.45E–03  |
|    | q4  | –5.48E–03 | –2.47E–03 |
|    | q5  | 1.90E–03  | 3.81E–03  |
|    | q6  | –2.59E–03 | –1.29E–03 |
|    | q7  | 9.19E–04  | 1.84E–03  |
|    | q8  | –1.36E–03 | –6.77E–04 |
|    | q9  | 5.14E–04  | 1.03E–03  |
|    | q10 | –8.00E–04 | –3.99E–04 |
|    | q11 | 3.16E–04  | 6.34E–04  |

|    |     | Min       | Max       |
|----|-----|-----------|-----------|
| Z3 | q0  | 5.94E−01  | 6.97E−01  |
|    | q1  | −4.22E−01 | −3.69E−01 |
|    | q2  | 2.16E−01  | 2.37E−01  |
|    | q3  | −1.24E−01 | −1.16E−01 |
|    | q4  | 6.37E−02  | 6.95E−02  |
|    | q5  | −4.42E−02 | −4.06E−02 |
|    | q6  | 2.76E−02  | 3.01E−02  |
|    | q7  | −2.14E−02 | −1.96E−02 |
|    | q8  | 1.45E−02  | 1.58E−02  |
|    | q9  | −1.20E−02 | −1.10E−02 |
|    | q10 | 8.52E−03  | 9.28E−03  |
|    | q11 | −7.35E−03 | −6.75E−03 |

|    |     | Min       | Max       |
|----|-----|-----------|-----------|
| Z4 | q0  | 3.05E−03  | 4.41E−03  |
|    | q1  | −3.64E−03 | −2.62E−03 |
|    | q2  | 1.12E−03  | 1.56E−03  |
|    | q3  | −8.17E−04 | −5.88E−04 |
|    | q4  | 3.47E−04  | 4.83E−04  |
|    | q5  | −3.09E−04 | −2.23E−04 |
|    | q6  | 1.51E−04  | 2.10E−04  |
|    | q7  | −1.50E−04 | −1.08E−04 |
|    | q8  | 7.94E−05  | 1.10E−04  |
|    | q9  | −8.36E−05 | −6.02E−05 |
|    | q10 | 4.67E−05  | 6.49E−05  |
|    | q11 | −5.14E−05 | −3.70E−05 |

Therefore, each zone Z1, Z2, Z3, Z4 is described by the first twelve terms of the Forbes series expansion.

The last zone Z5, i.e., the outermost zone, has coefficients $q_0, \ldots q_{11}$ of the Jacobi polynomials identically null being a simple aspherical surface, in turn described by the equation $$z(r) = \frac{cr^2}{1 + \sqrt{1 - (1+k)c^2 r^2}}$$

the parameters of which are given by
c=curvature of the base sphere of the front or rear surface of the lens, and
k=conical constant of the front or rear surface.

The maximum radii or outer radii r1, r2, r3, r4, r5 of the corresponding concentric zones Z1, Z2, Z3, Z4, Z5 are preferably between 1.0 mm and 3.0 mm.

Preferably the outer radii of the zones Z1, Z2, Z3 and Z4 can be equal to r1=0.9-1.1 mm, r2=1.25-1.35 mm, r3=1.4-1.6 mm, and r4=2.15-2.35 mm, respectively, while the outer radius of the outer zone Z5 is always r3=3.0 mm.

Figure 9A:
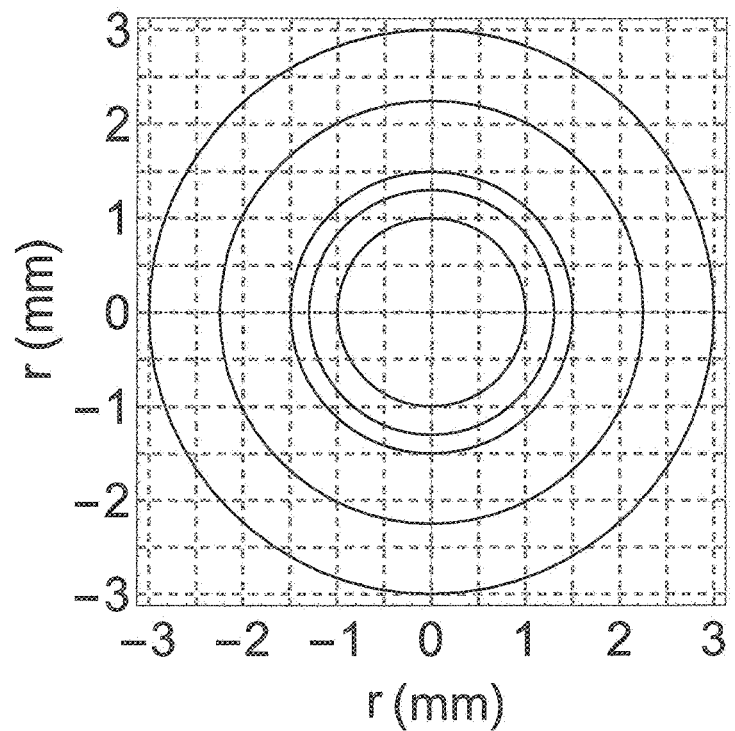
FIG. 9a depicts the zones in which a surface of a second lens according to the invention is divided.

Merely by way of example, said maximum radii delimiting the respective zones can be:
r1=1.0 mm, r2=1.3 mm, r3=1.5 mm, r4=2.25 mm, and r5=3.0 mm, as shown in the graph in FIG. 9a.

The aforesaid five coaxial zones, i.e., the inner or central zone Z1, the intermediate annular zones Z2, Z3, Z4 and the outer annular zone Z5, completely fill the aperture ("clear aperture") of the optics or lens.

Advantageously, a spherical aberration is induced in the central zone Z1 and in the intermediate zones Z2, Z3 and Z4 in order to obtain the target TFMTF, in accordance with the coefficient tables of the Jacobi polynomials indicated above. Instead in the outer zone Z5, no spherical aberration is introduced. In fact, in this case the outermost zone Z5 has null coefficients.

Figure 9B:
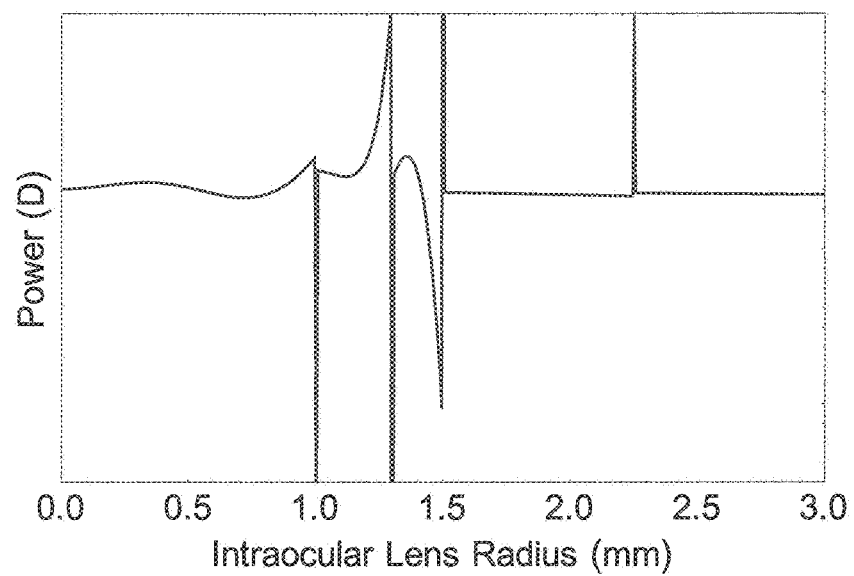
FIG. 9b depicts the trend of the optical power of said second lens as a function of the radius.

In the graph in FIG. 9b the trend of the optical power of a second lens is shown, in which it is desired to improve near vision and induce an improvement of the vision over intermediate depth of field (approximately 1.0 m away from the patient's eye). In this second example, the power variation in a single zone is more pronounced and simultaneously contributes to improving near and far vision so as to maintain the vision quality uniform and independent of the pupil diameter for variable values between 2.5 mm and 4.5 mm.

Figure 9C:
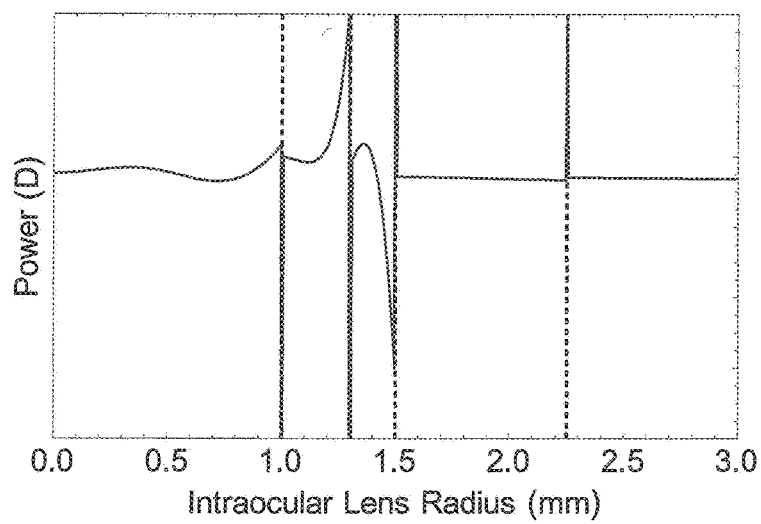
FIG. 9c depicts the graph in FIG. 9b divided into five zones.

The division into zones is shown more clearly in the graph in FIG. 9c where it is observed that the first zone or central zone Z1 extends from the center of the lens up to a radius of 1.0 mm at which there is a first power discontinuity. A second zone or first intermediate zone Z2 extends from a radius of 1.0 mm to a radius of 1.3 mm at which there is a second power discontinuity. A third zone or second intermediate zone Z3 extends from a radius of 1.3 mm to a radius of 1.5 mm at which there is a third power discontinuity. A fourth zone or third intermediate zone Z4 extends from a radius of 1.5 mm to a radius of 2.25 mm at which there is a fourth power discontinuity. A fifth zone or outer zone Z5 extends from a radius of 2.25 mm to the outer radius of the surface equal to 3.0 mm.

Also in this case, the zones in which the lens surface is divided include a plurality of optical powers which progressively vary between a power at or close to the center of the central zone and a different power at or close to the edge of the lens, but in a more complex manner than that exemplified in the previous lens.

In more detail, the central zone Z1 (extending from r=0.0 mm to r=1.0 mm) includes optical powers (see FIG. 9d) which continuously vary between a first power P1 at or close to the center of the lens and a second power P4 at or close to the edge of the central zone.

Figure 9D:
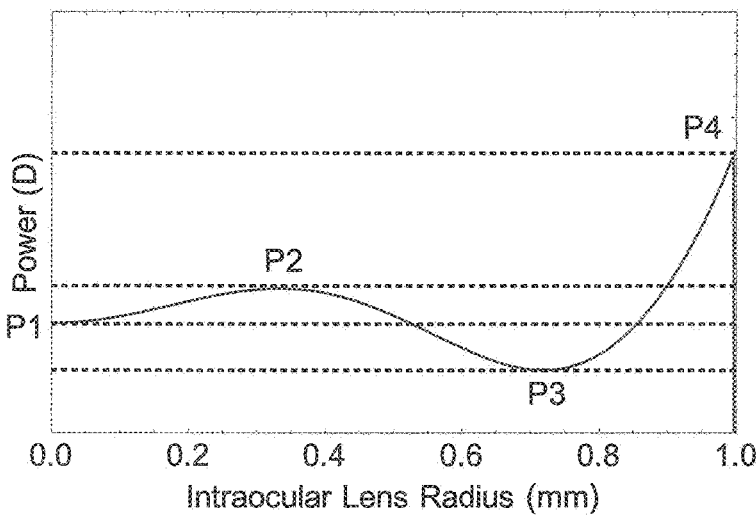
FIGS. 9d-9i depict the trend of the optical power of said second lens in the respective zones.

In the graph shown in FIG. 9d, the initial power P1 can be configured, as in the case previously illustrated, to improve far vision, or it can assume a value greater than that required for far vision, for example a power adapted to determine the best visual acuity or the best MTF for intermediate near vision for objects located at a distance of about 1.0 m from the patient's eye.

In more detail, in the graph in FIG. 9d the power of the inner or central zone Z1, up to a radius of 1.0 mm, is configured to improve far vision and progressively increases from the center of the lens to a maximum value P2, for example at a radius of about 0.30-0.35 mm, in presence of a positive spherical aberration in a first central sub-zone (for example, to improve near vision at 5 m from the eye). Continuing towards the outside of the central zone, the power gradually decreases, in presence of a negative spherical aberration in a second central sub-zone up to a minimum value P3, for example at a radius equal to about 0.70-0.75 mm; beyond this radius, the power increases again up to an end value P4 in presence of a positive spherical aberration in a third central sub-zone: thereby the central zone is effectively divided into several sub-zones in which the power variation alternately contributes to near and far vision so that the patient has a vision quality which is more independent of the pupil diameter.

Figure 9E:
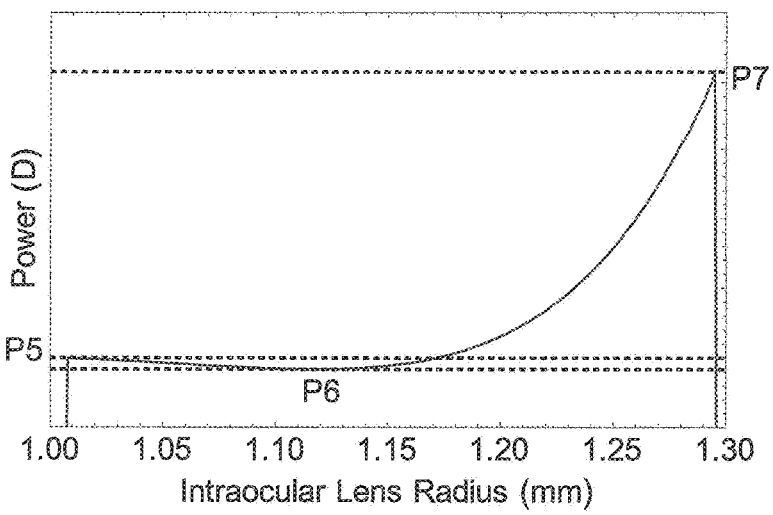

The power in the first intermediate zone Z2 (FIG. 9e), following the central zone (i.e., the zone between a radius of 1.0 mm and 1.3 mm), first decreases slightly from a value P5 to a minimum value P6 and then progressively increases with the increase of the radius from the optical axis up to the end value P7: thereby, this intermediate zone Z2 induces a negative spherical aberration in the initial part thereof, for example up to a radius of about 1.12-1.13 mm, and then a positive spherical aberration in the final part thereof close to the outer edge of the zone Z2 itself. However, since the values P5 and P6 are between P3 and P4 and the power value P7 is greater than the average power value of the central zone Z1, this intermediate zone Z2 overall induces a greater power variation than that present in the center of the lens and favors vision for objects positioned at an intermediate distance (1.0 m) and near (about 0.5 m) to the patient.

Figure 9F:
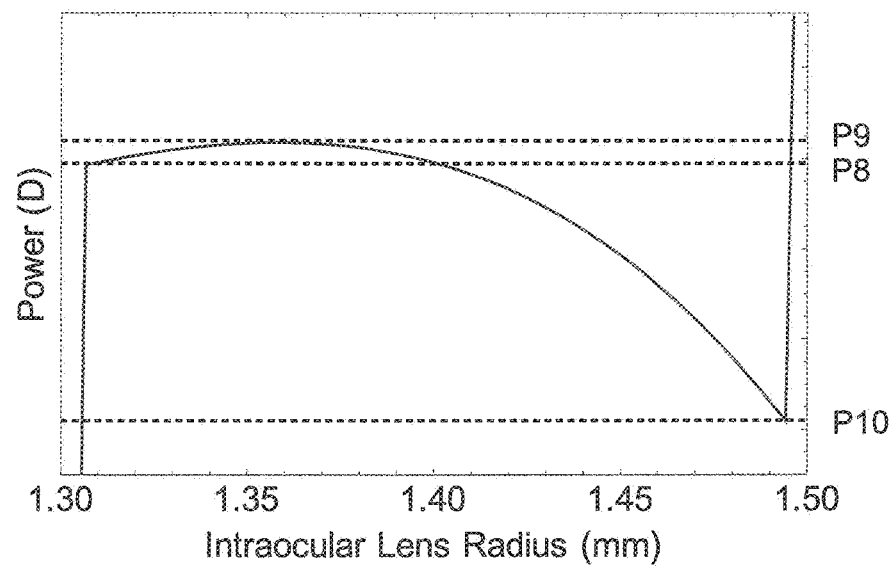

Moving farther away from the center of the lens, in the second intermediate zone Z3 (FIG. 9f), between a radius of 1.3 mm and 1.5 mm, the optical power first increases slightly from a value P8 to a maximum value P9 and then gradually decreases with the increase of the radius from the optical axis up to the end value P10: thereby, this intermediate zone Z3 induces a positive spherical aberration in the initial part thereof, for example up to a radius of about 1.36-1.37 mm, and then a negative spherical aberration in the final part thereof close to the outer radius thereof. However, since the power values P8 and P9 are between P3 and P4 and the value P10 is lower than the average power value of the central zone Z1, this intermediate zone Z3 favors in the innermost part thereof the vision for objects positioned at an intermediate distance and near to the patient and, in the outermost part thereof, the far vision. Therefore, the intermediate zone Z3 has opposite behavior to that of the previous zone Z2 and contributes to maintaining vision in the patient independent of the pupil diameter.

Figure 9G:
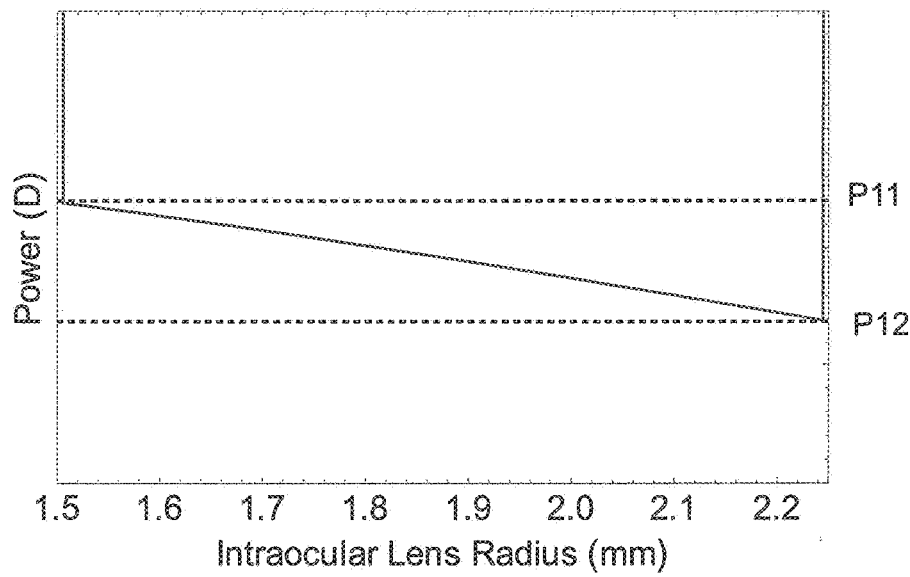

In the third intermediate zone Z4 (FIG. 9g), between a radius of 1.5 mm and a radius of 2.25 mm, the power gradually decreases from a value P11 to a value P12 with the increase of the radius from the optical axis, in presence of a negative spherical aberration close to the outer edge thereof, partially compensating for the positive aberration of the cornea. Furthermore, the average power value between P11 and P12 is substantially equal to the average power value of the central zone Z1, with a tolerance of ±0.3 D. The effect is to help further improve far vision.

Figure 9H:
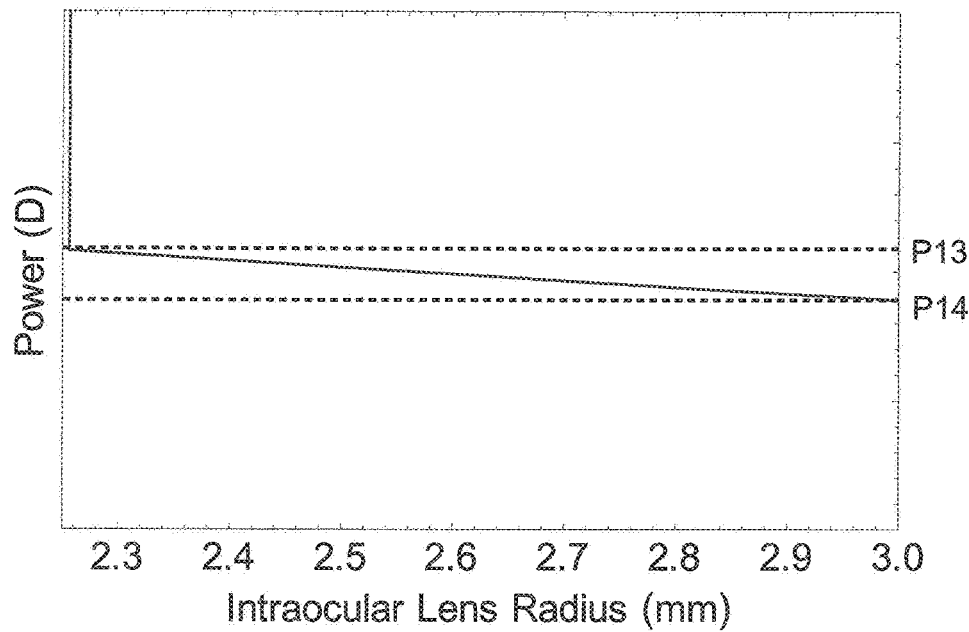
Figure 9I:
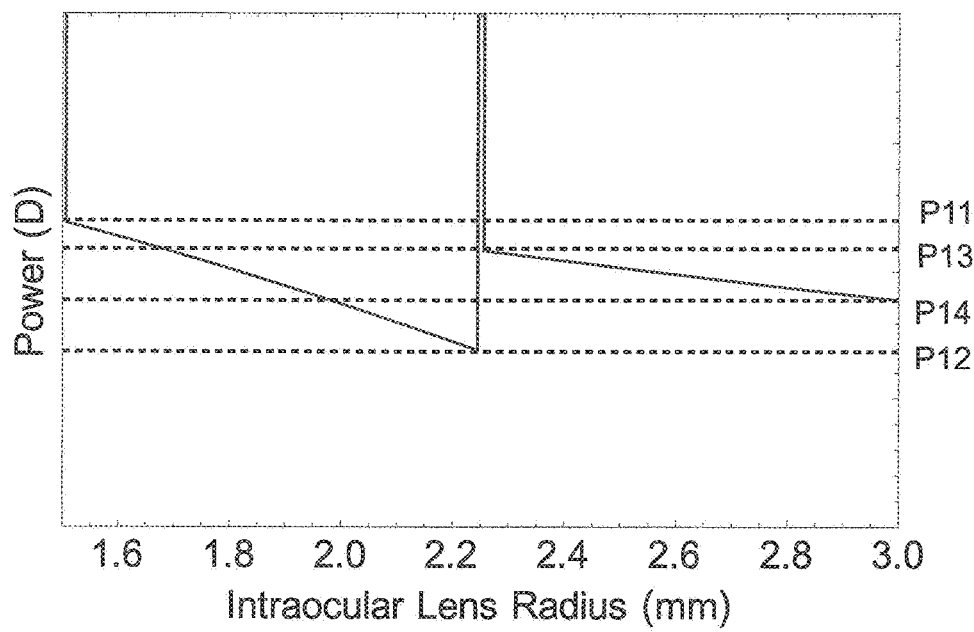

In the outer zone Z5 (FIG. 9h), between a radius of 2.25 mm and a radius of 3.0 mm, an aspherical monofocal profile is provided with a power such as to reduce, correct or cancel the positive spherical aberration of the cornea. The power progressively decreases from a value P13 to a value P14 as the radius from the optical axis increases, at least partially compensating for the positive spherical aberration of the cornea. As shown in FIG. 9i, the powers P13 and P14 are in the range between P11 and P12: this allows partially compensating for the positive contribution of the spherical corneal aberration in order not to completely cancel the near vision ability for pupil diameters greater than 4.5 mm. In a further example, zonal power variations can be induced to further improve the performance of the intraocular lens for extreme near vision (330 mm-350 mm).

Example 3

In this example of the third variant of the first embodiment, the front or rear surface of the lens has five coaxial zones Z1, Z2, Z3, Z4, Z5, adjacent to one another and each delimited by a respective maximum radius or outer radius r1, r2, r3, r4, r5, and the coefficients $q_o, \ldots q_{11}$ of the Jacobi polynomials for defining the refractive profile of each coaxial zone Z1, Z2, Z3, Z4, Z5 are in respective ranges. The ranges of the coefficients $q_o, \ldots q_{11}$ referring to the zones Z1, Z2, Z3, Z4 are given in the following four tables.

|    |     | Min       | Max       |
|----|-----|-----------|-----------|
| Z1 | q0  | 4.07E-03  | 4.23E-03  |
|    | q1  | -1.09E-03 | -7.00E-04 |
|    | q2  | 6.37E-04  | 7.64E-04  |
|    | q3  | -4.00E-04 | -3.34E-04 |
|    | q4  | 1.97E-04  | 2.36E-04  |
|    | q5  | -1.52E-04 | -1.26E-04 |
|    | q6  | 8.59E-05  | 1.03E-04  |
|    | q7  | -7.33E-05 | -6.11E-05 |
|    | q8  | 4.50E-05  | 5.40E-05  |
|    | q9  | -4.09E-05 | -3.42E-05 |
|    | q10 | 2.65E-05  | 3.18E-05  |
|    | q11 | -2.52E-05 | -2.10E-05 |

|    |     | Min       | Max       |
|----|-----|-----------|-----------|
| Z2 | q0  | 1.11E-02  | 1.61E-02  |
|    | q1  | -8.73E-03 | -5.50E-03 |
|    | q2  | 1.64E-03  | 3.39E-03  |
|    | q3  | -1.78E-03 | -8.56E-04 |
|    | q4  | 5.06E-04  | 1.05E-03  |
|    | q5  | -6.73E-04 | -3.24E-04 |
|    | q6  | 2.21E-04  | 4.58E-04  |
|    | q7  | -3.26E-04 | -1.57E-04 |
|    | q8  | 1.16E-04  | 2.40E-04  |
|    | q9  | -1.82E-04 | -8.77E-05 |
|    | q10 | 6.81E-05  | 1.41E-04  |
|    | q11 | -1.12E-04 | -5.39E-05 |

|    |     | Min       | Max       |
|----|-----|-----------|-----------|
| Z3 | q0  | 9.34E-02  | 1.10E-01  |
|    | q1  | -6.89E-02 | -5.81E-02 |
|    | q2  | 3.67E-02  | 4.54E-02  |
|    | q3  | -2.38E-02 | -1.92E-02 |
|    | q4  | 1.13E-02  | 1.41E-02  |
|    | q5  | -9.02E-03 | -7.28E-03 |
|    | q6  | 4.95E-03  | 6.13E-03  |
|    | q7  | -4.36E-03 | -3.52E-03 |
|    | q8  | 2.59E-03  | 3.21E-03  |
|    | q9  | -2.44E-03 | -1.97E-03 |
|    | q10 | 1.53E-03  | 1.89E-03  |
|    | q11 | -1.50E-03 | -1.21E-03 |

|    |     | Min       | Max       |
|----|-----|-----------|-----------|
| Z4 | q0  | -6.07E-02 | 1.13E-01  |
|    | q1  | -6.45E-02 | 5.15E-02  |
|    | q2  | -3.23E-02 | 4.62E-02  |
|    | q3  | -3.14E-02 | 1.71E-02  |
|    | q4  | -1.01E-02 | 1.86E-02  |
|    | q5  | -1.19E-02 | 6.47E-03  |
|    | q6  | -4.40E-03 | 8.09E-03  |
|    | q7  | -5.75E-03 | 3.13E-03  |
|    | q8  | -2.31E-03 | 4.24E-03  |
|    | q9  | -3.22E-03 | 1.75E-03  |
|    | q10 | -1.36E-03 | 2.50E-03  |
|    | q11 | -1.98E-03 | 1.08E-03  |

Therefore, each zone Z1, Z2, Z3, Z4 is described by the first twelve terms of the Forbes series expansion.

The last zone Z5, i.e., the outermost zone, has coefficients $q_o, \ldots q_{11}$ of the Jacobi polynomials identically null being a simple aspherical surface, in turn described by the equation $$z(r) = \frac{cr^2}{1 + \sqrt{1 - (1+k)c^2r^2}}$$

the parameters of which are given by c=curvature of the base sphere of the front or rear surface of the lens, and k=conical constant of the front or rear surface.

The maximum radii or outer radii r1, r2, r3, r4, r5 of the corresponding concentric zones Z1, Z2, Z3, Z4, Z5 are preferably between 0.5 mm and 3.0 mm.

Preferably the outer radii of the respective zones Z1, Z2, Z3 and Z4 can be equal to r1=0.4-0.5 mm, r2=0.7-0.9 mm, r3=1.25-1.45 mm, and r4=2.15-2.35 mm, while the outer radius of the outer zone Z5 is always r3=3.0 mm.

Figure 11A:
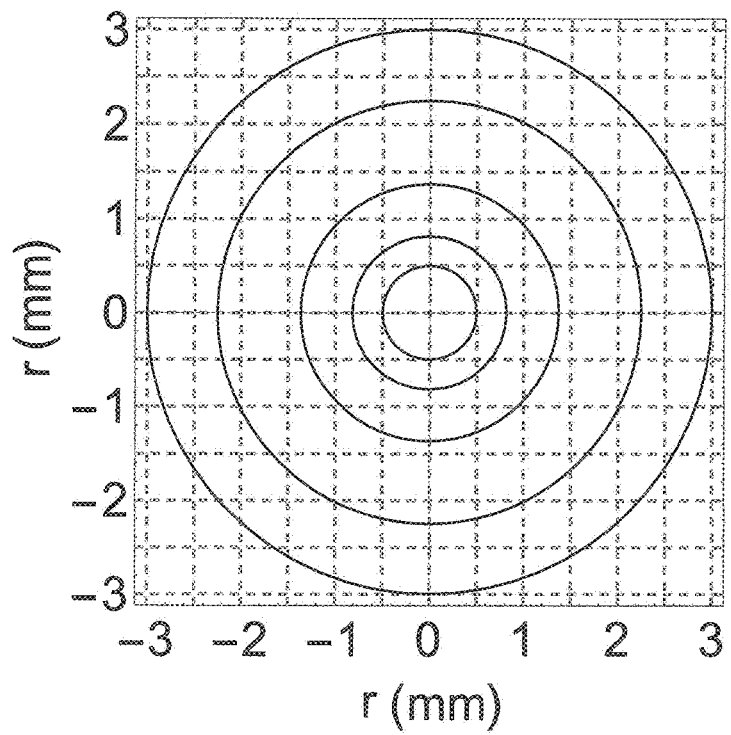
FIG. 11a depicts the zones in which a surface of a third lens according to the invention is divided.

Merely by way of example, said maximum radii delimiting the respective zones can be:

r1=0.5 mm, r2=0.82 mm, r3=1.37 mm, r4=2.25 mm, and r5=3.0 mm, as shown in the graph in FIG. 11a.

The aforesaid five coaxial zones, i.e., the inner or central zone Z1, the intermediate annular zones Z2, Z3, Z4 and the outer annular zone Z5, completely fill the aperture ("clear aperture") of the optics or lens.

Advantageously, a spherical aberration is induced in the central zone Z1 and in the intermediate zones Z2, Z3 and Z4 in order to obtain the target TFMTF, in accordance with the coefficient tables of the Jacobi polynomials indicated above. Instead in the outer zone Z5, no spherical aberration is introduced. In fact, in this case the outermost zone Z5 has null coefficients.

Figure 11B:
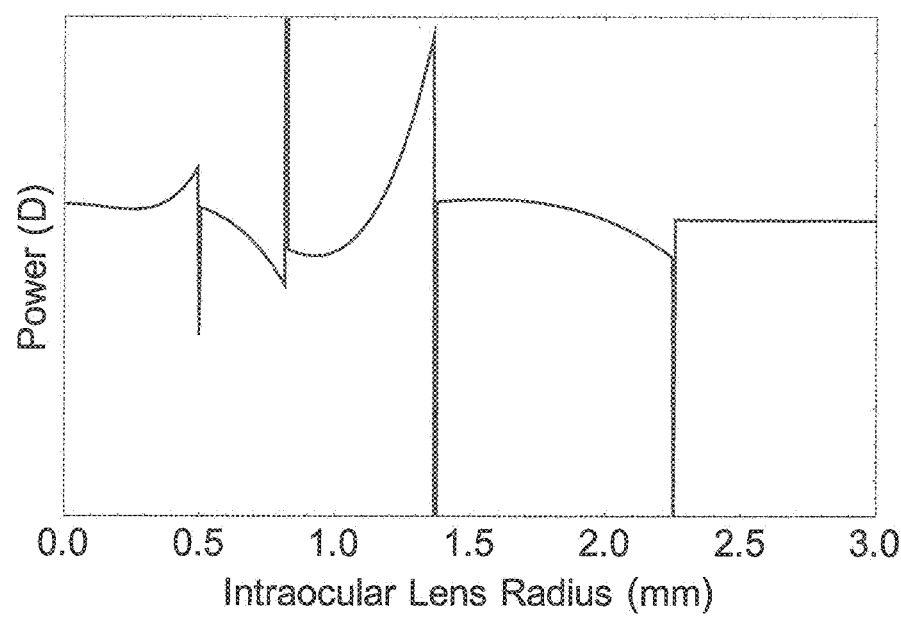
FIG. 11b depicts the trend of the optical power of said third lens as a function of the radius.

The graph in FIG. 11b shows the power trend of a lens referred to this example 3. As in example 2, also in this case the variation of power in a single zone will be more pronounced with respect to example 1 to continuously provide the best visual acuity or the best MTF for both far vision and very near vision, i.e., for objects located at a distance of less than 500 mm from the eye, and independent of the pupil diameter which can assume variable values between 2.5 mm and 4.5 mm.

Figure 11C:
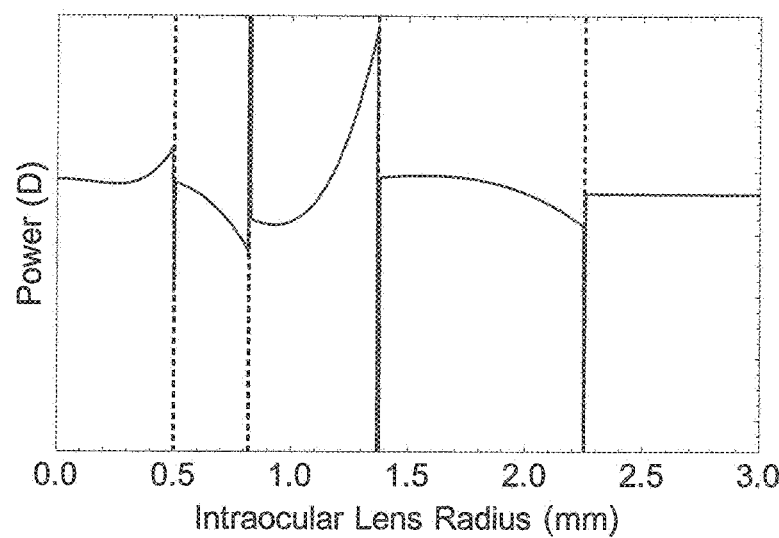
FIG. 11c depicts the graph in FIG. 11b divided into five zones.

The division into zones is shown more clearly in the graph in FIG. 11c where it is observed that the first zone or central zone Z1 extends from the center of the lens up to a radius of 0.5 mm at which there is a first power discontinuity. A second zone or first intermediate zone Z2 extends from a radius of 0.5 mm to a radius of 0.82 mm at which there is a second power discontinuity. A third zone or second intermediate zone Z3 extends from a radius of 0.82 mm to a radius of 1.37 mm at which there is a third power discontinuity. A fourth zone or third intermediate zone Z4 extends from a radius of 1.37 mm to a radius of 2.25 mm at which there is a fourth power discontinuity. A fifth zone or outer zone Z5 extends from a radius of 2.25 mm to the outer radius of 3.0 mm.

In more detail, the central zone Z1 (extending from r=0.0 mm to r=0.5 mm) includes optical powers (see FIG. 11d) which continuously vary between a power P1 at or close to the center of the lens and a power P3 at or close to the edge of the central zone.

Figure 11D:
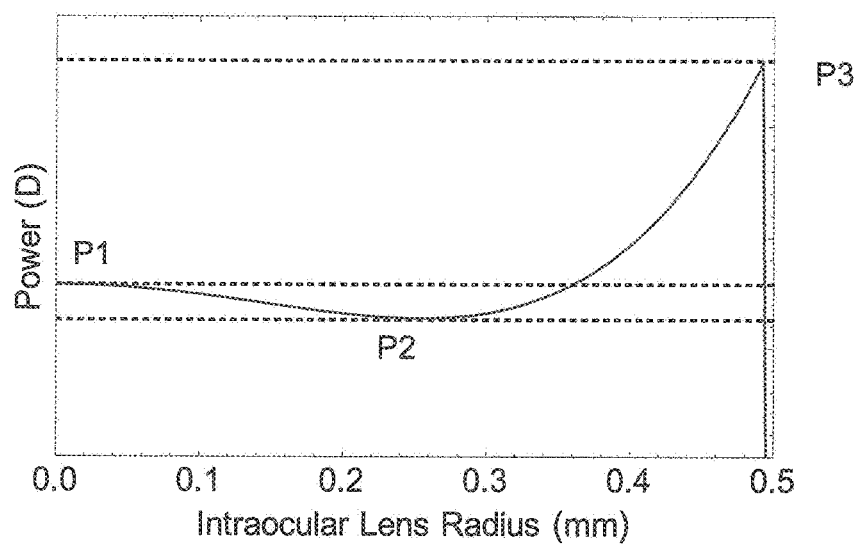
FIGS. 11d-11h depict the trend of the optical power of said third lens in the respective zones.

In the graph in FIG. 11d, the initial power P1 can be configured to improve far vision, or it can assume a value greater than that required for far vision, for example a power adapted to determine the best visual acuity or the best MTF for near vision of objects located at a distance of about 1.0 m from the patient's eye or for even nearer vision (about 300 mm).

In more detail, in the graph in FIG. 11d the power of the inner or central zone Z1, up to a radius of 0.5 mm, is configured to improve near vision (at about 1.0 m) and progressively decreases from the center of the lens from the value P1 to a minimum value P2, for example at a radius of about 0.22-0.26 mm, in presence of a slightly negative spherical aberration in a first central sub-zone (for example, to help improve far vision). Continuing towards the outside of the central zone, the power gradually increases, in presence of a positive spherical aberration in a second central sub-zone up to a maximum value P3 at a radius of about 0.5 mm: thereby the central zone is effectively divided into two sub-zones in which the power variation alternatively contributes to far vision and near vision so that the patient has a vision quality which is more independent of the diameter.

Figure 11E:
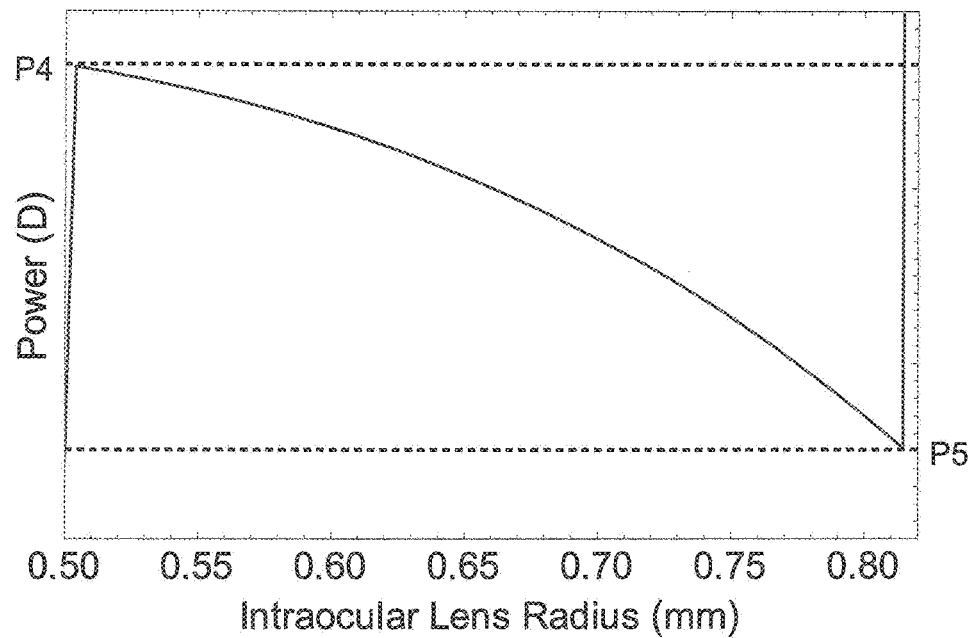

The power in the first intermediate zone Z2 (FIG. 11e), following the central one (i.e., the zone between a radius of 0.5 mm and 0.82 mm), progressively decreases from a power value P4 to a power value P5 in presence of a negative spherical aberration in this intermediate zone Z2. However, since the values P4 and P5 are lower than P2, this zone overall induces a change in power such as to favor vision for objects positioned at a distance from the patient between the intermediate (1.0 m) and far field.

Figure 11F:
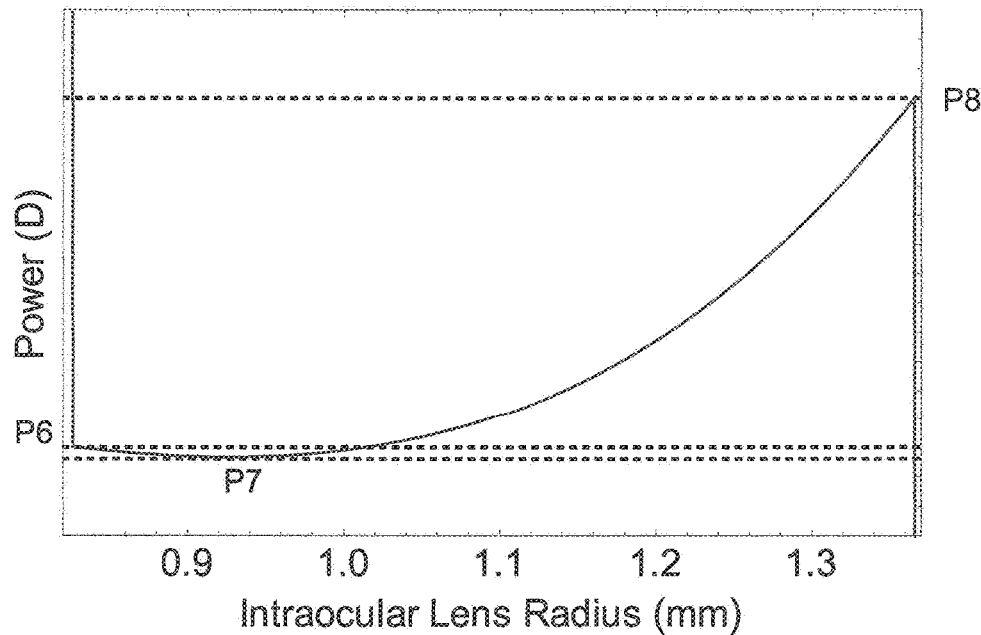

Moving farther away from the center of the lens, in the second intermediate zone Z3 (FIG. 11f), between a radius of 0.82 mm and 1.37 mm, the optical power first decreases slightly from a value P6 to a minimum value P7 and then progressively increases with the increase of the radius from the optical axis up to the extreme value P8. In fact, this intermediate zone Z3 provides a slight negative spherical aberration in the initial part thereof, for example up to a radius of about 0.94 mm, and a more pronounced positive spherical aberration in the final part thereof close to the outer edge of the zone Z3, i.e., close to the outer radius thereof. The power values between P6 and P7 contribute to an improved far vision, while the value P8 contributes to an improved near vision. Preferably, the power values P6 and P7 are between P4 and P5 and the value P8 is greater than the average power value of the central zone. Therefore, this intermediate zone Z3 overall has opposite behavior to that of the previous zone Z2 and contributes to maintaining the best visual acuity or the best MTF for both far vision and near vision independently of pupil diameter.

Figure 11G:
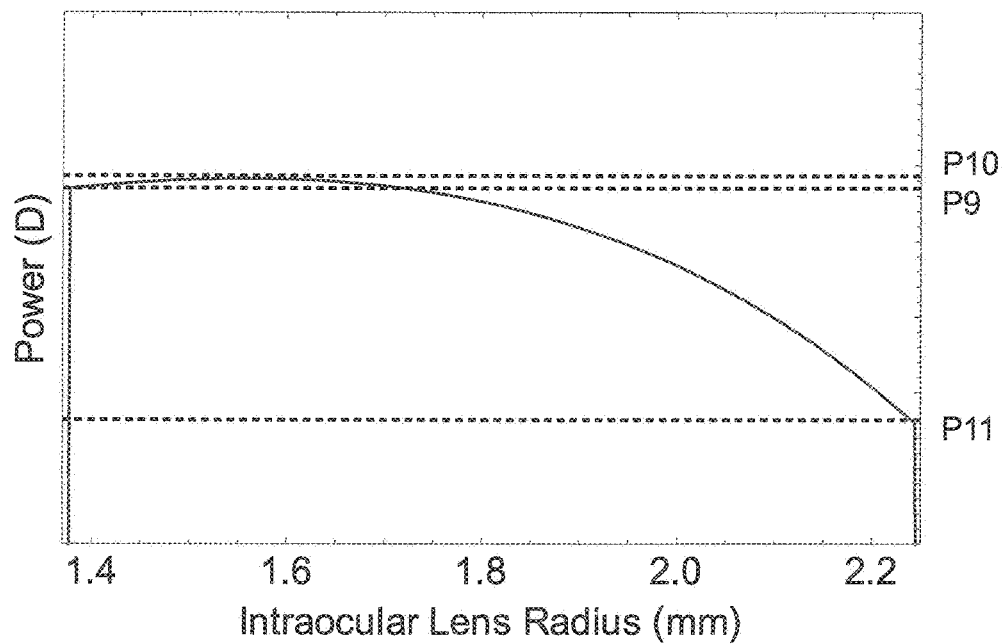

In the third intermediate zone Z4 (FIG. 11g), between a radius of 1.37 mm and a radius of 2.25 mm, the power first slightly increases from a value P9 to a value P10 and then progressively decreases with the increase of the radius from the optical axis up to a value P11, in presence of an overall negative spherical aberration in this zone Z4 close to the outer edge thereof; in this case the power values P9 and P10 contribute more to improving vision quality in the near intermediate field (1.0 m) while the negative end value, P11, contributes to improving far vision. The overall effect of this zone is to simultaneously contribute to the improvement of intermediate vision (1.0 m) and far vision.

Figure 11H:
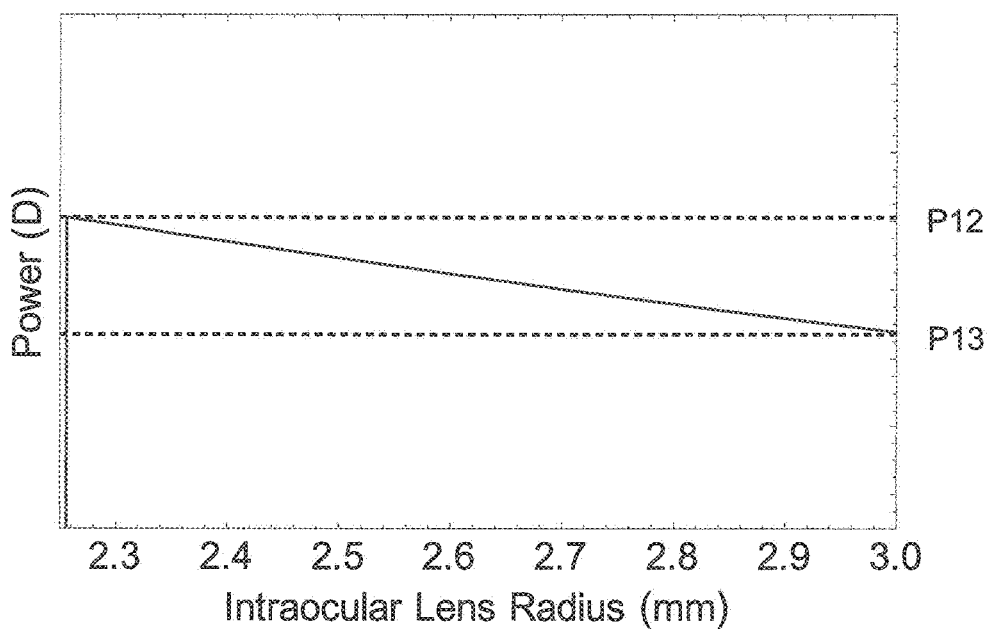

In the outer zone Z5 (FIG. 11h), between a radius of 2.25 mm and a radius of 3.0 mm, an aspherical monofocal profile is provided with a power profile such as to reduce, correct or cancel the positive spherical aberration of the cornea. The power gradually decreases from a value P12 to a value P13 as the radius from the optical axis increases, so as to partially compensate the positive spherical aberration of the cornea. The average power value between P12 and P13 substantially corresponds to the average power value of the central zone Z1, with a tolerance of ±0.3 D.

In a further example, zonal power variations can be induced to improve the performance of the intraocular lens for extreme near vision (330 mm-350 mm) by dividing the surface of the lens into a greater number of zones, such as seven.

Example 4

In this example of the fourth variant of the first embodiment, the front or rear surface of the lens consists of seven coaxial zones Z1, Z2, Z3, Z4, Z5, Z6, Z7 adjacent to one another and each delimited by a respective maximum radius or outer radius r1, r2, r3, r4, r5, r6, r7, and the coefficients $q_o, \ldots q_{11}$ of the Jacobi polynomials for defining the refractive profile of each coaxial zone Z1, Z2, Z3, Z4, Z5, Z6, Z7 are in respective ranges. The ranges of the coefficients $q_o, \ldots q_{11}$ referring to the zones Z1, Z2, Z3, Z4, Z5, Z6 are given in the following six tables.

|    |     | Min       | Max       |
|----|-----|-----------|-----------|
| Z2 | q0  | 4.86E−02  | 6.62E−02  |
|    | q1  | −3.89E−02 | −2.99E−02 |
|    | q2  | 1.84E−02  | 2.21E−02  |
|    | q3  | −1.25E−02 | −1.09E−02 |
|    | q4  | 6.34E−03  | 7.39E−03  |
|    | q5  | −4.76E−03 | −4.09E−03 |
|    | q6  | 2.73E−03  | 3.18E−03  |
|    | q7  | −2.33E−03 | −2.00E−03 |
|    | q8  | 1.41E−03  | 1.65E−03  |
|    | q9  | −1.32E−03 | −1.14E−03 |
|    | q10 | 8.14E−04  | 9.48E−04  |
|    | q11 | −8.33E−04 | −7.15E−04 |

|    |     | Min       | Max       |
|----|-----|-----------|-----------|
| Z1 | q0  | 3.43E−03  | 4.53E−03  |
|    | q1  | −6.42E−04 | −4.57E−04 |
|    | q2  | 3.87E−04  | 7.84E−04  |
|    | q3  | −5.35E−04 | −2.21E−04 |
|    | q4  | 1.24E−04  | 2.51E−04  |
|    | q5  | −2.04E−04 | −1.15E−04 |
|    | q6  | 7.66E−05  | 1.36E−04  |
|    | q7  | −9.95E−05 | −5.60E−05 |
|    | q8  | 3.96E−05  | 7.04E−05  |
|    | q9  | −5.65E−05 | −3.18E−05 |
|    | q10 | 2.28E−05  | 4.05E−05  |
|    | q11 | −3.56E−05 | −2.01E−05 |

|    |     | Min       | Max       |
|----|-----|-----------|-----------|
| Z3 | q0  | 3.41E−02  | 5.48E−02  |
|    | q1  | −3.46E−02 | −2.25E−02 |
|    | q2  | 1.87E−02  | 2.37E−02  |
|    | q3  | −1.58E−02 | −1.37E−02 |
|    | q4  | 9.02E−03  | 1.04E−02  |
|    | q5  | −6.48E−03 | −5.60E−03 |
|    | q6  | 3.74E−03  | 4.33E−03  |
|    | q7  | −3.16E−03 | −2.73E−03 |
|    | q8  | 1.93E−03  | 2.24E−03  |
|    | q9  | −1.80E−03 | −1.55E−03 |
|    | q10 | 1.11E−03  | 1.29E−03  |
|    | q11 | −1.13E−03 | −9.79E−04 |

|    |     | Min       | Max       |
|----|-----|-----------|-----------|
| Z4 | q0  | 4.97E−02  | 6.95E−02  |
|    | q1  | −3.31E−02 | −2.21E−02 |
|    | q2  | 1.59E−02  | 2.42E−02  |
|    | q3  | −8.50E−03 | −5.15E−03 |
|    | q4  | −1.06E−03 | 9.84E−04  |
|    | q5  | −1.47E−03 | −1.42E−04 |
|    | q6  | 9.46E−05  | 9.80E−04  |
|    | q7  | −7.16E−04 | −6.91E−05 |
|    | q8  | 4.89E−05  | 5.06E−04  |
|    | q9  | −4.07E−04 | −3.93E−05 |
|    | q10 | 2.82E−05  | 2.92E−04  |
|    | q11 | −2.56E−04 | −2.47E−05 |

|    |     | Min       | Max       |
|----|-----|-----------|-----------|
| Z6 | q0  | −1.56E−01 | −1.53E−01 |
|    | q1  | 1.05E−01  | 1.07E−01  |
|    | q2  | −6.68E−02 | −6.41E−02 |
|    | q3  | 3.20E−02  | 3.40E−02  |
|    | q4  | −2.00E−02 | −1.88E−02 |
|    | q5  | 1.22E−02  | 1.29E−02  |
|    | q6  | −8.65E−03 | −8.13E−03 |
|    | q7  | 5.94E−03  | 6.32E−03  |
|    | q8  | −4.47E−03 | −4.20E−03 |
|    | q9  | 3.38E−03  | 3.59E−03  |
|    | q10 | −2.57E−03 | −2.42E−03 |
|    | q11 | 2.13E−03  | 2.26E−03  |

|    |     | Min       | Max       |
|----|-----|-----------|-----------|
| Z5 | q0  | −3.21E−03 | 6.54E−02  |
|    | q1  | −3.68E−02 | 3.16E−03  |
|    | q2  | −1.81E−03 | 1.85E−02  |
|    | q3  | −9.74E−03 | 9.50E−04  |
|    | q4  | −5.58E−04 | 5.72E−03  |
|    | q5  | −3.71E−03 | 3.62E−04  |
|    | q6  | −2.42E−04 | 2.48E−03  |
|    | q7  | −1.81E−03 | 1.77E−04  |
|    | q8  | −1.25E−04 | 1.28E−03  |
|    | q9  | −1.03E−03 | 1.00E−04  |
|    | q10 | −7.19E−05 | 7.37E−04  |
|    | q11 | −6.48E−04 | 6.32E−05  |

Therefore, each zone Z1, Z2, Z3, Z4, Z5, Z6 is described by the first twelve terms of the Forbes series expansion.

The last zone Z7, i.e., the outermost zone, has coefficients $q_o, \ldots q_{11}$ of the Jacobi polynomials identically null being a simple aspherical surface, in turn described by the equation $$z(r) = \frac{cr^2}{1 + \sqrt{1 - (1+k)c^2 r^2}}$$

the parameters of which are given by c=curvature of the base sphere of the front or rear surface of the lens, and k=conical constant of the front or rear surface.

The maximum radii or outer radii r1, r2, r3, r4, r5, r6, r7 of the corresponding concentric zones Z1, Z2, Z3, Z4, Z5, Z6, Z7 are preferably between 0.5 mm and 3.0 mm.

Preferably the outer radii of the zones Z1, Z2, Z3, Z4, Z5 and Z6 can be equal to r1=0.4-0.55, mm, r2=0.6-0.7 mm, r3=0.8-0.9 mm, r4=1.25-1.45 mm, r5=1.55-1.70 and r6=2.15-2.35 mm, respectively, while the outer radius of the outer zone Z7 is always r3=3.0 mm.

Figure 13A:
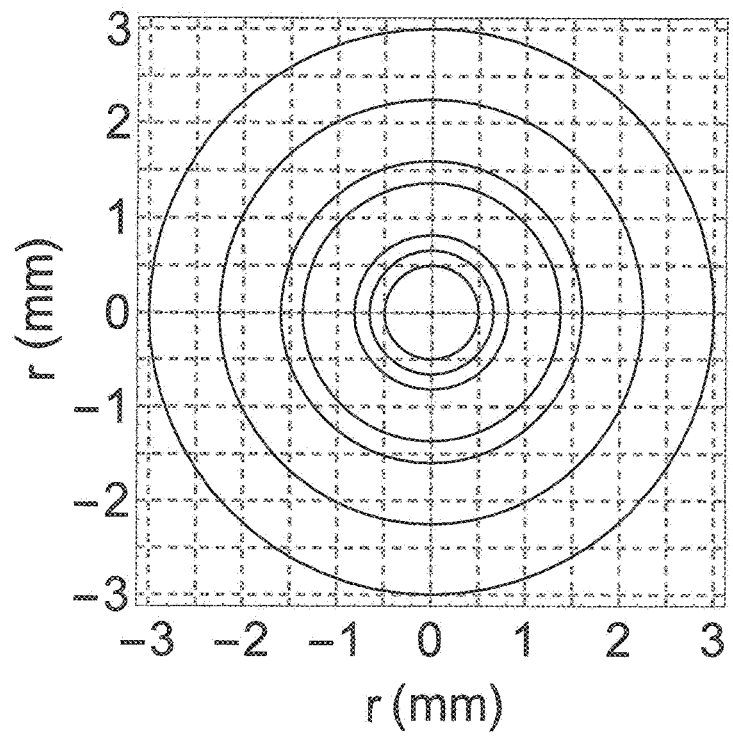
FIG. 13a depicts the zones in which a surface of a fourth lens according to the invention is divided.

Merely by way of example, said maximum radii delimiting the respective zones can be:

r1=0.5 mm, r2=0.66 mm, r3=0.82 mm, r4=1.37 mm, r5=1.60 mm, r6=2.25 mm and r7=3.0 mm, as shown in FIG. 13a.

The aforesaid seven coaxial zones, namely the inner or central zone Z1, the intermediate annular zones Z2, Z3, Z4, Z5, Z6 and the outer annular zone Z7 completely fill the aperture ("clear aperture") of the optics or lens.

Advantageously, a spherical aberration is induced in the inner or central zone Z1 and in the intermediate annular zones Z2, Z3, Z4, Z5 and Z6 in order to obtain the target TFMTF, in accordance with the Jacobi polynomial coefficient tables indicated above. Instead in the outer zone Z7, no spherical aberration is introduced. In fact, in this case the outermost zone Z7 has null coefficients.

Figure 13B:
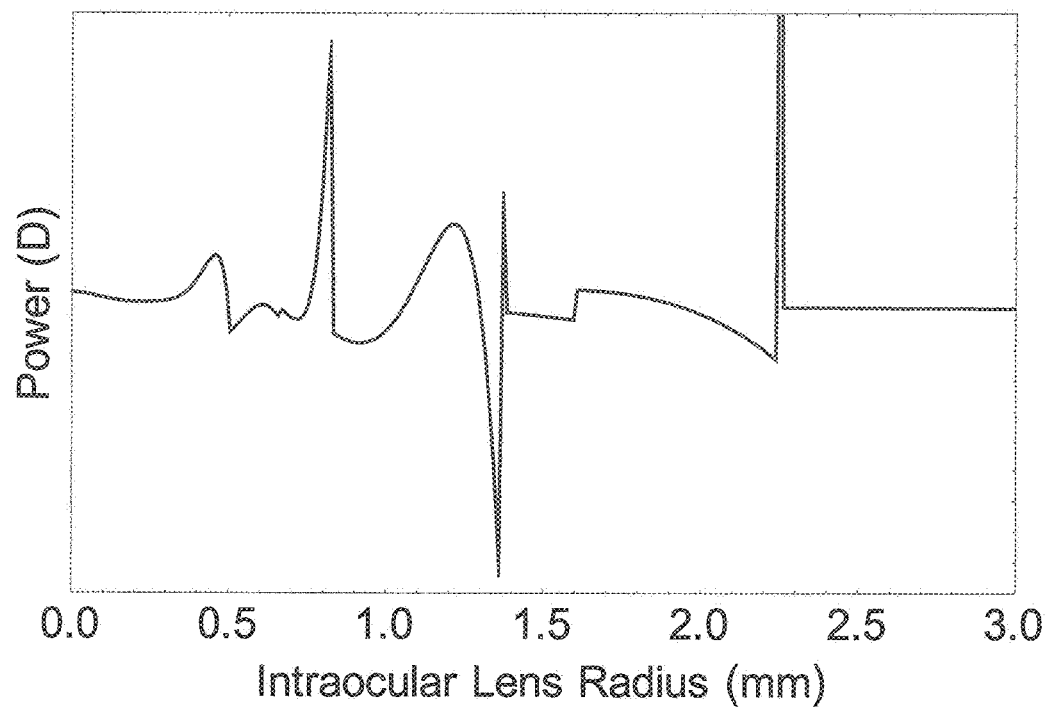
FIG. 13b depicts the trend of the optical power of said fourth lens as a function of the radius.

The graph in FIG. 13b shows the power trend of the lens to induce an improvement in extreme depth of field vision (from far to about 330 mm-350 mm from the patient's eye) with seven zonal subdivisions.

As in examples 2 and 3, also in this case the variation of power in a single zone will be more pronounced with respect to the first example 1 to continuously provide the best visual acuity or the best MTF for both far vision and near vision, i.e., for objects located at a distance of less than 500 mm from the eye, and independent of the pupil diameter which can assume variable values between 2.5 mm and 4.5 mm.

Figure 13C:
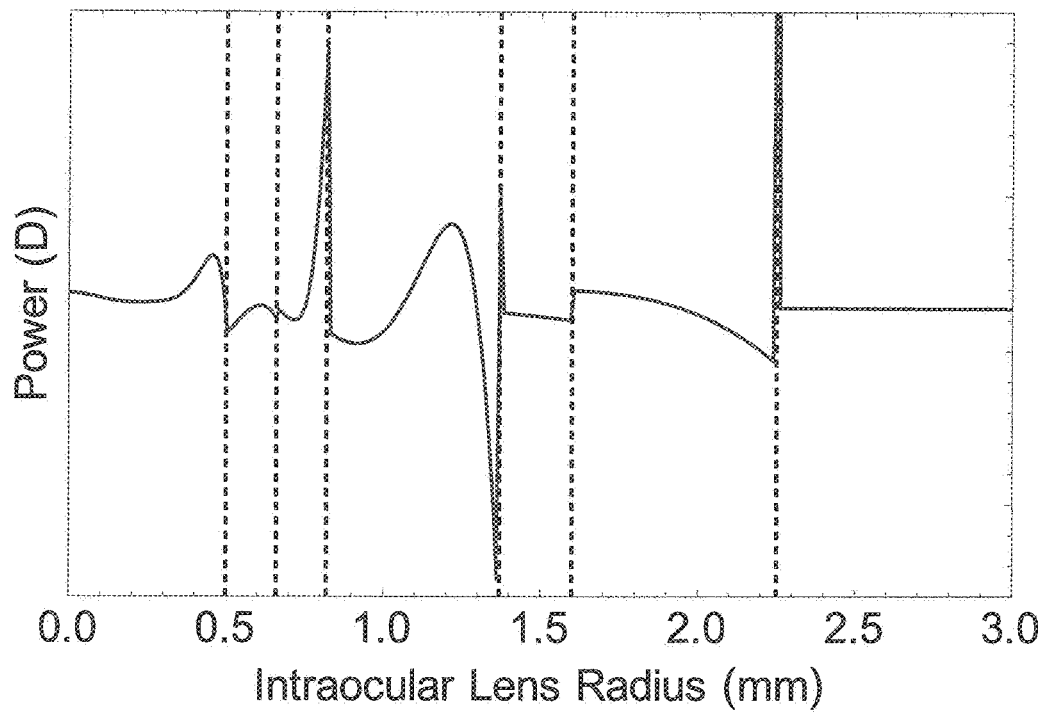
FIG. 13c depicts the graph in FIG. 13b divided into seven zones.

The division into zones is shown more clearly in the graph in FIG. 13c where it is observed that the first zone or central zone Z1 extends from the center of the lens up to a radius of 0.5 mm at which there is a first power discontinuity. A second zone or first intermediate zone Z2 extends from a radius of 0.5 mm to a radius of 0.66 mm at which there is a second power discontinuity. A third zone or second intermediate zone Z3 extends from a radius of 0.66 mm to a radius of 0.82 mm at which there is a third power discontinuity. A fourth zone or third intermediate zone Z4 extends from a radius of 0.82 mm to a radius of 1.37 mm at which there is a fourth power discontinuity. A fifth zone or fourth intermediate zone Z5 extends from a radius of 1.37 mm to a radius of 1.60 mm at which there is a fifth power discontinuity. A sixth zone or fifth intermediate zone Z6 extends from a radius of 1.60 mm to a radius of 2.25 mm at which there is a sixth power discontinuity. A seventh zone or outer zone Z7 extends from a radius of 2.25 mm to the outer radius of 3.0 mm.

In more detail, the central zone Z1 (extending from r=0.0 mm to r=0.5 mm) includes optical powers (see FIG. 13d) which continuously vary between a power P1 at or close to the center of the lens and a power P4 at or close to the edge of the central zone.

Figure 13D:
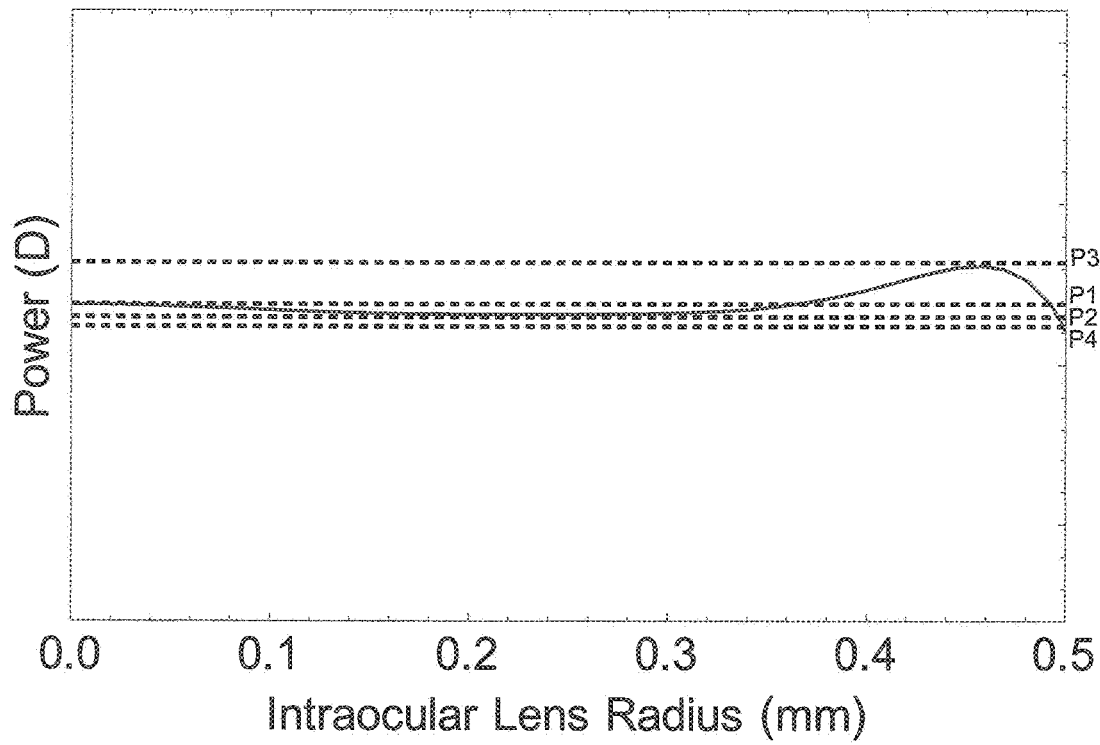

In the graph in FIG. 13d, the initial power P1 can be configured to improve far vision, or it can assume a value greater than that required for far vision, for example a power adapted to determine the best visual acuity or the best MTF for near vision for objects located at a distance of about 1.0 m from the patient's eye or for even nearer vision (about 300 mm).

In more detail, in the graph in FIG. 13d the power of the inner or central zone Z1, up to a radius of 0.5 mm, is configured to improve near vision (at about 1.0 m) and progressively decreases from the center of the lens from the value P1 up to a minimum value P2 in presence of a slightly negative spherical aberration in a first central sub-zone (for example, to help improve far vision), for example extending up to about 0.25 mm from the center of the lens. Continuing towards the outside of the central zone, the power progressively increases, in presence of a positive spherical aberration in a second central sub-zone, up to a maximum value P3, for example at a radius equal to about 0.45 mm, and then decreases to the minimum value P4 at the outer edge of the zone Z1 in presence of a negative spherical aberration in a third central sub-zone: thereby the central zone Z1 is effectively divided into three sub-zones in which the power variation alternately contributes to far vision and near vision so that the patient has a vision quality which is more independent of the pupil diameter.

Figure 13E:
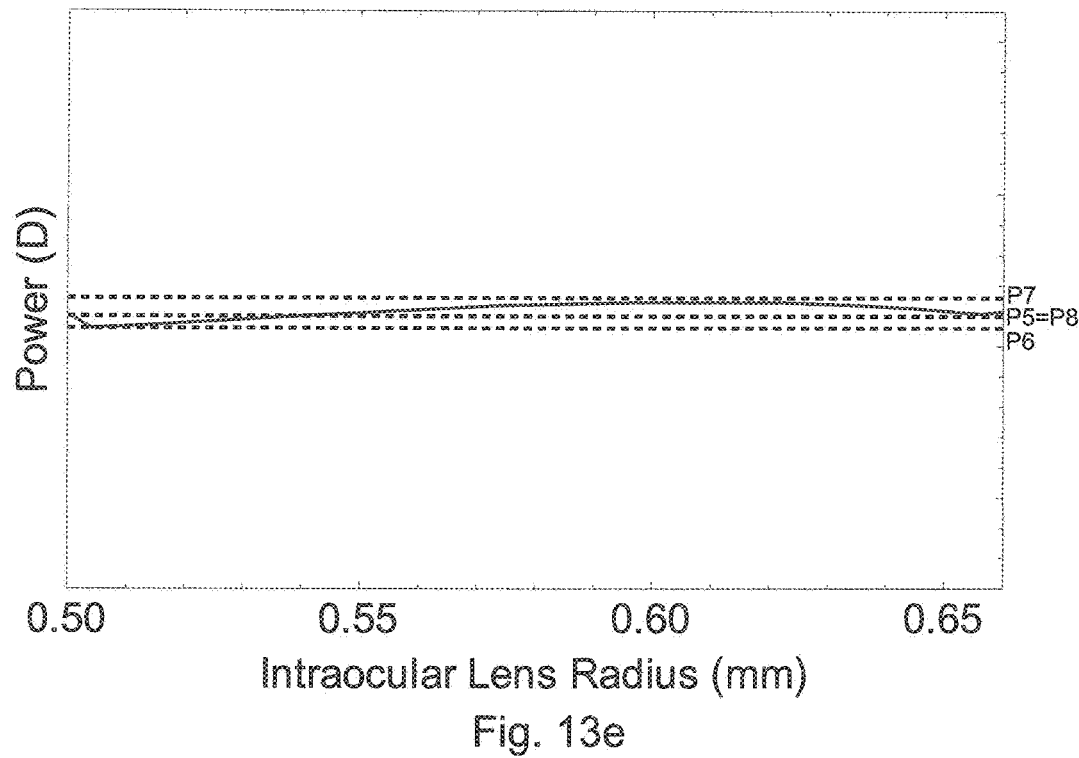

The power in the first intermediate zone Z2 (FIG. 13e), following the central one (i.e., the zone between a radius of 0.5 mm and 0.65 mm), progressively decreases from a power value P5 to a minimum power value P6, for example at the radius of about 0.55 mm; then it increases further until reaching a maximum power P7, for example at the radius of about 0.61 mm, and then decreases until reaching the power P8, which coincides with the power P5, at the outer edge of the zone Z2. Since the values P5 and P8 are also lower than P4 (see FIG. 13c), this intermediate zone Z2 overall induces a change in power such as to favor vision for objects positioned at a distance from the patient, between the intermediate distance (1.0 m) and the distant one (far field).

Figure 13F:
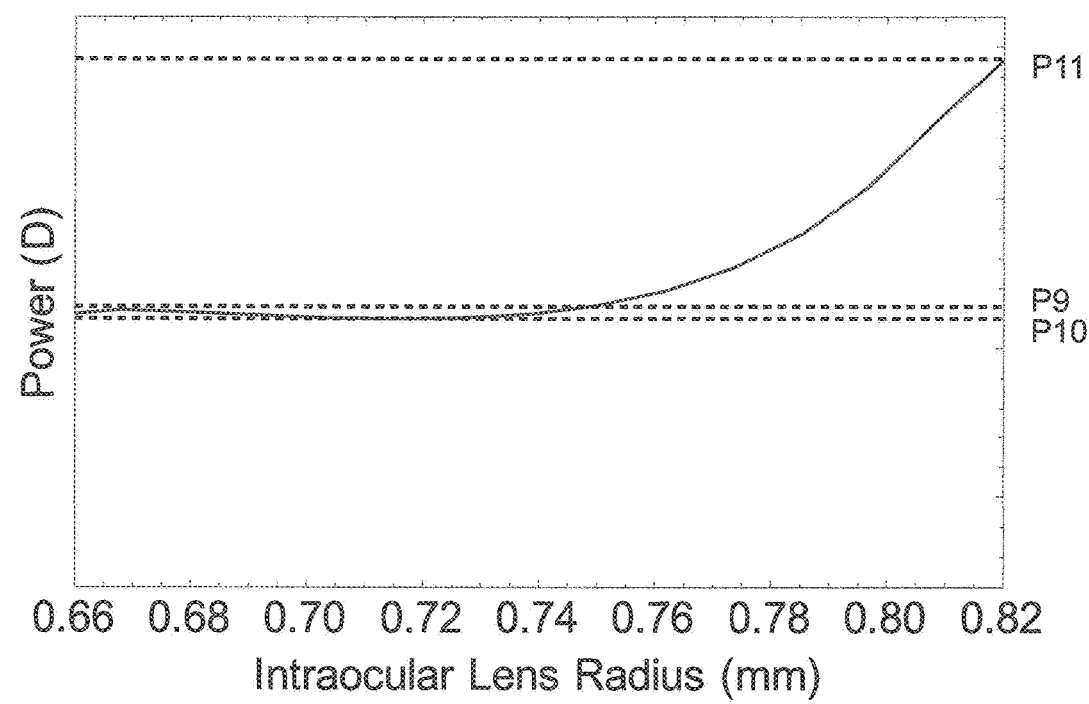

Moving farther away from the center of the lens, in the second intermediate zone Z3 (FIG. 13f), between a radius of 0.66 mm and 0.82 mm, the optical power first slightly decreases from a value P9 to a minimum value P10 and then progressively increases with the increase of the radius from the optical axis up to the extreme value P11. In fact, this intermediate zone Z3 provides a slight negative spherical aberration in the initial part thereof, for example up to a radius of about 0.71 mm, and a more pronounced positive spherical aberration in the final part thereof close to the outer edge of the zone Z3. The power values between P9 and P10 contribute to an improved far vision, while value P11 contributes to an improved near vision. Preferably, the power values P9 and P10 are between P6 and P7 and the value P11 is higher than the average power value of the central zone. Therefore, this intermediate zone Z3 overall has opposite behavior to that of the previous zone Z2 and contributes to maintaining the best visual acuity or the best MTF for both far vision and near proximal vision independently of pupil diameter.

Figure 13G:
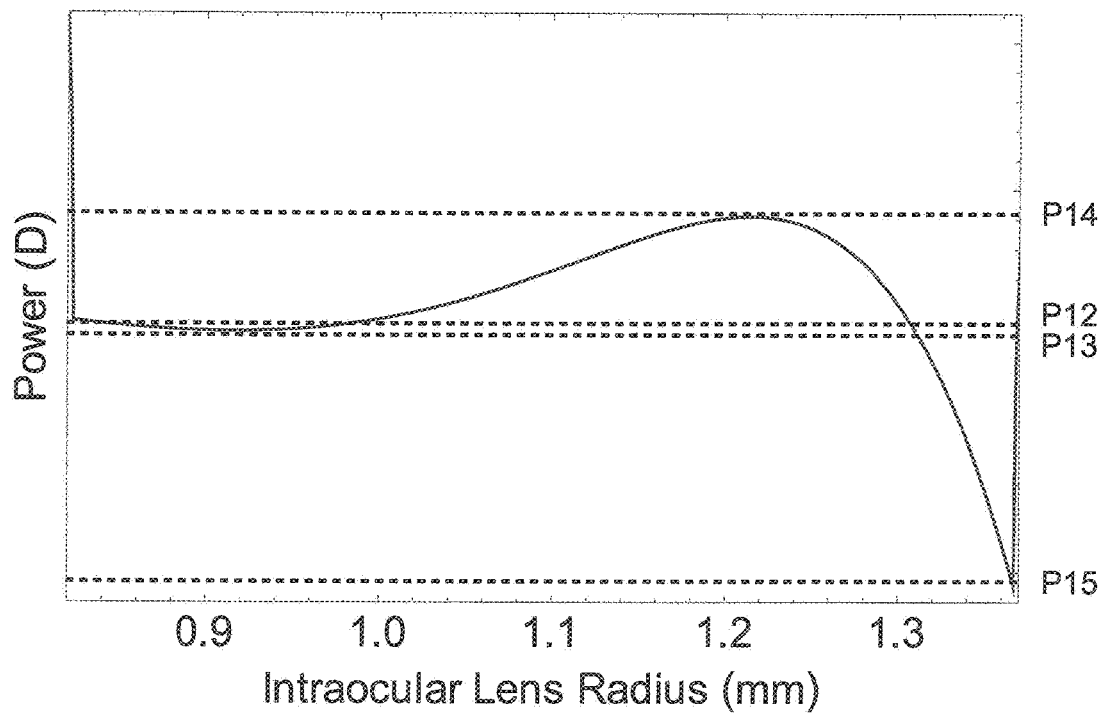

In the third intermediate zone Z4 (FIG. 13g), between a radius of 0.82 mm and a radius of 1.37 mm, the power first slightly decreases from a value P12 to a value P13, for example at a radius of about 0.92 mm, and then progressively increases with the increase of the radius from the optical axis up to reaching a maximum value P14, for example at a radius of about 1.2 mm, and then decreases to the value P15 at the outer edge of the zone Z4. In fact, this zone Z4 overall provides a positive spherical aberration up to the radius corresponding to the value P14 and therefore a negative spherical aberration on the outermost part thereof. In this case the power values P12 and P14 contribute most to improving vision quality in a range between the near intermediate field (1.0 m) and far field while the end value P15 essentially contributes to improving far vision. The overall effect of this zone Z4 is to simultaneously contribute to the improvement of near and far vision.

Figure 13H:
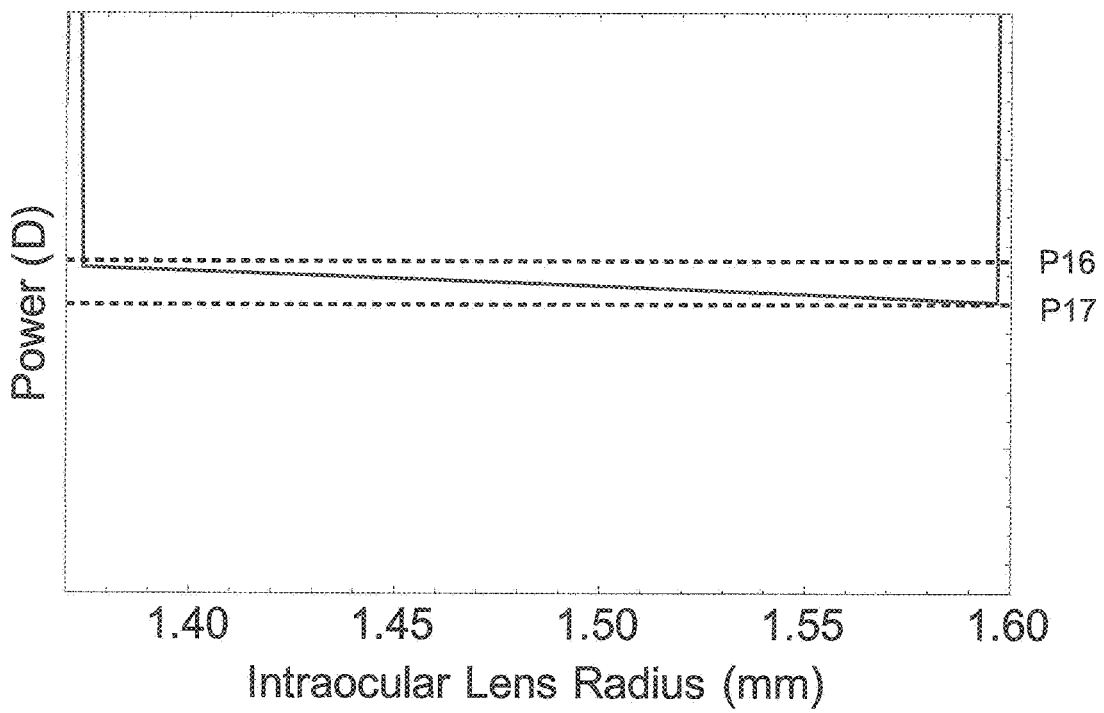

In the fourth intermediate zone Z5 (FIG. 13h), between a radius of 1.37 mm and a radius of 1.60 mm, the power progressively decreases from a value P16 to a value P17 on the outermost edge thereof in presence of a negative spherical aberration in said intermediate annular zone Z5; in this case the power values between P16 and P17 most contribute to improving the vision quality in a range between the near intermediate field (1.0 m) and far field. The overall effect of this zone Z5 is to contribute to improving vision between the intermediate and far fields.

Figure 13I:
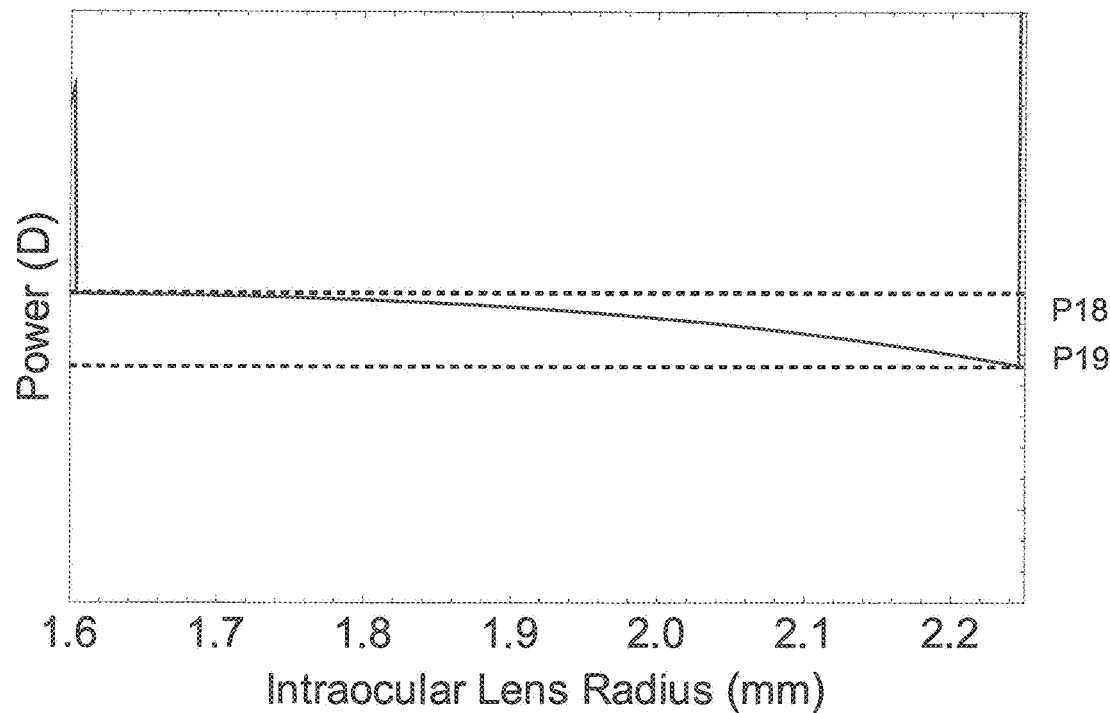

In the fifth intermediate zone Z6 (FIG. 13*i*), between a radius of 1.60 mm and a radius of 2.25 mm, the power progressively decreases with the increase of the radius from the optical axis from a value P18 to a value P19, in presence of a negative spherical aberration close to the outer edge thereof, and contributes more to improving the vision quality in a range from far to near including the intermediate field for very large pupil diameters (where the applied power typically corrects vision only in the far field) comprised between 3.2 mm and 4.5 mm.

Figure 13L:
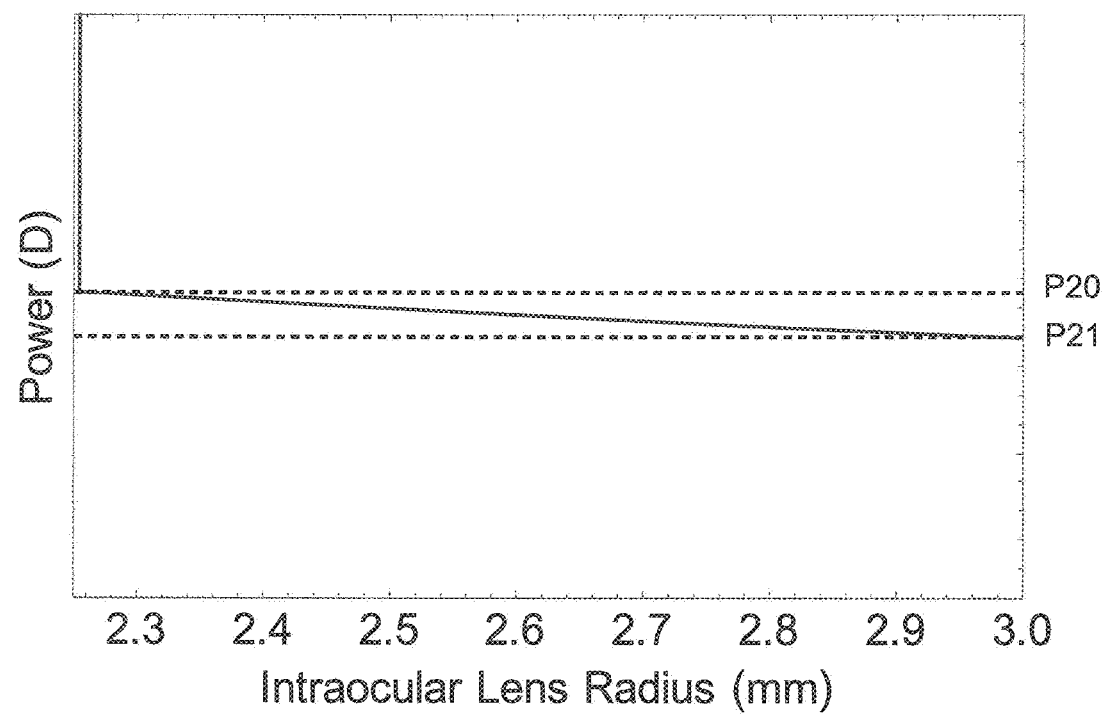

In the outer zone Z7 (FIG. 13*l*), between a radius of 2.25 mm and a radius of 3.0 mm, an aspherical monofocal profile is provided with a power so as to reduce, correct, or cancel the positive spherical aberration of the cornea. Also in this zone Z7 the power gradually decreases from a value P20 to a value P21 as the radius from the optical axis increases, so as to compensate at least partially for the positive spherical aberration of the cornea.

The average power value between P20 and P21 is substantially equal to the average power value of the central zone Z1, with a tolerance of ±0.3 D.

Example 5

In this example of the second embodiment of the invention, at least the front surface or the rear surface of the lens has three coaxial zones Z1, Z2, Z3 adjacent to one another and each delimited by a respective maximum radius or outer radius r1, r2, r3, and the coefficients $q_o, \ldots q_2$ of the Jacobi polynomials for defining the refractive profile of each coaxial zone Z1, Z2, Z3 are in the respective ranges. The ranges of the coefficients $q_o, \ldots q_2$ referring to zones Z1, Z2 are given in the following two tables.

|    |       | Min        | Max        |
|----|-------|------------|------------|
| Z1 | $q_0$ | −3.63E−01  | −3.58E−01  |
|    | $q_1$ | −4.71E−02  | −4.55E−02  |
|    | $q_2$ | 1.98E−02   | 2.05E−02   |

|    |       | Min        | Max        |
|----|-------|------------|------------|
| Z2 | $q_0$ | 7.29E−04   | 7.29E−04   |
|    | $q_1$ | −1.80E−13  | −1.80E−13  |
|    | $q_2$ | −2.60E−13  | −2.60E−13  |

Each zone Z1, Z2 is described by the first three terms of the Forbes series expansion.

The last zone Z3, i.e., the outermost zone, has coefficients $q_o, \ldots q_2$ of the Jacobi polynomials identically null being a simple aspherical surface, in turn described by the equation $$z(r) = \frac{cr^2}{1+\sqrt{1-(1+k)c^2r^2}}$$

the parameters of which are given by
c=inverse of the radius of curvature R of the base sphere of the front or rear surface of the lens, and
k=conical constant of the front or rear surface.

The maximum radii or outer radii r1, r2, r3 of the corresponding concentric zones Z1, Z2, Z3 are preferably between 0.5 mm and 3.0 mm.

Preferably the outer radii of the respective zones Z1 and Z2 can be equal to r1=0.9-1.1 mm and r2=1.4-1.6 mm, while the outer radius of the outer zone Z3 is always r3=3.0 mm.

Figure 14A:
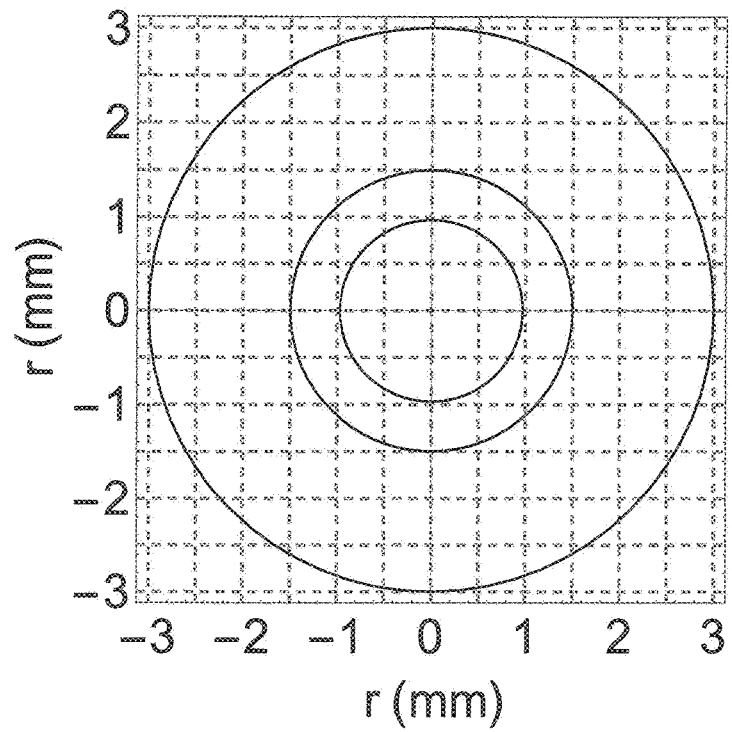
FIG. 14a depicts the zones in which a surface of a fifth lens according to the invention is divided.

Merely by way of example, said maximum radii delimiting the respective zones are: r1=1.0 mm, r2=1.5 mm, r3=3.0 mm as shown in the graph in FIG. 14*a*.

The aforesaid three coaxial zones, namely the inner or central zone Z1, the intermediate annular zone Z2 and the outer annular zone Z3, completely fill the aperture ("clear aperture") of the optics or lens.

Advantageously, a spherical aberration is induced in the central zone Z1 and in the intermediate zone Z2 in order to obtain the target TFMTF, in accordance with the Jacobi polynomial coefficient tables indicated above. Instead in the outer zone Z3, no spherical aberration is introduced. In fact, in this case the outermost zone Z3 has null coefficients.

Figure 14B:
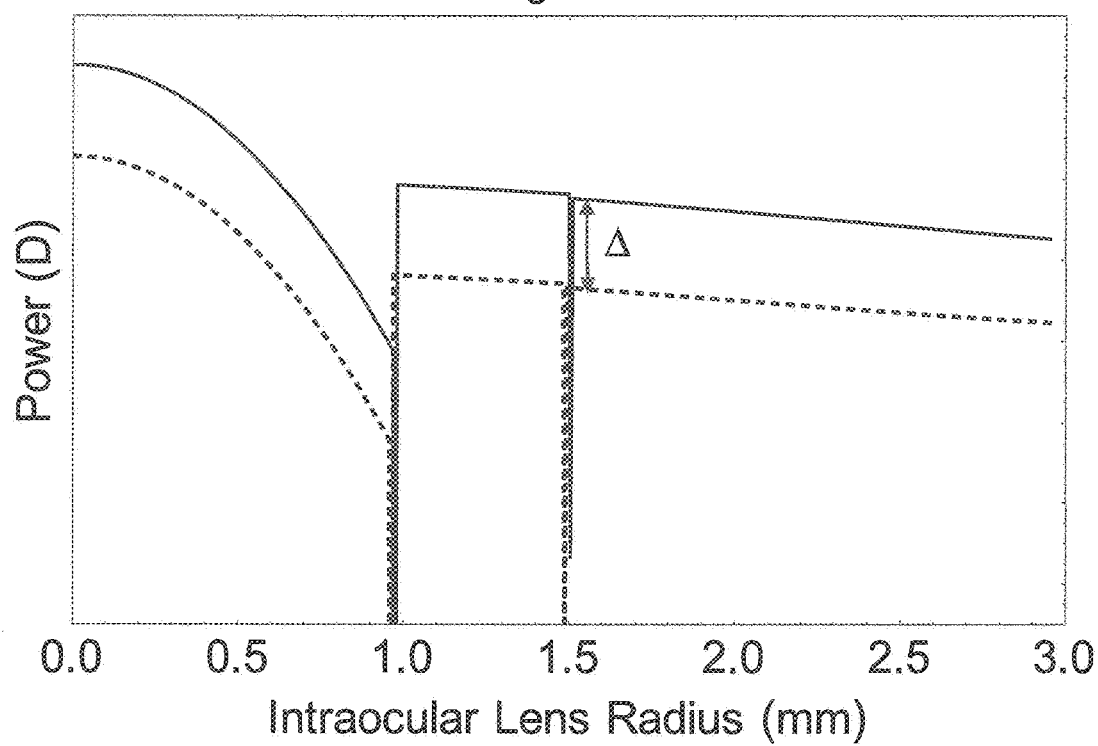
FIG. 14b depicts the trend of the optical power of said fifth lens as a function of the radius.
Figure 14:
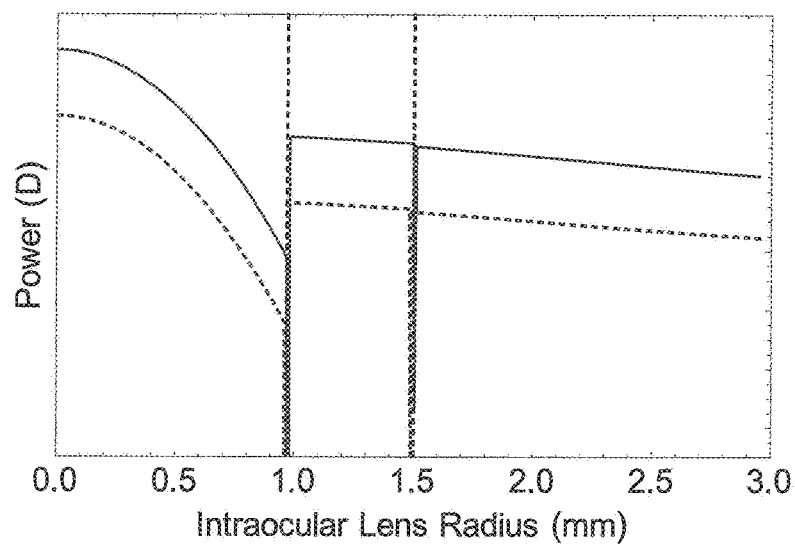
FIG. 14c depicts the graph in FIG. 14b divided into three zones.
FIGS. 14d-14e represent the trend of the optical power of said fifth lens in the respective zones.
Figure 14:
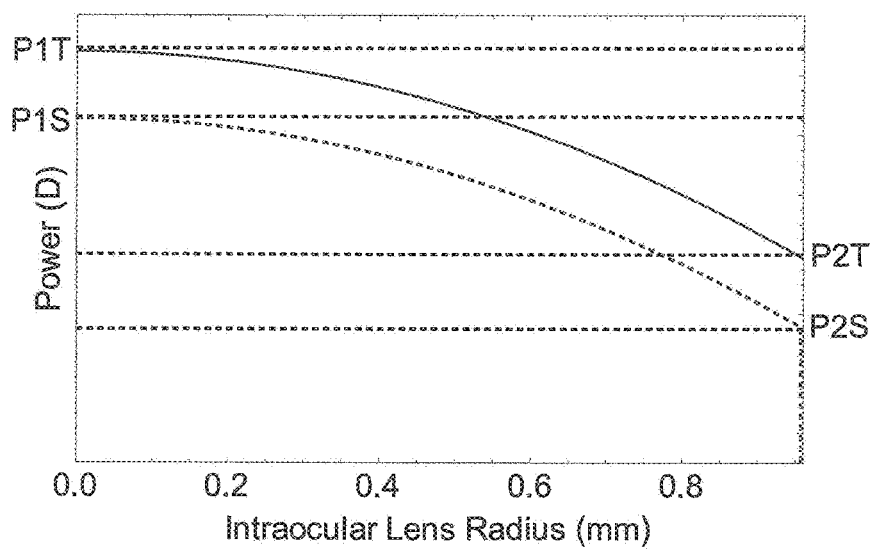
Figure 14:
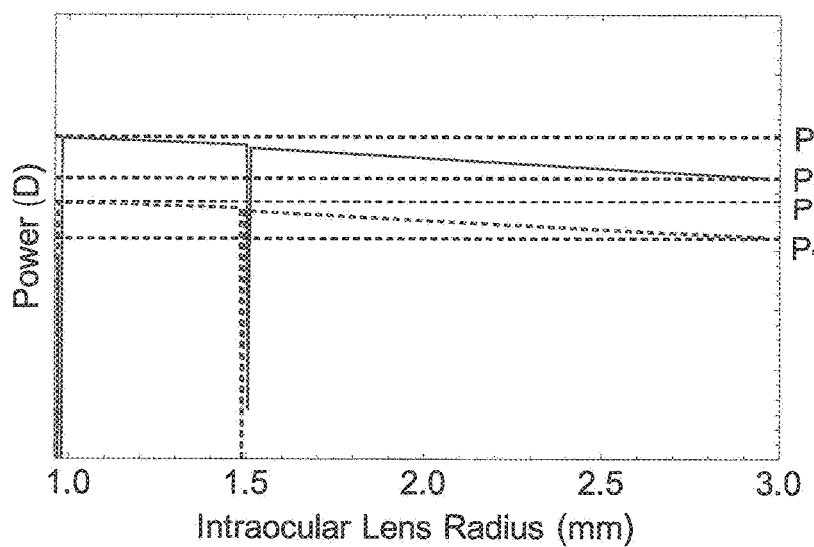

FIG. 14*b* shows the division of the front surface of the lens into only three distinct concentric zones in which the power varies with a different trend from zone to zone. Two different powers are distinguished in the figure and reported with a dashed and continuous line due to the fact that this lens has a cylindrical power (i.e., distinct by sagittal meridian and tangential meridian, orthogonal to each other). FIG. 14*b* shows the power trend referring to the tangential meridian (continuous line) and the sagittal meridian (dotted line). Still from the graph in FIG. 14*b* it can be observed that the difference, A, between the two powers is almost constant as the radius (Intraocular Lens Radius) of the aperture varies. Such a difference precisely represents the cylindrical power of the lens.

This separation of power (between tangential and sagittal) can be achieved on the lens in two distinct manners:

(1) applying on the surface of the lens, in which there is no aspherical zonal variation with coefficients of Jacobi polynomials to extend the depth of field—therefore, in the specific case, on the rear surface of the lens—a toric deformation compatible with the difference in cylindrical power, Δ, which is to be corrected while leaving the front part unchanged;

(2) applying this toric deformation on the surface itself where the aspherical zonal variation is present with coefficients of Jacobi polynomials to extend the depth of field; in general, in this second case, the coefficients of Jacobi polynomials can assume different values if referring respectively to the tangential or sagittal meridian.

The division into zones is shown more clearly in the graph in FIG. 14*c*, where it can be observed that the first zone or central zone Z1 extends from the optical axis, or from the center of the surface (0.0 mm), up to a radius equal to 1.0 mm at which there is a first power discontinuity; an intermediate zone Z2 then follows which extends from a radius equal to 1.0 mm up to a radius equal to 1.5 mm at which there is a second power discontinuity; finally there is a third zone or outer zone Z3 between a radius of 1.5 mm and the outer radius of the surface equal to 3.0 mm.

The central zone (ranging from r=0.0 mm to r=1.0 mm) can include a plurality of optical powers, referring to the tangential power curve, which progressively vary between a first power P1T at or close to the center of the central zone and a second power P2T at or close to the edge of the central zone; or, referring to the sagittal power curve, which vary between a first power P1S at or close to the center of the central zone and a second power P2S at or close to the edge of the central zone.

In the graph in FIG. 3 the trend of the optical power limited to only the central zone is shown: a value corresponding to far vision can be assigned to the initial power PIT, or P1S, or it can be assigned a value greater than that required to correct far vision, for example, as in this case, a power adapted to provide the best visual acuity or the best MTF for near intermediate vision, i.e. for objects located at a distance of about 500 mm from the patient's eye.

The graph in FIG. 14d shows the trend of the optical power limited to the central zone Z1 only. The power of the central zone (within a radius of 1.0 mm) can gradually decrease, with the increase of the distance from the optical axis, from the value in axis PIT, or P1S, up to a value P2T, or P2S (corresponding, for example, to the power value required to correct far vision in proximity of the junction between the inner and intermediate zone). Thus, a negative spherical aberration is induced in said central zone to extend the depth of field.

Distinguished between tangential and sagittal, the power in the intermediate zone and in the outer zone (i.e., between a radius of 1.0 mm and 3.0 mm—see FIG. 14e) corresponds in this case on average to the value required to correct far vision and progressively decreases as the radius from the optical axis increases but in a less pronounced manner (with a lower gradient) with respect to the central zone. In the intermediate zone Z2 a negative spherical aberration is induced to extend the depth of field; while in the outer zone Z3 an aspherical monofocal profile is provided with a power so as to reduce, correct, or cancel the positive spherical aberration of the cornea.

In the illustrated embodiment, the power of the central zone progressively decreases from a value P1T (P1S) to a value P2T (P2S) at the radius of 1.0 mm; in the intermediate zone and in the outer zone (FIG. 14e) the power progressively decreases from a value P3T—or P3S—(greater than P2T—or P2S—but less than HT—or P1S) at the radius of 1.0 mm, to a value P4T—or P4S—(greater than P2T—or P2S—but less than P3T or P3S) at the outer edge of the lens. Alternatively, the radial decrease in power within the outer zone can be such that the value P4T—or P4S—is less than P2T—or P2S. There is a power discontinuity at the passage between the intermediate zone and the outer zone, albeit slight.

As already shown in examples 2, 3 and 4 of the first embodiment, also for the second embodiment, in a manner similar to that shown in this example 5, the profile of one or both front and rear surfaces of the lens can be configured to provide a more complex radial power variation (i.e., divided into a greater number of zones each with a more articulated power trend), than that represented in FIG. 14b, in order to further extend the depth of field of the IOL by distributing it over different pupil diameters.

The disclosures of examples of lenses presented so far refer to the one-dimensional case but can be extended to the two-dimensional case, if it is intended to consider enhanced depth of field variations with enhanced wavefronts with cylindrical symmetry, for example for the embodiment of a lens aimed at enhanced depth of field variation and correction of astigmatism.

Extended intraocular lenses can therefore be produced in which a first lens surface, for example the front surface, is described with an aspherical power series expansion of the type attributable, without limiting the invention, to one of the embodiments described above while on the second surface, rear in this case, a cylindrical surface is applied with the aim of correcting the residual astigmatism of the patient's eye.

The disclosures of examples of lenses presented so far can be extended to the case of lens systems, if it is intended to consider enhanced depth of field variations with wavefronts enhanced in a complementary manner in order to obtain a control of the depth of field variation in case of binocular correction.

The invention claimed is:

1. An implantable or wearable corrective lens for ophthalmic use, having a front surface and a rear surface, wherein at least one surface of said front surface and rear surface has an aspherical refractive profile with circular or rotational symmetry with respect to an optical axis, said aspherical refractive profile being divided into a number Y of mutually coaxial zones, with Y varying from 3 to 7, a profile of each zone being of refractive type only and having a geometric elevation z(r) defined by a series expansion of Forbes polynomials at least up to the third term $$z(r) = \frac{cr^2}{1+\sqrt{1-(1+k)c^2r^2}} + \left(\frac{r}{r_{max}}\right)^4 \sum_{i=0}^{x} q_i Q_i\left(\left(\frac{r}{r_{max}}\right)^2\right)$$

where
i=variable number from 0 to x, with 2≤x≤11,
r=aperture radius of the at least one surface, which is variable from 0 to Imax,
c=inverse of a radius of curvature R of a base sphere of said at least one surface,
k=conical constant of said at least one surface,
$r_{max}$=maximum aperture radius of said at least one surface
$Q_i$=Jacobi polynomials of index (α=0 and β=4)
$q_i$=coefficients of the Jacobi polynomials $Q_i$,
wherein coefficients $q_i$ of the Jacobi polynomials for defining the refractive profile of each coaxial zone all have a non-zero value for the refractive profile of a number of zones equal to Y−1, and equal to zero for the refractive profile of the outermost zone,
wherein the entire front surface or the entire rear surface consists of said aspherical refractive profile divided into said number Y of coaxial zones of refractive type only,
wherein said coaxial zones are adjacent to each other and a thickness continuity is provided in a junction or transition zone between two mutually adjacent zones,
wherein said coaxial zones are concentric zones, wherein a spherical aberration is only provided in a central zone Z1 and in at least one intermediate annular zone Z2 of said coaxial zones, and
wherein a discontinuity of optical power is provided between each coaxial zone and the next one;
wherein said coefficients $q_i$ are in the following range −0.422≤$q_i$≤0.800;
wherein a depth of field variation of the lens is provided in a power range between −1D and +4.0D;
and wherein outer radii of the coaxial zones are between 0.5 mm and 3 mm.

2. A lens according to claim 1, wherein said at least one surface comprises, or consists of, three concentric coaxial zones Z1, Z2, Z3 adjacent to one another and each delimited by a respective maximum radius or outer radius r1, r2, r3, wherein the coefficients ($q_o$, . . . $q_2$) of the Jacobi polynomials for defining the refractive profile of each concentric coaxial zone $$z(r) = \frac{cr^2}{1 + \sqrt{1-(1+k)c^2r^2}} + \left(\frac{r}{r_{max}}\right)^4 \sum_{i=0}^{2} q_i Q_i\left(\left(\frac{r}{r_{max}}\right)^2\right)$$

are in the following range $-0.363 \leq q_i \leq 0.021$ with i=0, 1, 2, the value of all the coefficients $q_i$ being non-zero for the refractive profile of two concentric coaxial zones Z1, Z2 of said three concentric coaxial zones, and being equal to zero for the refractive profile of the outermost zone Z3.

3. A lens according to claim 2, wherein said three concentric coaxial zones are a central zone Z1 extending from the optical axis to a first outer radius r, an intermediate annular zone Z2 extending from said first outer radius $r_1$ to a second outer radius $r_2$, and an outer annular zone $Z_3$ extending from said second outer radius $r_2$ to a third outer radius r3 coinciding with the outer radius of the lens surface.

4. A lens according to claim 3, wherein a spherical aberration is provided only in the central zone Z1 and in the intermediate annular zone Z2.

5. A lens according to claim 2, wherein the outer radius of said two coaxial zones Z1, Z2 is equal to r1=0.9-1.1 mm and r2=1.4-1.6 mm respectively, while the outer radius of the outermost zone Z3 is always r3=3.0 mm.

6. A lens according to claim 3, wherein the optical power of the central zone Z1 decreases from a first value P1 to a second value P2 at the first outer radius $r_1$; wherein the optical power in the intermediate annular zone Z2 and the outer annular zone Z3 decreases from a third value P3 at the first outer radius $r_1$ to a fourth value P4 at the third outer radius $r_3$; where P2<P4<P3<P1 or P4<P2<P3<P1.

7. A lens according to claim 1, wherein said at least one surface comprises, or consists of, five concentric coaxial zones Z1, Z2, Z3, Z4, Z5 adjacent to one another and each delimited by a respective maximum radius or outer radius $r_1$, $r_2$, $r_3$, $r_4$, $r_5$, wherein the coefficients ($q_o$, . . . $q_{11}$) of the Jacobi polynomials for defining the refractive profile of each concentric coaxial zone $$z(r) = \frac{cr^2}{1 + \sqrt{1-(1+k)c^2r^2}} + \left(\frac{r}{r_{max}}\right)^4 \sum_{i=0}^{11} q_i Q_i\left(\left(\frac{r}{r_{max}}\right)^2\right)$$

are in the following range $-0.422 \leq q_i \leq 0.700$ or in the following range $-0.069 \leq q_i \leq 0.115$ with i =0, . . . 11, the value of all the coefficients $q_i$ being non-zero for the refractive profile of four concentric coaxial zones Z1, Z2, Z3, Z4 of said five concentric coaxial zones, and being equal to zero for the refractive profile of the outermost zone Z5.

8. A lens according to claim 7, wherein said five concentric coaxial zones are a central zone Z1 extending from the optical axis to a first outer radius r1, a first intermediate annular zone Z2 extending from said first outer radius r1 to a second outer radius r2, a second intermediate annular zone Z3 extending from said second outer radius r2 to a third outer radius r3, a third intermediate annular zone Z4 extending from said third outer radius r3 to a fourth outer radius r4, and an outer annular zone Z5 extending from said fourth outer radius r4 to a fifth outer radius r5 coinciding with the outer radius of the lens surface.

9. A lens according to claim 8, wherein a spherical aberration is provided only in the central zone Z1 and in the three intermediate annular zones Z2, Z3, Z4.

10. A lens according to claim 8, wherein, as the radius increases, the optical power of the central zone Z1 starting from the center of the lens
  increases from a first value P1 to a second value P2 in the presence of a positive spherical aberration in a first central sub-zone;
  decreases from said second value P2 to a third value P3 in the presence of a negative spherical aberration in a second central sub-zone;
  increases from said third value P3 to a fourth value P4 at the first outer radius r1 in the presence of a positive spherical aberration in a third central sub-zone;
preferably wherein the optical power in the first intermediate annular zone Z2 starting from the first outer radius r1
  decreases from a fifth value P5 to a sixth value P6 in the presence of a negative spherical aberration in an initial part of said first intermediate annular zone Z2,
  and increases from said sixth value P6 to a seventh value P7 at the second outer radius r2 in the presence of a positive spherical aberration in a final part of said first intermediate annular zone Z2;
preferably wherein both the fifth value P5 and the sixth value P6 are in a range between the third value P3 and the fourth value P4, and wherein the seventh value P7 is greater than an average power value of the central zone Z1;
preferably wherein the optical power in the second intermediate annular zone Z3 starting from the second outer radius r2
  increases from an eighth value P8 to a ninth value P9 in the presence of a positive spherical aberration in an initial part of said second intermediate annular zone Z3;
  and decreases from said ninth value P9 to a tenth value P10 at the third outer radius r3 in the presence of a negative spherical aberration in a final part of said second intermediate annular zone Z3,
preferably wherein both the eighth value P8 and the ninth value P9 are in a range between the third value P3 and the fourth value P4, and wherein the tenth value P10 is less than the average power value of the central zone Z1;
preferably wherein the optical power in the third intermediate annular zone Z4 starting from the third outer radius r3 decreases from an eleventh value P11 to a twelfth value P12 at the fourth outer radius r4 in the presence of a negative spherical aberration; preferably wherein an average power value in said third intermediate annular zone Z4 substantially corresponds to the average power value in the central zone Z1;
preferably wherein the optical power in the outer annular zone Z5 starting from the fourth outer radius r4 decreases from a thirteenth value P13 to a fourteenth value P14 at the fifth outer radius r5; preferably in which P12<P14<P13<P11.

11. A lens according to claim 8, wherein, as the radius increases, the optical power of the central zone Z1 starting from the center of the lens
  decreases from a first value P1 to a second value P2 in the presence of a negative spherical aberration in a first central sub-zone;
  and increases from said second value P2 to a third value P3 at the first outer radius r1 in the presence of a positive spherical aberration in a second central sub-zone;
preferably wherein the optical power in the first intermediate annular zone Z2, starting from the first outer radius r1, decreases from a fourth value P4 to a fifth value P5 in the presence of a negative spherical aberration in said first intermediate annular zone Z2;

preferably wherein the fourth value P4 is less than the second value P2;
preferably wherein the optical power in the second intermediate annular zone Z3 starting from the second outer radius r2
  decreases from a sixth value P6 to a seventh value P7 in the presence of a negative spherical aberration in an initial part of said second intermediate annular zone Z3;
  and increases from said seventh value P7 to an eighth value P8 at the third outer radius r3 in the presence of a positive spherical aberration in a final part of said second intermediate annular zone Z3,
preferably wherein both the sixth value P6 and the seventh value P7 are in the range between the fourth value P4 and the fifth value P5, and wherein the eighth value P8 is greater than an average power value of the central zone Z1;
preferably wherein the optical power in the third intermediate annular zone Z4 starting from the third outer radius r3 increases from a ninth value P9 to a tenth value P10 and decreases from said tenth value P10 to an eleventh value P11 at the fourth outer radius r4 in the presence of an overall negative spherical aberration in said third intermediate annular zone Z4;
preferably wherein the optical power in the outer annular zone Z5 starting from the fourth outer radius r4 decreases from a twelfth value P12 to a thirteenth value P13 at the fifth outer radius r5;
preferably wherein an average power value between P12 and P13 substantially corresponds to the average power value in the central zone Z1.

12. A lens according to claim 7, wherein the outer radius of said four concentric coaxial zones Z1, Z2, Z3, Z4 is equal to r1=0.4-0.5 mm, r2=0.7-0.9 mm, r3=1.25-1.45 mm, and r4=2.15-2.35 mm, respectively, while the outer radius of the outermost zone Z5 is always r3=3.0 mm;
  or wherein the outer radius of said four concentric coaxial zones Z1, Z2, Z3, Z4 is equal to r1 =0.9-1.1 mm, r2=1.25-1.35 mm, r3=1.4-1.6 mm, and r4=2.15-2.35 mm, respectively, while the outer radius of the outermost zone Z5 is always r3=3.0 mm.

13. A lens according to claim 1, wherein said at least one surface comprises, or consists of, seven concentric coaxial zones Z1, Z2, Z3, Z4, Z5, Z6, Z7 adjacent to one another and each delimited by a respective maximum radius or outer radius r1, r2, r3, r4, r5, r6, r7, where the coefficients ($q_o$, ... $q_{11}$) of the Jacobi polynomials for defining the refractive profile of each concentric coaxial zone $$z(r) = \frac{cr^2}{1+\sqrt{1-(1+k)c^2r^2}} + \left(\frac{r}{r_{max}}\right)^4 \sum_{i=0}^{11} q_i Q_i\left(\left(\frac{r}{r_{max}}\right)^2\right)$$

are in the following range $-0.156 \leq q_i \leq 0.107$ with i=0, ... . 11,
  the value of all the coefficients $q_i$ being non-zero for the refractive profile of six concentric coaxial zones Z1, Z2, Z3, Z4, Z5, Z6 of said seven concentric coaxial zones, and being equal to zero for the refractive profile of the outermost zone Z7.

14. A lens according to claim 13, wherein said seven concentric coaxial zones are a central zone Z1 extending from the optical axis to a first outer radius r1, a first intermediate annular zone Z2 extending from said first outer radius r1 to a second outer radius r2, a second intermediate annular zone Z3 extending from said second outer radius r2 to a third outer radius r3, a third intermediate annular zone Z4 extending from said third outer radius r3 to a fourth outer radius r4, a fourth intermediate annular zone Z5 extending from said fourth outer radius r4 to a fifth outer radius r5, a fifth intermediate annular zone Z6 extending from said fifth outer radius r5 to a sixth outer radius r6, and an outer annular zone Z7 extending from said sixth outer radius r6 to a seventh outer radius r7 coinciding with the outer radius of the lens surface.

15. A lens according to claim 14, wherein a spherical aberration is provided only in the central zone Z1 and in the five intermediate annular zones Z2, Z3, Z4, Z5, Z6.

16. A lens according to claim 14, wherein, as the radius increases, the optical power of the central zone Z1 starting from the center of the lens
  decreases from a first value P1 to a second value P2 in the presence of a negative spherical aberration in a first central sub-zone;
  increases from said second value P2 to a third value P3 in the presence of a positive spherical aberration in a second central sub-zone;
  and decreases from said third value P3 to a fourth value P4 at the first outer radius r1 in the presence of a negative spherical aberration in a third central sub-zone;
preferably wherein the optical power in the first intermediate annular zone Z2 starting from the first outer radius r1
  decreases from a fifth value P5 to a sixth value P6 in the presence of a negative spherical aberration in an initial part of said first intermediate annular zone Z2,
  increases from said sixth value P6 to a seventh value P7 in the presence of a positive spherical aberration in an intermediate part of said first intermediate annular zone Z2;
  and decreases from said seventh value P7 to an eighth value P8 in the presence of a negative spherical aberration in a final part of said first intermediate annular zone Z2,
preferably wherein said eighth value P8 coincides with said fifth value P5 and is less than the fourth value P4;
preferably wherein the optical power in the second intermediate annular zone Z3 starting from the second outer radius r2
  decreases from a ninth value P9 to a tenth value P10 in the presence of a negative spherical aberration in an initial part of said second intermediate annular zone Z3;
  and increases from said tenth value P10 to an eleventh value P11 at the third outer radius r3 in the presence of a positive spherical aberration in a final part of said second intermediate annular zone Z3,
preferably wherein both the ninth value P9 and the tenth value P10 are in the range between the sixth value P6 and the seventh value P7, and wherein the eleventh value P11 is greater than an average power value of the central zone Z1;
preferably wherein the optical power in the third intermediate annular zone Z4 starting from the third outer radius r3
  decreases from a twelfth value P12 to a thirteenth value P13 in the presence of a negative spherical aberration in an initial part of said third intermediate annular zone Z4,
  increases from said thirteenth value P13 to a fourteenth value P14 in the presence of a positive spherical aberration in an intermediate part of said third intermediate annular zone Z4,
  and decreases from said fourteenth value P14 to a fifteenth value P15 at the fourth outer radius r4 in the presence of a negative spherical aberration in a final part of said third intermediate annular zone Z4;

preferably wherein the optical power in the fourth intermediate annular zone Z5 starting from the fourth outer radius r4 decreases from a sixteenth value P16 to a seventeenth value P17 at the fifth outer radius r5, in the presence of a negative spherical aberration in said fourth intermediate annular zone Z5, preferably wherein the optical power in the fifth intermediate annular zone Z6 starting from the fifth outer radius r5 decreases from an eighteenth value P18 to a nineteenth value P19 at the sixth outer radius r6, in the presence of a negative spherical aberration in said fifth intermediate annular zone Z6, preferably in which the optical power in the outer annular zone Z7 starting from the sixth outer radius r6 decreases from a twentieth value P20 to a twenty-first value P21 at the seventh outer radius r7; preferably twelfth an average power value between P20 and P21 substantially corresponds to the average power value of the central zone Z1.

17. A lens according to claim 13, wherein the outer radius of said six coaxial zones Z1, Z2, Z3, Z4, Z5, Z6 is equal to r1=0.4-0.55 mm, r2=0.6-0.7 mm, r3=0.8-0.9 mm, r4=1.25-1.45 mm, r5=1.55-1.70 and r6=2.15-2.35 mm, respectively, while the outer radius of the outermost zone Z7 is always r3=3.0 mm.

18. A lens according to claim 1, wherein said lens is an intraocular lens, and wherein said front surface has said aspherical refractive profile with circular or rotational symmetry with respect to the optical axis, while said rear surface comprises at least one cylindrical portion, or vice versa.

* * * * *